US012485188B2

(12) United States Patent
Shu et al.

(10) Patent No.: US 12,485,188 B2
(45) Date of Patent: Dec. 2, 2025

(54) RECOMBINANT ADENO-ASSOCIATED VIRUS WITH MODIFIED AAV CAPSID POLYPEPTIDES

(71) Applicant: Skyline THerapeutics Limited, Cayman Islands (GB)

(72) Inventors: Yanqun Shu, Shanghai (CN); Jinzhao Hou, Shanghai (CN); Heping Li, Shanghai (CN); Qiongqiong Ren, Shanghai (CN); Lumei Xiao, Shanghai (CN); Bing Wu, Shanghai (CN); Peilu Li, Shanghai (CN)

(73) Assignee: Skyline Therapeutics Limited, Cayman Islands (GB)

( * ) Notice: Subject to any disclaimer, the term of this patent is extended or adjusted under 35 U.S.C. 154(b) by 0 days.

(21) Appl. No.: 18/807,211

(22) Filed: Aug. 16, 2024

(65) Prior Publication Data

US 2024/0398992 A1 Dec. 5, 2024

Related U.S. Application Data

(63) Continuation of application No. PCT/CN2023/076389, filed on Feb. 16, 2023.

(30) Foreign Application Priority Data

Feb. 17, 2022 (WO) ................ PCT/CN2022/076619

(51) Int. Cl.

| | |
|---|---|
| ***A61K 48/00*** | (2006.01) |
| ***C07K 14/005*** | (2006.01) |
| ***C07K 16/22*** | (2006.01) |
| ***C12N 15/86*** | (2006.01) |

(52) U.S. Cl.

CPC ........ *A61K 48/0058* (2013.01); *C07K 14/005* (2013.01); *C07K 16/22* (2013.01); *C12N 15/86* (2013.01); *C12N 2750/14122* (2013.01); *C12N 2750/14143* (2013.01); *C12N 2750/14145* (2013.01); *C12N 2750/14152* (2013.01); *C12N 2750/14171* (2013.01)

(58) Field of Classification Search

CPC .............. A61K 48/0058; A61K 48/005; C07K 14/005; C07K 16/22; C12N 15/86; C12N 2750/14122; C12N 2750/14143; C12N 2750/14145; C12N 2750/14152; C12N 2750/14171; A61P 27/02

See application file for complete search history.

(56) References Cited

U.S. PATENT DOCUMENTS

| | | | | |
|---|---|---|---|---|
| 2016/0375151 | A1* | 12/2016 | Schaffer ............... | A61K 9/0048 |
| 2020/0297869 | A1* | 9/2020 | Cepeda ................... | A61P 27/02 |

FOREIGN PATENT DOCUMENTS

| | | | | |
|---|---|---|---|---|
| WO | WO-2016134375 | A1 * | 8/2016 | ......... A61K 48/0008 |
| WO | WO-2020/180951 | A1 | 9/2020 | |
| WO | WO-2021/084133 | A1 | 5/2021 | |
| WO | WO-2021/204407 | A1 | 10/2021 | |

* cited by examiner

*Primary Examiner* — Titilayo Moloye

(74) *Attorney, Agent, or Firm* — Foley & Lardner LLP

(57) ABSTRACT

The present invention relates to a modified adeno-associated virus (AAV) capsid polypeptide and a novel recombinant adeno-associated virus (rAAV) comprising the modified AAV capsid polypeptide for delivering the gene product for the therapy. The present invention also relates to a pharmaceutical composition comprising the rAAV of the present invention, and a method of treating a retinal disease comprising the administration of the rAAV or the pharmaceutical composition of the present invention to an eye of a subject in need thereof.

20 Claims, 19 Drawing Sheets

Specification includes a Sequence Listing.

RECOMBINANT ADENO-ASSOCIATED VIRUS WITH MODIFIED AAV CAPSID POLYPEPTIDES

CROSS-REFERENCE TO RELATED APPLICATIONS

This application is a Continuation of PCT/CN2023/076389, filed Feb. 16, 2023, which claims priority to PCT/CN2022/076619, filed Feb. 17, 2022.

SEQUENCE LISTING

The instant application contains a Sequence Listing which has been submitted in XML format and is hereby incorporated by reference in its entirety. Said XML copy, created on Aug. 14, 2024, is named NP2024TC1626-Sequence Listing.xml and is 63,407 bytes.

TECHNICAL FIELD

The present invention relates to gene therapy. In particular, the present invention relates to a modified adeno-associated virus (AAV) capsid polypeptide and a novel recombinant adeno-associated virus (rAAV) comprising the modified AAV capsid polypeptide for delivering the gene product for the therapy.

BACKGROUND

Gene therapy has recently received increasing attention. The improved gene transfer technology gives great aid to the development of gene therapy.

Gene therapies initially relate to the introduction of a foreign gene into a patient's cell to correct for congenital genetic errors, such as loss-of-function mutations. Most of the currently approved gene therapy protocols have involved the introduction of functional copies of a gene, which is defective in a patient, into somatic cells of the patient. But recently, gene therapy has been broadly defined as the correction of disease phenotype by introducing new genetic information into an organism in need thereof.

In in vivo gene therapy, the transferred gene (transgene) is introduced in situ into the organs, tissues, and cells of the recipient organism, such as muscle hematopoietic stem cells, arterial walls, the nervous system, the lungs, and the eyes.

The in vivo gene therapy by introducing a transgene in situ into the eyes has been used for the treatment of ocular diseases (such as those that cause blindness). Examples of such diseases are retinitis pigmentosa, maculopathy, Leber's congenital amaurosis, Leber's hereditary optic neuropathy, early onset severe retinal dystrophy, full color blindness, retinal palpebral fissure Disease, ocular albinism, ocular albinism, glaucoma, Stargardt disease, choroid-free, age-related macular degeneration (AMD) including Wet-AMD, spinocerebellar ataxia type 7 (SCAT), color blindness, and lysosomes Storage diseases affecting the cornea (such as mucopolysaccharidosis (MPS) IV and MPS VII).

Adeno-associated virus (AAV) is a member of Parvoviridae family. It is a simple single-stranded DNA virus, and requires a helper virus (such as adenovirus) for replication. The genome of a wildtype AAV contains approximately 4.7 kilobases (kb), comprising the cap and rep genes between two inverted terminal repeat (ITR) sequenceswith interrupted palindromic sequences that can fold into hairpin structures that function as primers during initiation of DNA replication. The cap gene encodes the viral capsid protein, and the rep gene is involved in the replication and integration of AAV. AAV can infect a variety of cells, and the viral DNA can be integrated into human chromosome 19 in the presence of the rep product.

A large percentage of rAAV gene therapy under clinical development is focused on the CNS, including the brain and eye. There are a dozen or so capsid serotypes that are currently used as vectors in clinical trials, the most numerous being AAV2-based platforms for ocular diseases. Notably, the first rAAV gene therapy drug approved by the US Food and Drug Administration (FDA), Luxturna, treats patients with an inherited form of vision loss caused by RPE65 gene mutations using AAV2. However, newer modified and more efficient capsids are increasingly being needed.

The engineering of novel AAV capsids to gain new properties and characteristics has been a constant pursuit. A major limitation to rational design approaches is related to insufficient knowledge pertaining to AAV cell surface binding, internalization, trafficking, uncoating and gene expression.

Several modified AAV capsids have been developed (see, e.g., WO2012145601A2, WO2016134375A1 and WO2018022905A2), however, there is still a need of developing novel modified AAV capsids to improve the gene therapy for ocular diseases, such as a gene therapy for the in situ delivery of a polynucleotide encoding a product for treating the diseases.

SUMMARY

In the first aspect, the present invention provides a modified AAV capsid polypeptide comprising, as compared to the parental AAV capsid polypeptide, a peptide inserted into loop IV, and wherein the inserted peptide comprises an amino acid sequence shown in Formula I:

$$\text{spacer1-}X1\text{-}X2\text{-}X3\text{-}X_4\text{-}X5\text{-}X6\text{-}X7\text{-spacer2} \quad \text{(I)},$$

wherein

X1 is selected from G, L and N;
X2 is selected from K, A, G and S;
X3 is selected from G, E and P;
X4 is selected from P and T;
X5 is selected from T, S and G;
X6 is selected from T, R and K; and
X7 is selected from K, P and N.

The present invention further provides a polynucleotide encoding the modified AAV capsid polypeptide of the present invention, a vector comprising the polynucleotide, and a host cell comprising the polynucleotide, or the vector.

In the second aspect, the present invention provides a system or a kit for packaging an rAAV comprising the polynucleotide, the vector, or the host cell of the present invention.

In the third aspect, the present invention provides a recombinant adeno-associated virus (rAAV) comprising the modified AAV capsid polypeptide of the present invention and a genome encoding a gene product.

In the fourth aspect, the present invention provides a pharmaceutical composition comprising the rAAV of the present invention.

The present invention provides a method of treating a retinal disease comprising the administration of the rAAV or the pharmaceutical composition of the present invention to an eye of a subject in need thereof.

Provided are the rAAV or the pharmaceutical composition the present invention for use in the treatment of a retinal disease.

The present invention provides use of the rAAV or the pharmaceutical composition of the present invention in the preparation of a medicament for treating a retinal disease.

DETAILED DESCRIPTION OF THE INVENTION

1. Definition

Figure 1A:
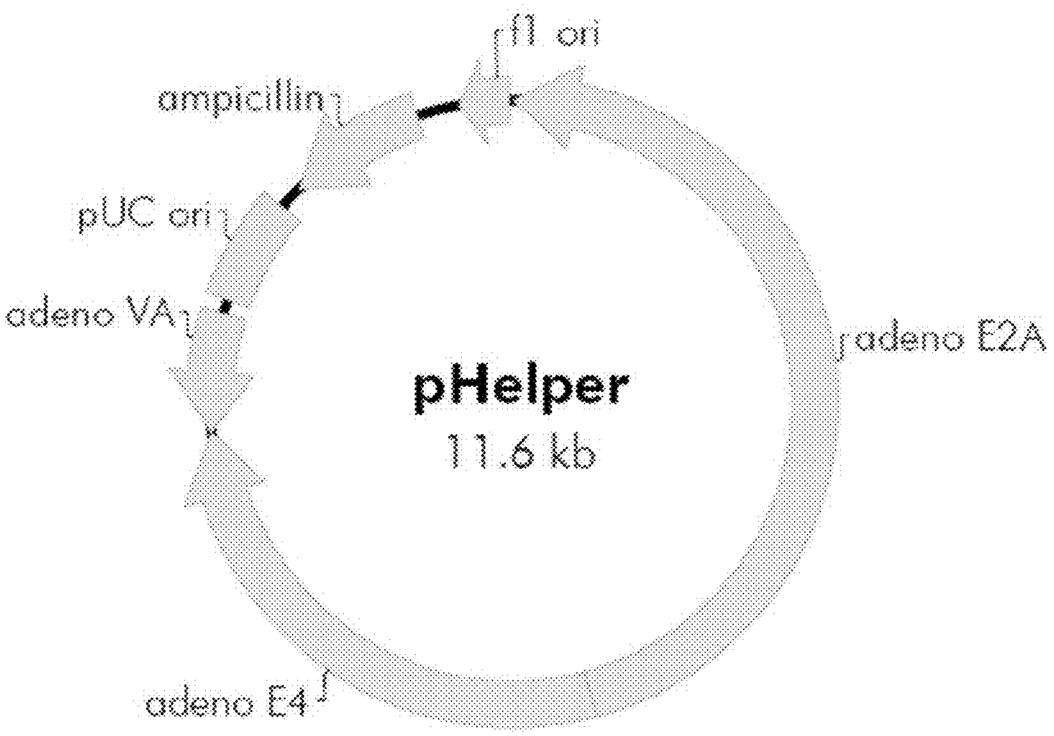
FIGS. 1A-1D shows the maps of helper plasmid (FIG. 1A), the packaging plasmid (FIG. 1B) and transgene plasmid (FIGS. 1C and 1D) for preparing the rAAVs.

Unless otherwise indicated, all terms used herein have the same meaning as they would to one skilled in the art, and the practice of the present invention will employ conventional techniques of microbiology and recombinant DNA technology, which are within the knowledge of those of skill in the art.

The term "retinal cell" can refer herein to any of the cell types comprised in the retina, such as retinal ganglion cells, amacrine cells, horizontal cells, bipolar cells, and photoreceptor cells including rods and cones, Muller glial cells, and retinal pigmented epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in public databases such as GenBank. See, e.g., GenBank Accession Numbers NC_002077 (AAV-1), AF063497 (AAV-1), NC_001401 (AAV-2), AF043303 (AAV-2), NC_001729 (AAV-3), NC_001829 (AAV-4), U89790 (AAV-4), NC_006152 (AAV-5), AF513851 (AAV-7), AF513852 (AAV-8), and NC_006261 (AAV-8); the disclosures of which are incorporated by reference herein for teaching AAV nucleic acid and amino acid sequences.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids (also referred to as transgene plasmid). An rAAV vector may either be single-stranded (ssAAV) or self-complementary (scAAV).

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes". A plasmid or other expression vector comprising rep and cap genes is referred herein to as "packaging plasmid" or "packaging vector".

The cap gene encodes three structural proteins, VP1, VP2, and VP3, that self-assemble into a 60-mer icosahedral capsid at a ratio of approximately 1:1:10. These three proteins are transcribed from the same open reading frame and share a C-terminal domain but have different N-termini due to alternative start codons and alternative splicing (Esther J. Lee, et al., Adeno-Associated Virus (AAV) Vectors: Rational Design Strategies for Capsid Engineering, *Curr Opin Biomed Eng.* 2018; 7:58-63). For example, the wildtype AAV2 capsid may comprise VP1 of SEQ ID NO: 1, VP2 of amino acids 138-735 of SEQ ID NO: 1, and VP3 of amino acids 203-735 of SEQ ID NO: 1.

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid, which is referred herein to as "helper plasmid", or other expression vector comprising nucleotide sequences encoding one or more adenoviral proteins is transfected into a producer cell along with an rAAV vector.

As used herein, the term "polynucleotide construct" refers to a single-stranded or double-stranded polynucleotide, which is isolated from a naturally occurring gene or modified to contain a nucleic acid segment that does not naturally occur. When the polynucleotide construct contains the control sequences required to express the coding sequence of the present invention, the polynucleotide construct comprises an "expression cassette".

As used herein, the term "polynucleotide" usually refers to generally a nucleic acid molecule (e.g., 100 bases and up to 30 kilobases in length) and a sequence that is either complementary (antisense) or identical (sense) to the sequence of a messenger RNA (mRNA) or miRNA fragment or molecule. The term can also refer to DNA or RNA molecules that are either transcribed or non-transcribed.

The term "exogenous polynucleotide" refers to a nucleotide sequence that does not originate from the host in which it is placed. It may be identical to the host's DNA or heterologous. An example is a sequence of interest inserted into a vector. Such exogenous DNA sequences may be derived from a variety of sources including DNA, cDNA, synthetic DNA, and RNA. Exogenous polynucleotides also encompass DNA sequences that encode antisense oligonucleotides.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc.

As used herein, the term "expression cassette" refers to a polynucleotide segment comprising a polynucleotide encoding a polypeptide operably linked to additional nucleotides provided for the expression of the polynucleotide, for example, control sequence.

As used herein, the term "expression" includes any step involved in the production of a polypeptide, including but not limited to transcription, post-transcriptional modification, translation, post-translational modification, and secretion.

A "control sequence" includes all elements necessary or beneficial for the expression of the polynucleotide encoding the polypeptide of the present invention. Each control sequence may be natural or foreign to the nucleotide sequence encoding the polypeptide, or natural or foreign to each other. Such control sequences include, but are not limited to, leader sequence, polyadenylation sequence, propeptide sequence, promoter, enhancer, signal peptide sequence, and transcription terminator. At a minimum, control sequences include a promoter and signals for the termination of transcription and translation.

For example, the control sequence may be a suitable promoter sequence, a nucleotide sequence recognized by the host cell to express the polynucleotide encoding the polypeptide of the present invention. The promoter sequence contains a transcription control sequence that mediates the expression of the polypeptide. The promoter may be any nucleotide sequence that exhibits transcriptional activity in the selected host cell, for example, lac operon of *E. coli*. The promoters also include mutant, truncated and hybrid promoters, and can be obtained from genes encoding extracellular or intracellular polypeptides, which are homologous or heterologous to the host cell.

As used herein, the term "operably linked" herein refers to a configuration in which a control sequence is placed at an appropriate position relative to the coding sequence of the polynucleotide sequence, whereby the control sequence directs the expression of the polypeptide coding sequence.

A "gene" refers to a polynucleotide containing at least one open reading frame encoding a polynucleotide or a polypeptide.

A "gene product" is a molecule resulting from the expression of a particular gene. Gene products include, e.g., a polypeptide, an aptamer, an interfering RNA, an mRNA, and the like.

A "small interfering RNA" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

A "short hairpin RNA," or shRNA, is a polynucleotide construct that can be made to express an interfering RNA such as siRNA.

The term "recombinant" as used herein refers to nucleic acids, vectors, polypeptides, or proteins that have been generated using DNA recombination (cloning) methods and are distinguishable from native or wild-type nucleic acids, vectors, polypeptides, or proteins. The terms "polypeptide" and "protein" are used interchangeably herein and refer to a polymer of amino acids and includes full-length proteins and fragments thereof.

As used herein, the term "host cell" refers to, for example microorganisms, yeast cells, insect cells, and mammalian cells, that can be, or have been, used as recipients of rAAV vectors. The term includes the progeny of the original cell which has been transduced. Thus, a "host cell" as used herein generally refers to a cell which has been transduced with an exogenous DNA sequence. It is understood that the progeny of a single parental cell may not necessarily be completely identical in morphology or in genomic or total DNA complement to the original parent, due to natural, accidental, or deliberate mutation.

The term "pharmaceutically acceptable" as used herein refers to molecular entities and compositions that are physiologically tolerable and do not typically produce toxicity or an allergic or similar untoward reaction, such as gastric upset, dizziness and the like, when administered to a human.

The term "subject" as used herein includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector.

Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

As used herein, the term "ED50" means median effective dose of an agent, i.e., the dose capable of resulting in 50% of max response. For delivering a transgene to be expressed into a cell with a recombinant virus (such as rAAV), the ED50 can be expressed as the MOI, at which 50% of the max expression of the transgene is achieved.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a", "an", and "the" include plural referents unless the context clearly dictates otherwise. Thus, for example, reference to "a modified AAV capsid" includes a plurality of such capsids. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

2. Modified AAV Capsid Polypeptides and the Coding Polynucleotides

The present invention provides a modified AAV capsid polypeptide comprising, as compared to the parental AAV capsid polypeptide, a peptide inserted in loop IV, wherein the inserted peptide comprises an amino acid sequence shown in Formula I:

spacer1-*X*1-*X*2-*X*3-*X*4-*X*5-*X*6-*X*7-spacer2 (I), wherein
X1 is selected from G, L and N;
X2 is selected from K, A, G and S;
X3 is selected from G, E and P;
X4 is selected from P and T;
X5 is selected from T, S and G;
X6 is selected from T, R and K; and
X7 is selected from K, P and N.

In some embodiments, the spacer 1 and spacer 2 independently comprise one or more amino acids. In some embodiments, the spacer 1 and spacer 2 independently comprise one to ten amino acids. In some embodiments, the spacer 1 and spacer 2 independently comprise 1, 2, 3, 4, 5, 6, 7, 8, 9 or 10 amino acids. In some embodiments, the spacer 1 and spacer 2 independently comprise one to three amino acids. In some embodiments, the spacer 1 and spacer 2 independently consist of one to three amino acids.

In some embodiments, the inserted peptide consists of an amino acid sequence shown in Formula I:

spacer1-*X*1-*X*2-*X*3-*X*4-*X*5-*X*6-*X*7-spacer2 (I), wherein
X1 is selected from G, L and N;
X2 is selected from K, A, G and S;
X3 is selected from G, E and P;
X4 is selected from P and T;
X5 is selected from T, S and G;
X6 is selected from T, R and K;
X7 is selected from K, P and N; and
the spacer 1 and spacer 2 independently comprise one or more amino acids selected from A, L and G.

In some embodiments, the inserted peptide consists of an amino acid sequence shown in Formula I:

spacer1-*X*1-*X*2-*X*3-*X*4-*X*5-*X*6-*X*7-spacer2 (I), wherein
X1 is selected from G, L and N;
X2 is selected from K, A, G and S;
X3 is selected from G, E and P;
X4 is selected from P and T;
X5 is selected from T, S and G;
X6 is selected from T, R and K;
X7 is selected from K, P and N; and
the spacer 1 and spacer 2 independently comprise one to ten amino acids selected from A, L and G.

In some embodiments, the inserted peptide consists of an amino acid sequence shown in Formula I:

spacer1-*X*1-*X*2-*X*3-*X*4-*X*5-*X*6-*X*7-spacer2 (I), wherein
X1 is selected from G, L and N;
X2 is selected from K, A, G and S;
X3 is selected from G, E and P;
X4 is selected from P and T;
X5 is selected from T, S and G;
X6 is selected from T, R and K;
X7 is selected from K, P and N; and
the spacer 1 and spacer 2 independently comprise one to three amino acids selected from A, L and G.

In some embodiments, X1-X2-X3-$X_4$-X5-X6-X7 is an amino acid sequence selected from SEQ ID NOs: 6 (GKGPTTK), SEQ ID NO: 7 (LAEPSRP), SEQ ID NO: 8 (LGPPSKP) and SEQ ID NO: 9 (NSPTGRN).

In some embodiments, the inserted peptide comprises an amino acid sequence shown in Formula II:

Y1-Y2-Y3-X1-X2-X3-X4-X5-X6-X7-Y4-Y5 (II), wherein spacer 1 consists of amino acids Y1, Y2 andY3, spacer 2 consists of amino acids Y4 and Y5; X1 is selected from G, L and N; X2 is selected from K, A, G and S; X3 is selected from G, E and P; X4 is selected from P and T; X5 is selected from T, S and G; X6 is selected from T, R and K; X7 is selected from K, P and N.

In some embodiments, the inserted peptide comprises an amino acid sequence of Y1-Y2-Y3-SEQ ID NO: 6 (GKGPTTK)-Y4-Y5, wherein each of Y1-Y5 is independently selected from A, L and G. In some embodiments, the inserted peptide comprises an amino acid sequence of Y1-Y2-Y3-SEQ ID NO: 7 (LAEPSRP)-Y4-Y5, wherein each of Y1-Y5 is independently selected from A, L and G. In some embodiments, the inserted peptide comprises an amino acid sequence of Y1-Y2-Y3-SEQ ID NO: 8 (LGPPSKP)-Y4-Y5, wherein each of Y1-Y5 is independently selected from A, L and G. In some embodiments, the inserted peptide comprises an amino acid sequence of Y1-Y2-Y3-SEQ ID NO: 9 (NSPTGRN)-Y4-Y5, wherein each of Y1-Y5 is independently selected from A, L and G.

In some embodiments, the inserted peptide comprises an amino acid sequence of Y1-Y2-Y3-SEQ ID NO: 6 (GKGPTTK)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 7 (LAEPSRP)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 8 (LGPPSKP)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 9 (NSPTGRN)-Y4-Y5, wherein Y1 is A, Y2 is A or L, Y3 is A or G, Y4 is A, and Y5 is A.

In some embodiments, the inserted peptide comprises an amino acid sequence selected from SEQ ID NOs: 10, 11, 12 and 13.

In some embodiments, the inserted peptide consists of an amino acid sequence shown in Formula II:

Y1-Y2-Y3-X1-X2-X3-X4-X5-X6-X7-Y4-Y5 (II), wherein spacer 1 consists of amino acids Y1, Y2 andY3, spacer 2 consists of amino acids Y4 and Y5; X1 is selected from G, L and N; X2 is selected from K, A, G and S; X3 is selected from G, E and P; X4 is selected from P and T; X5 is selected from T, S and G; X6 is selected from T, R and K; X7 is selected from K, P and N.

In some embodiments, the inserted peptide consists of an amino acid sequence of Y1-Y2-Y3-SEQ ID NO: 6 (GKGPTTK)-Y4-Y5, wherein each of Y1-Y5, if present, is independently selected from A, L and G. In some embodiments, the inserted peptide consists of an amino acid sequence of Y1-Y2-Y3-SEQ ID NO: 7 (LAEPSRP)-Y4-Y5, wherein each of Y1-Y5, if present, is independently selected from A, L and G. In some embodiments, the inserted peptide consists of an amino acid sequence of Y1-Y2-Y3-SEQ ID NO: 8 (LGPPSKP)-Y4-Y5, wherein each of Y1-Y5, if present, is independently selected from A, L and G. In some embodiments, the inserted peptide consists of an amino acid sequence of Y1-Y2-Y3-SEQ ID NO: 9 (NSPTGRN)-Y4-Y5, wherein each of Y1-Y5, if present, is independently selected from A, L and G.

In some embodiments, the inserted peptide consists of an amino acid sequence of Y1-Y2-Y3-SEQ ID NO: 6 (GKGPTTK)-Y4-Y5, wherein each of Y1-Y5 is independently selected from A, L and G. In some embodiments, the inserted peptide consists of an amino acid sequence of Y1-Y2-Y3-SEQ ID NO: 7 (LAEPSRP)-Y4-Y5, wherein each of Y1-Y5 is independently selected from A, L and G. In some embodiments, the inserted peptide consists of an amino acid sequence of Y1-Y2-Y3-SEQ ID NO: 8 (LGPPSKP)-Y4-Y5, wherein each of Y1-Y5 is independently selected from A, L and G. In some embodiments, the inserted peptide consists of an amino acid sequence of Y1-Y2-Y3-SEQ ID NO: 9 (NSPTGRN)-Y4-Y5, wherein each of Y1-Y5 is independently selected from A, L and G.

In some embodiments, the inserted peptide consists of an amino acid sequence of Y1-Y2-Y3-SEQ ID NO: 6 (GKGPTTK)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 7 (LAEPSRP)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 8 (LGPPSKP)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 9 (NSPTGRN)-Y4-Y5, wherein Y1 is A, Y2 is A or L, Y3 is A or G, Y4 is A, and Y5 is A.

In some embodiments, the inserted peptide consists of an amino acid sequence selected from SEQ ID NOs: 10, 11, 12 and 13.

In some embodiments, the parental AAV capsid polypeptide is an AAV2 capsid polypeptide VP1, VP2 or VP3. In some embodiments, the parental AAV capsid polypeptide is an AAV2 capsid polypeptide comprising the amino acid sequence of SEQ ID NO: 1, amino acids 138-735 of SEQ ID NO: 1, or amino acids 203-735 of SEQ ID NO: 1 or a variant thereof. In some embodiment, the variant is at least 80%, 85%, 90%, 95%, 96%, 97%, 98%, 99%, 99.5%, 99.6%, 99.7% or 99.8% identical to SEQ ID NO: 1 over the full length, amino acids 138-735, or amino acids 203-735. In some embodiments, the variant comprises, as compared to SEQ ID NO: 1, insertion, deletion, substitution and/or addition of 1, 2, 3, 4, 5, 6, 7, 8, 9, 10 or more amino acids. Preferably, the insertion of the amino acids is conducted at a site different from the inserted peptide of the present invention, more preferably not in loop IV. Preferably, the substitution of amino acid is a conserved substitution. In some embodiments, the parental AAV capsid polypeptide consists of the amino acid sequence of SEQ ID NO: 1, amino acids 138-735 of SEQ ID NO: 1, or amino acids 203-735 of SEQ ID NO: 1.

For AAV2 capsid polypeptides, loop IV corresponds to positions 570-611 of SEQ ID NO: 1 Therefore, in other words, the modified AAV capsid polypeptide comprises, as compared to the parental AAV capsid polypeptide, a peptide as defined above inserted in the region corresponding to positions 570-611 of SEQ ID NO: 1. In some embodiments, the peptide is inserted between positions in the parental capsid polypeptide corresponding to positions 587 and 588 of SEQ ID NO: 1.

In some embodiments, the modified AAV capsid polypeptide of the invention comprises an amino acid sequence selected from SEQ ID NO: 2, 3, 4 and 5, amino acids 138-747 of SEQ ID NO: 2, 3, 4 or 5, or amino acids 203-747 of SEQ ID NO: 2, 3, 4 or 5. In some embodiments, the modified AAV capsid polypeptide of the invention consists of an amino acid sequence selected from SEQ ID NO: 2, 3, 4 and 5, amino acids 138-747 of SEQ ID NO: 2, 3, 4 or 5, or amino acids 203-747 of SEQ ID NO: 2, 3, 4 or 5. In some embodiments, the modified AAV capsid polypeptide comprises or consists of a variant of SEQ ID NO: 2, 3, 4 or 5. In some embodiments, the variant is at least 80%, 85%, 90%, 95%, 96%, 97%, 98%, 99%, 99.5%, 99.6%, 99.7% or 99.8% identical to SEQ ID NO: 2, 3, 4 or 5 over the full length, amino acids 138-747 of SEQ ID NO: 2, 3, 4 or 5, or amino acids 203-747 of SEQ ID NO: 2, 3, 4 or 5. In some embodiments, the variant comprises, as compared to SEQ ID NO: 2, 3, 4 or 5, insertion, deletion, substitution and/or addition of 1, 2, 3, 4, 5, 6, 7, 8, 9, 10 or more amino acids. Preferably, the insertion of the amino acids is conducted at a site different from the inserted peptide of the present invention (SEQ ID NOs: 10, 11, 12 and 13), more preferably not in loop IV. Preferably, the substitution of amino acid is a conserved substitution.

In some embodiments, the modified AAV capsid polypeptide is encoded by a nucleotide sequence selected from SEQ ID NOs: 14, 15, 16 and 17. In some embodiments, the modified AAV capsid polypeptide is encoded by a variant of SEQ ID NO: 14, 15, 16 or 17. In some embodiments, the variant is at least 80%, 85%, 90%, 95%, 96%, 97%, 98%, 99%, 99.5%, 99.6%, 99.7% or 99.8% identical to SEQ ID NO: 14, 15, 16 or 17. In some embodiments, the variant comprises, as compared to SEQ ID NO: 14, 15, 16 or 17, substitution and/or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. In some embodiments, the variant comprises, as compared to SEQ ID NO: 14, 15, 16 or 17, insertion and/or deletion of 3n (n is an integer, which is 1, 2, 3, 4, 5, 6, 7, 8, 9, 10 or more) nucleotides. Preferably, the insertion of the nucleotides is conducted at a site different from the nucleotide sequence encoding the inserted peptide of the present invention (SEQ ID NOs: 10, 11, 12 and 13), more preferably not in the nucleotide sequence encoding loop IV. Preferably, the variant is a degenerate variant, or the substitutions of nucleotides result in conserved substitutions of amino acids.

The present invention further provides a polynucleotide encoding the modified AAV capsid polypeptide of the present invention.

In some embodiments, the polynucleotide comprises a nucleotide sequence selected from SEQ ID NOs: 14, 15, 16 and 17. In some embodiments, the polynucleotide consists of a nucleotide sequence selected from SEQ ID NOs: 14, 15, 16 and 17. In some embodiments, the polynucleotide comprises a nucleotide sequence at least 80%, 85%, 90%, 95%, 96%, 97%, 98%, 99%, 99.5%, 99.6%, 99.7% or 99.8% identical to SEQ ID NO: 14, 15, 16 or 17. In some embodiments, the polynucleotide consists of a nucleotide sequence at least 80%, 85%, 90%, 95%, 96%, 97%, 98%, 99%, 99.5%, 99.6%, 99.7% or 99.8% identical to SEQ ID NO: 14, 15, 16 or 17. In some embodiments, the nucleotide sequence comprises, as compared to SEQ ID NO: 14, 15, 16 or 17, substitution and/or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. In some embodiments, the nucleotide sequence comprises, as compared to SEQ ID NO: 14, 15, 16 or 17, insertion and/or deletion of 3n (n is an integer, which is 1, 2, 3, 4, 5, 6, 7, 8, 9, 10 or more) nucleotides. Preferably, the insertion of the nucleotides is conducted at a site different from the nucleotide sequence encoding the inserted peptide of the present invention (SEQ ID NOs: 10, 11, 12 and 13), more preferably not in the nucleotide sequence encoding loop IV. Preferably, the polynucleotide comprises a degenerate variant of SEQ ID NO: 14, 15, 16 or 17, or the substitutions of nucleotides result in conserved substitutions of amino acids. Preferably, the polynucleotide consists of a degenerate variant of SEQ ID NO: 14, 15, 16 or 17, or the substitutions of nucleotides result in conserved substitutions of amino acids.

The present invention provides a vector comprising the polynucleotide of the present invention, and a host cell comprising the polynucleotide or the vector of the present invention.

The modified AAV capsid polypeptide of the present invention allows for an improved transduction of an AAV in an eye, especially, into a retinal cell as compared to the parental AAV capsid polypeptide.

3. Packaging of the rAAV

It is known in the art to package rAAV with a system comprising three plasmids, including i) a transgene plasmid comprising the genome of the rAAV encoding a desired gene product, ii) a packaging plasmid encoding the REP and/or CAP proteins, and iii) a helper plasmid (see, e.g., Crosson S M et al., Helper-free Production of Laboratory Grade AAV and Purification by Iodixanol Density Gradient Centrifugation. Mol Ther Methods Clin Dev. 2018; 10:1-7). A method of producing rAAV is also described in, for example, U.S. Patent Publication No. 2005/0053922 and U.S. Patent Publication No. 2009/0202490.

The present invention provides a method for packaging the rAAV of the present invention, comprising introducing the polynucleotide or the vector of the present invention into a host cell.

In some embodiments, the vector is an expression vector, in which the polynucleotide of the present invention is operably linked to a promoter. In some embodiments, the vector of the present invention further comprises a rep gene operably linked to a promoter.

In some embodiments, the host cell further comprises a helper plasmid, and/or a rAAV vector. When the host cell of the present invention is used to generate the rAAV of the present invention, it is referred to as a "packaging cell".

The polynucleotide or the vector of the present invention can be introduced into the host cell stably or transiently using defined techniques including, but not limited to, electroporation, calcium phosphate precipitation, liposome-mediated transfection, and the like. For stable transformation, the subject nucleic acid will typically be operably linked to a selectable marker, such as neomycin resistance gene and the like.

The host cell is a variety of cells, such as mammalian cells, including, for example, murine cells and primate cells (e.g., human cells). Suitable mammalian cells include, but are not limited to, primary cells and cell lines, wherein suitable cell lines include, but are not limited to, 293 cells, COS cells, HeLa cells, Vero cells, 3T3 mouse fibroblasts, C3H10T1/2 fibroblasts, CHO cells, etc. Non-limiting examples of suitable host cells include, for example, HeLa cells (e.g., American Type Culture Collection (ATCC) No. CCL-2), CHO cells (e.g., ATCC No. CRL9618, CCL61, CRL9096), 293 cells (e.g., ATCC No. CRL-1573), Vero cells, NIH3T3 cells (eg, ATCC No. CRL-1658), Huh-7 cells, BHK cells (e.g., ATCC No. CCL10), PC12 cells (ATCC No. CRL1721) COS cells, COS-7 cells (ATCC No. CRL1651), RATI cells, mouse L cells (ATCC No. CCLI.3), human embryonic kidney (HEK) cells (ATCC No. CRL1573), HLHepG2 cells, and the like. Bacterial cells, such as Sf9 cells, which produce AAV, can also be used to prepare the host cell of the present invention (see, for example, U.S. Pat. No. 7,271,002; U.S. patenttent Publication Ser. No. 12/297,958).

The present invention provides a system or a kit for packaging an rAAV comprising the polynucleotide, the vector, or the host cell of the present invention. In some embodiments, the system or kit further comprises a helper plasmid, and/or a rAAV vector.

4. Recombinant AAV

The present invention provides a recombinant adeno-associated virus (rAAV) comprising a modified AAV capsid polypeptide and a genome encoding a gene product, wherein the modified AAV capsid polypeptides comprise, as compared to the parental AAV capsid polypeptides, a peptide inserted into loop IV, and wherein the inserted peptide comprises an amino acid sequence shown in Formula I:

spacer1-*X*1-*X*2-*X*3-*X*4-*X*5-*X*6-*X*7-spacer2 (I), wherein

X1 is selected from G, L and N;
X2 is selected from K, A, G and S;
X3 is selected from G, E and P;
X4 is selected from P and T;
X5 is selected from T, S and G;
X6 is selected from T, R and K; and
X7 is selected from K, P and N.

In some embodiments, the spacer 1 and spacer 2 independently comprise one or more amino acids. In some embodiments, the spacer 1 and spacer 2 independently comprise one to ten amino acids. In some embodiments, the spacer 1 and spacer 2 independently comprise 1, 2, 3, 4, 5, 6, 7, 8, 9 or 10 amino acids. In some embodiments, the spacer 1 and spacer 2 independently comprise one to three amino acids. In some embodiments, the spacer 1 and spacer 2 independently consist of one to three amino acids.

In some embodiments, the inserted peptide consists of an amino acid sequence shown in Formula I:

spacer1-*X*1-*X*2-*X*3-*X*4-*X*5-*X*6-*X*7-spacer2 (I), wherein

X1 is selected from G, L and N;
X2 is selected from K, A, G and S;
X3 is selected from G, E and P;
X4 is selected from P and T;
X5 is selected from T, S and G;
X6 is selected from T, R and K;
X7 is selected from K, P and N; and
the spacer 1 and spacer 2 independently comprise one or more amino acids selected from A, L and G.

In some embodiments, the inserted peptide consists of an amino acid sequence shown in Formula I:

spacer1-*X*1-*X*2-*X*3-*X*4-*X*5-*X*6-*X*7-spacer2 (I), wherein

X1 is selected from G, L and N;
X2 is selected from K, A, G and S;
X3 is selected from G, E and P;
X4 is selected from P and T;

X5 is selected from T, S and G;
X6 is selected from T, R and K;
X7 is selected from K, P and N; and
the spacer 1 and spacer 2 independently comprise one to ten amino acids selected from A, L and G.

In some embodiments, the inserted peptide consists of an amino acid sequence shown in Formula I:

spacer1-X1-X2-X3-X4-X5-X6-X7-spacer2 (I), wherein
X1 is selected from G, L and N;
X2 is selected from K, A, G and S;
X3 is selected from G, E and P;
X4 is selected from P and T;
X5 is selected from T, S and G;
X6 is selected from T, R and K;
X7 is selected from K, P and N; and
the spacer 1 and spacer 2 independently comprise one to three amino acids selected from A, L and G.

In some embodiments, X1-X2-X3-X4-X5-X6-X7 is an amino acid sequence selected from SEQ ID NOs: 6 (GKGPTTK), SEQ ID NO: 7 (LAEPSRP), SEQ ID NO: 8 (LGPPSKP) and SEQ ID NO: 9 (NSPTGRN)

In some embodiments, the inserted peptide comprises an amino acid sequence shown in Formula II:

Y1-Y2-Y3-X1-X2-X3-X4-X5-X6-X7-Y4-Y5 (II), wherein spacer 1 consists of amino acids Y1, Y2 andY3, spacer 2 consists of amino acids Y4 and Y5; X1 is selected from G, L and N; X2 is selected from K, A, G and S; X3 is selected from G, E and P; X4 is selected from P and T; X5 is selected from T, S and G; X6 is selected from T, R and K; X7 is selected from K, P and N.

In some embodiments, the inserted peptide comprises an amino acid sequence of Y1-Y2-Y3-SEQ ID NO: 6 (GKGPTTK)-Y4-Y5, wherein each of Y1-Y5, if present, is independently selected from A, L and G. In some embodiments, the inserted peptide comprises an amino acid sequence of Y1-Y2-Y3-SEQ ID NO: 7 (LAEPSRP)-Y4-Y5, wherein each of Y1-Y5, if present, is independently selected from A, L and G. In some embodiments, the inserted peptide comprises an amino acid sequence of Y1-Y2-Y3-SEQ ID NO: 8 (LGPPSKP)-Y4-Y5, wherein each of Y1-Y5, if present, is independently selected from A, L and G. In some embodiments, the inserted peptide comprises an amino acid sequence of Y1-Y2-Y3-SEQ ID NO: 9 (NSPTGRN)-Y4-Y5, wherein each of Y1-Y5, if present, is independently selected from A, L and G.

In some embodiments, the inserted peptide comprises an amino acid sequence of Y1-Y2-Y3-SEQ ID NO: 6 (GKGPTTK)-Y4-Y5, wherein each of Y1-Y5 is independently selected from A, L and G. In some embodiments, the inserted peptide comprises an amino acid sequence of Y1-Y2-Y3-SEQ ID NO: 7 (LAEPSRP)-Y4-Y5, wherein each of Y1-Y5 is independently selected from A, L and G. In some embodiments, the inserted peptide comprises an amino acid sequence of Y1-Y2-Y3-SEQ ID NO: 8 (LGPPSKP)-Y4-Y5, wherein each of Y1-Y5 is independently selected from A, L and G. In some embodiments, the inserted peptide comprises an amino acid sequence of Y1-Y2-Y3-SEQ ID NO: 9 (NSPTGRN)-Y4-Y5, wherein each of Y1-Y5 is independently selected from A, L and G.

In some embodiments, the inserted peptide comprises an amino acid sequence of Y1-Y2-Y3-SEQ ID NO: 6 (GKGPTTK)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 7 (LAEPSRP)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 8 (LGPPSKP)-Y4-Y5, wherein Y1 is A, Y2 is A or L, Y3 is A or G, Y4 is A, and Y5 is A. In some embodiments, the inserted peptide comprises an amino acid sequence of Y1-Y2-Y3-SEQ ID NO: 9 (NSPTGRN)-Y4-Y5, wherein Y1 is A, Y2 is A or L, Y3 is A or G, Y4 is A, and Y5 is A.

In some embodiments, wherein the inserted peptide comprises an amino acid sequence selected from SEQ ID NO: 10 (AAAGKGPTTKAA), SEQ ID NO: 11 (AAALAEPSRPAA), SEQ ID NO: 12 (ALALGPPSKPAA) and SEQ ID NO: 13 (AAGNSPTGRNAA).

In some embodiments, the inserted peptide consists of an amino acid sequence shown in Formula II:

Y1-Y2-Y3-X1-X2-X3-X4-X5-X6-X7-Y4-Y5 (II), wherein spacer 1 consists of amino acids Y1, Y2 andY3, spacer 2 consists of amino acids Y4 and Y5; X1 is selected from G, L and N; X2 is selected from K, A, G and S; X3 is selected from G, E and P; X4 is selected from P and T; X5 is selected from T, S and G; X6 is selected from T, R and K; X7 is selected from K, P and N.

In some embodiments, the inserted peptide consists of an amino acid sequence of Y1-Y2-Y3-SEQ ID NO: 6 (GKGPTTK)-Y4-Y5, wherein each of Y1-Y5, if present, is independently selected from A, L and G. In some embodiments, the inserted peptide consists of an amino acid sequence of Y1-Y2-Y3-SEQ ID NO: 7 (LAEPSRP)-Y4-Y5, wherein each of Y1-Y5, if present, is independently selected from A, L and G. In some embodiments, the inserted peptide consists of an amino acid sequence of Y1-Y2-Y3-SEQ ID NO: 8 (LGPPSKP)-Y4-Y5, wherein each of Y1-Y5, if present, is independently selected from A, L and G. In some embodiments, the inserted peptide consists of an amino acid sequence of Y1-Y2-Y3-SEQ ID NO: 9 (NSPTGRN)-Y4-Y5, wherein each of Y1-Y5, if present, is independently selected from A, L and G.

In some embodiments, the inserted peptide consists of an amino acid sequence of Y1-Y2-Y3-SEQ ID NO: 6 (GKGPTTK)-Y4-Y5, wherein each of Y1-Y5 is independently selected from A, L and G. In some embodiments, the inserted peptide consists of an amino acid sequence of Y1-Y2-Y3-SEQ ID NO: 7 (LAEPSRP)-Y4-Y5, wherein each of Y1-Y5 is independently selected from A, L and G. In some embodiments, the inserted peptide consists of an amino acid sequence of Y1-Y2-Y3-SEQ ID NO: 8 (LGPPSKP)-Y4-Y5, wherein each of Y1-Y5 is independently selected from A, L and G. In some embodiments, the inserted peptide consists of an amino acid sequence of Y1-Y2-Y3-SEQ ID NO: 9 (NSPTGRN)-Y4-Y5, wherein each of Y1-Y5 is independently selected from A, L and G.

In some embodiments, the inserted peptide consists of an amino acid sequence of Y1-Y2-Y3-SEQ ID NO: 6 (GKGPTTK)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 7 (LAEPSRP)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 8 (LGPPSKP)-Y4-Y5, wherein Y1 is A, Y2 is A or L, Y3 is A or G, Y4 is A, and Y5 is A. In some embodiments, the inserted peptide consists of an amino acid sequence of Y1-Y2-Y3-SEQ ID NO: 9 (NSPTGRN)-Y4-Y5, wherein Y1 is A, Y2 is A or L, Y3 is A or G, Y4 is A, and Y5 is A.

In some embodiments, wherein the inserted peptide consists of an amino acid sequence selected from SEQ ID NO: 10 (AAAGKGPTTKAA), SEQ ID NO: 11 (AAALAEPSR-PAA), SEQ ID NO: 12 (ALALGPPSKPAA) and SEQ ID NO: 13 (AAGNSPTGRNAA).

In some embodiments, the parental AAV capsid polypeptide is an AAV2 capsid polypeptide VP1, VP2 or VP3. In some embodiments, the parental AAV capsid polypeptide is an AAV2 capsid polypeptide comprising the amino acid sequence of SEQ ID NO: 1, amino acids 138-735 of SEQ ID NO: 1, or amino acids 203-735 of SEQ ID NO: 1 or a variant thereof. In some embodiment, the variant is at least 80%, 85%, 90%, 95%, 96%, 97%, 98%, 99%, 99.5%, 99.6%, 99.7% or 99.8% identical to SEQ ID NO: 1 over the full length, amino acids 138-735, or amino acids 203-735. In some embodiments, the variant comprises, as compared to SEQ ID NO: 1, insertion, deletion, substitution and/or addition of 1, 2, 3, 4, 5, 6, 7, 8, 9, 10 or more amino acids. Preferably, the insertion of the amino acids is conducted at a site different from the inserted peptide of the present invention, more preferably not in loop IV. Preferably, the substitution of amino acid is a conserved substitution. In some embodiments, the parental AAV capsid polypeptide consists of the amino acid sequence of SEQ ID NO: 1, amino acids 138-735 of SEQ ID NO: 1, or amino acids 203-735 of SEQ ID NO: 1.

In some embodiments, the modified AAV capsid polypeptide comprises, as compared to the parental AAV capsid polypeptide, a peptide as defined above inserted in the region corresponding to positions 570-611 of SEQ ID NO: 1. In some embodiments, the peptide is inserted between positions in the parental capsid polypeptide corresponding to positions 587 and 588 of SEQ ID NO: 1.

In some embodiments, the modified AAV capsid polypeptide of the invention comprises an amino acid sequence selected from SEQ ID NO: 2, 3, 4 and 5, amino acids 138-747 of SEQ ID NO: 2, 3, 4 or 5, or amino acids 203-747 of SEQ ID NO: 2, 3, 4 or 5. In some embodiments, the modified AAV capsid polypeptide of the invention consists of an amino acid sequence selected from SEQ ID NO: 2, 3, 4 and 5, amino acids 138-747 of SEQ ID NO: 2, 3, 4 or 5, or amino acids 203-747 of SEQ ID NO: 2, 3, 4 or 5. In some embodiments, the modified AAV capsid polypeptide comprises or consists of a variant of SEQ ID NO: 2, 3, 4 or 5. In some embodiments, the variant is at least 80%, 85%, 90%, 95%, 96%, 97%, 98%, 99%, 99.5%, 99.6%, 99.7% or 99.8% identical to SEQ ID NO: 2, 3, 4 or 5 over the full length, amino acids 138-747 of SEQ ID NO: 2, 3, 4 or 5, or amino acids 203-747 of SEQ ID NO: 2, 3, 4 or 5. In some embodiments, the variant comprises, as compared to SEQ ID NO: 2, 3, 4 or 5, insertion, deletion, substitution and/or addition of 1, 2, 3, 4, 5, 6, 7, 8, 9, 10 or more amino acids. Preferably, the insertion of the amino acids is conducted at a site different from the inserted peptide of the present invention (SEQ ID NO: 10, 11, 12 or 13), more preferably not in loop IV. Preferably, the substitution of amino acid is a conserved substitution.

In some embodiments, the modified AAV capsid polypeptide is encoded by a nucleotide sequence selected from SEQ ID NOs: 14, 15, 16 and 17. In some embodiments, the modified AAV capsid polypeptide is encoded by a variant of SEQ ID NO: 14, 15, 16 or 17. In some embodiments, the variant is at least 80%, 85%, 90%, 95%, 96%, 97%, 98%, 99%, 99.5%, 99.6%, 99.7% or 99.8% identical to SEQ ID NO: 14, 15, 16 or 17. In some embodiments, the variant comprises, as compared to SEQ ID NO: 14, 15, 16 or 17, substitution and/or addition of 1, 2, 3, 4, 5, 6, 7, 8, 9, 10, 11, 12,13,14, 15, 16, 17, 18, 19, 20, 21, 22, 23, 24, 25, 26, 27, 28, 29, 30 or more nucleotides. In some embodiments, the variant comprises, as compared to SEQ ID NO: 14, 15, 16 or 17, insertion and/or deletion of 3n (n is an integer, which is 1, 2, 3, 4, 5, 6, 7, 8, 9, 10 or more) nucleotides. Preferably, the insertion of the nucleotides is conducted at a site different from the nucleotide sequence encoding the inserted peptide of the present invention (SEQ ID NO: 10, 11, 12 or 13), more preferably not in the nucleotide sequence encoding loop IV. Preferably, the variant is a degenerate variant, or the substitutions of nucleotides result in conserved substitutions of amino acids.

In some embodiments, the rAAV of the present invention exhibits improved infectivity to retinal cells as compared to the AAV comprising the parental AAV capsid polypeptides, preferably when administered by intravitreal injection.

The genome of the rAAV of the present invention comprises an expression cassette comprising a nucleotide sequence encoding a gene product. In some embodiments, the gene product is an interfering RNA. In some embodiments, the gene product is an aptamer. In some embodiments, the gene product is a polypeptide. In some embodiments, the gene product is a site-specific nuclease.

When the gene product is interfering RNA (RNAi), suitable RNAi includes RNAi that reduces the level of intracellular apoptosis or angiogenic factors. For example, RNAi can be a shRNA or siRNA that reduces the level of a gene product that induces or promotes apoptosis in a cell, including, for example, the Bax, Bid, Bak, and Bad gene products (See, for example, U.S. Pat. No. 7,846,730). Interfering RNA can also be anti-angiogenic products, such as shRNA or siRNA against VEGF, VEGFR1or VEGFR 2.

When the gene product is an aptamer, an exemplary target of aptamer includes, for example, VEGF and PDGF.

When the gene product is a polypeptide, the polypeptide usually enhances retinal cell function, such as rod-shaped or cone-shaped photoreceptor cells, retinal ganglion cells, muller cells, bipolar cells, amacrine cells, horizontal cells, or retinal pigment epithelial cells. Functional peptide. Exemplary polypeptides include neuroprotective polypeptides (e.g., GDNF, CNTF, NT4, NGF, and NTN); anti-angiogenic polypeptides (e.g., soluble vascular endothelial growth factor (VEGF) receptor; VEGF-binding antibodies; VEGF-binding antibody fragments such as scFv and nanobody; endostatin; tumstatin; angiostatin; pigment epithelium-derived factor (PEDF); soluble Tie-2 receptor, etc.; tissue inhibitor of metalloproteinase-3 (TIMP-3); photoreactive opsin (opsin), such as rhodopsin; anti-apoptotic polypeptide (e.g., Bcl-2, Bcl-X1), and the like. Suitable polypeptides include, but are not limited to, glial-derived neurotrophic factor (GDNF); fibroblast growth factor 2; neurotrophin (NTN); ciliary neurotrophic factor (CNTF); nerve growth factor (NGF); Neurotrophin-4 (NT4); a source neurotrophic factor (BDNF; epidermal growth factor; rhodopsin; X-linked inhibitor of apoptosis protein; and sonic factor (Sonic) Hedgehog).

In some embodiments, the gene product of interest is a site-specific endonuclease that provides a site-specific knockdown of gene function, which is associated with a retinal disease, for example, the gene is highly expressed in a disease.

In addition to knocking out defective alleles, site-specific nucleases can also be used to stimulate homologous recombination of donor DNA with a functional copy of a protein encoding a defective allele. Thus, for example, the rAAV of the present invention can be used to deliver a site-specific endonuclease that knocks out a defective allele and can be used to deliver a functional copy of a defective allele, causing functional copy repair, thereby providing a functional retinal protein. In some embodiments, the site-specific endonuclease and the functional copy of the defective allele are delivered by separate rAAVs.

Site-specific endonucleases include, for example, zinc finger nuclease (ZFN); transcription activator-like effector nuclease (TALEN), and CRISPR/Cas nuclease.

In some embodiments, the gene product is an antibody against VEGF. For example, Novamab identified a nanobody against VEGF, which is referred to as "Nb24", with an amino acid sequence of SEQ ID NO: 24. In some embodiments, the gene product is a polypeptide comprising SEQ ID NO: 24. In some embodiments, the gene product is a bi-valent Nb24 comprising two Nb24 linked by a linker, such as a $(G4S)_2$ linker. In some embodiments, the genome of the rAAV comprises an expression cassette encoding the bi-valent Nb24 flanked by ITRs, e.g., SEQ ID NO: 20.

The rAAV of the present invention provides an improved transduction into a retinal cell as compared to the parental AAV capsid polypeptide, an enhanced expression of the gene product, a reduced inflammatory response, a desired safety and/or a robust therapeutic effect on ocular diseases.

5. Pharmaceutical Composition and Medical Use

The present invention provides a pharmaceutical composition comprising: a) the rAAV of the present invention; and b) a pharmaceutically acceptable carrier, diluent, excipient or buffer. In some embodiments, a pharmaceutically acceptable carrier, diluent, excipient or buffer is suitable for use in humans.

Such excipients, carriers, diluents, and buffers include any agent that can be administered without abnormal toxicity. Pharmaceutically acceptable excipients include, but are not limited to, liquids such as water, saline, glycerol, and ethanol. Included therein may be pharmaceutically acceptable salts such as mineral acid salts such as hydrochlorides, hydrobromides, phosphates, sulfates, and the like; and salts of organic acids such as acetates, propionates, malonates, Benzoate and the like. In addition, auxiliary substances such as wetting or emulsifying agents, pH buffering substances and the like may be present in such vehicles. A wide variety of pharmaceutically acceptable excipients are known in the art and need not be discussed in detail herein. Pharmaceutically acceptable excipients have been described in detail in various publications including, for example, A. Gennaro (2000) "Remington: The Science and Practice of Pharmacy," 20th Edition, Lippincott, Williams, & Wilkins; Pharmaceutical Dosage Forms and Drug Delivery Systems (1999) Editing by HC Ansel et al, 7th edition, Lippincott, Williams, & Wilkins; and Handbook of Pharmaceutical Excipients (2000) AH Kibbe et al., 3rd edition, Amer. Pharmaceutical Assoc.

The present invention further provides a method of delivering a gene product to an eye, in particular, a retinal cell, of a subject comprising the administration of the rAAV or the pharmaceutical composition of the present invention to the eye. Delivery of the gene product to retinal cells can provide treatment for retinal diseases. The retinal cells may be photoreceptors, retinal ganglion cells, muller cells, bipolar cells, amacrine cells, horizontal cells, or retinal pigment epithelial cells. In some cases, the retinal cells are photoreceptor cells, such as rods or cones.

The present invention provides a method of treating a retinal disease, the method comprising administering to a subject in need thereof an effective amount of the rAAV or the pharmaceutical composition of the present invention. In some embodiments, the rAAV or the pharmaceutical composition is administered by intraocular injection or by intravitreal injection. The rAAV or the pharmaceutical composition is administered by a single-dose or a multiple-dose (e.g., 2, 3, 4 or more doses) scheme. For the multiple-dose scheme, the rAAV or the pharmaceutical composition can be administered at different intervals, such as daily, weekly, monthly, yearly, to achieve a desired level of gene expression.

Provided is also the rAAV or the pharmaceutical composition of the present invention, for use in the delivery of a gene product to an eye, in particular, a retinal cell, of a subject comprising the administration of the rAAV or the pharmaceutical composition of the present invention to the eye. Delivery of the gene product to retinal cells can provide treatment for retinal diseases. The retinal cells may be photoreceptors, retinal ganglion cells, muller cells, bipolar cells, amacrine cells, horizontal cells, or retinal pigment epithelial cells. In some cases, the retinal cells are photoreceptor cells, such as rods or cones.

Provided is also the rAAV or the pharmaceutical composition of the present invention, for use in the treatment of a retinal disease. In some embodiments, the rAAV or the pharmaceutical composition is administered by intraocular injection or by intravitreal injection. The rAAV or the pharmaceutical composition is administered by a single-dose or a multiple-dose (e.g., 2, 3, 4 or more doses) scheme. For the multiple-dose scheme, the rAAV or the pharmaceutical composition can be administered at different intervals, such as daily, weekly, monthly, yearly, to achieve a desired level of gene expression.

The present invention provides use of the rAAV or the pharmaceutical composition of the present invention in the preparation of a medicament for delivering a gene product to an eye, in particular, a retinal cell, of a subject.

The present invention provides use of the rAAV or the pharmaceutical composition of the present invention in the preparation of a medicament for treating a retinal disease in a subject in need thereof.

Ophthalmopathy that can be treated by the rAAV or the pharmaceutical composition of the present invention includes, but is not limited to, acute macular degeneration; Behcet's disease; choroidal neovascularization; diabetic uveitis; histoplasmosis; macular degeneration, such as acute macular degeneration Non-exudative age-related macular degeneration and exudative age-related macular degeneration; edema, such as macular edema, cystoid macular edema and diabetic macular edema; multifocal choroiditis; ocular trauma affecting the posterior eye or location; Ocular tumors; retinal disorders such as central retinal vein occlusion, diabetic retinopathy (including proliferative diabetic retinopathy), proliferative vitreoretinopathy (PVR), retinal artery occlusive disease, retinal detachment, retinitis of the retinitis Sympathetic ophthalmia; VogtKoyanagi-Harada (VKH) syndrome; diffuse ocular pigmentation; posterior ocular condition caused or affected by laser treatment of the eye;

posterior ocular condition caused or affected by photodynamic therapy; photocoagulation, Radiation retinopathy; preretinal membrane disorder; retinal vein branching; anterior ischemia Sexual optic neuropathy; non-retinal diabetic retinal dysfunction; retinal fistula (retinoschisis); retinitis pigmentosa; glaucoma; Usher syndrome; cone-rod cell dystrophy; Stargardt disease (yellow spot on the fundus); hereditary macular degeneration; chorioretinal degeneration; Leber's Congenital Amaurosis; congenital still night blindness; no choroid; Barbie Syndrome (Bardet-Biedlsyndrome); macular capillary dilatation; Leber's hereditary optic neuropathy; retinopathy of prematurity; and color vision disorders, including full color blindness, red blindness, green blindness, and blue blindness.

EXAMPLES

The following Examples are provided for illustration only, rather than for any limitation to the present application.

Figure 1B:
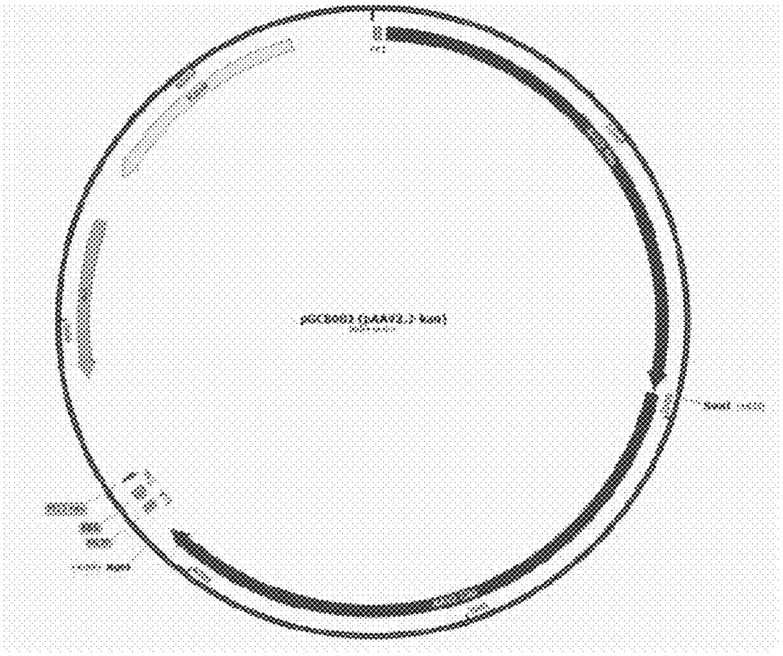
Figure 1C:
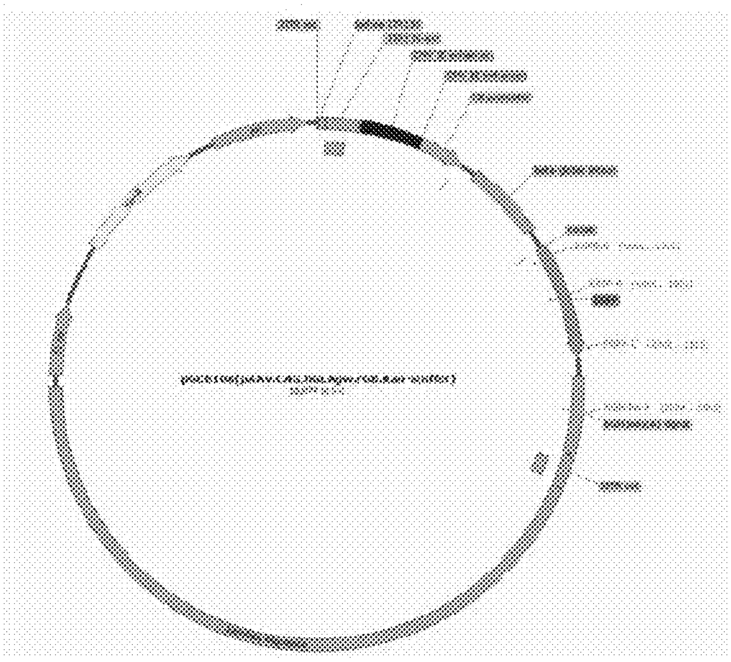
Figure 1D:
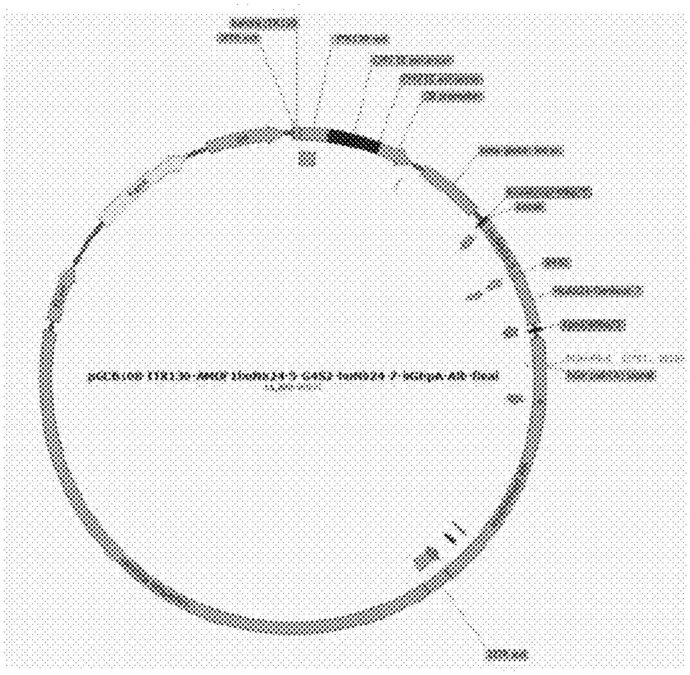

Example 1. Preparation of rAVV Vectors Comprising a Modified AAV Capsid Polypeptide rAAV vectors were prepared with a method similar to that described in Crosson S M et al. 2018, using different packaging plasmids and transgene plasmids. Briefly, 3E6 cells/ml 293VPC cells (Thermo, Catalog A35347) in serum free virus production medium OPM-293 CD05 (Shanghai OPM Biosciences Co.Ltd. Catalog: 81075-001) were triple transfected, using polyethylenimine, with the helper plasmid, the packaging plasmid encoding rep/cap, and the transgene plasmid below:

- helper plasmid ("pHelper" containing the Ad E2A, E4, and VA RNA helper genes as described in Crosson Sm et al., the map thereof is shown in FIG. 1A);
- packaging plasmid, the map thereof is shown in FIG. 1B, in which "AAV2 Cap" is the nucleotide sequence encoding the capsid polypeptide as listed in Table 1 (the second column);
- transgene plasmid, comprising the rAAV genome of SEQ ID NO: 19 encoding GFP or the rAAV genome of SEQ ID NO: 20 encoding bi-valent Nb24 which is an anti-VEGF antibody (see FIGS. 1C and 1D, respectively), in which the elements were assembled using Gibson assembly methodology (NEBuilder HiFi DNA Assembly Master Mix, NEB, Catalog E2621).

Packaging plasmids encoding the capsid polypeptide of SEQ ID NO: 1, 18 or 22 were synthesized at Genscript Inc, (Nanjing, Jiangsu Province, China), and the packaging plasmids encoding the capsid of SEQ ID NO: 2, 3, 4, 5, or 21 were constructed, starting from the packing plasmid encoding SEQ ID NO: 1, by inserting the nucleotide sequence of positions 1762-1797 of SEQ ID NO: 14, 15, 16, 17 or 26 between positions 1761 and 1762 of SEQ ID NO: 25 using Gibson assembly methodology (NEBuilder HiFi DNA Assembly Master Mix, NEB, Catalog E2621).

Following 72 h incubation at 37° C., cells were harvested, and viral particles were purified through an iodixanol gradient (see Crosson S M et al.).

The rAAVs were tested for titers by ddPCR, which were all at the level of $10^{13}$ viral genomes (vg)/mL. In particular, the ddPCR was carried out with Bio-Rad's QXDx AutoDG ddPCR System and QXDx Universal Kit for AutoDG ddPCR System according to the manufacturer's instructions. The primers for the ddPCR are as follows.

For the amplification of GFP:

```
GFP-F
ACTACAACAGCCACAACGTCTATATCA

GFP-R
GGCGGATCTTGAAGTTCACC

GFP-P
5'-6-FAM-CCGACAAGC-ZEN-AGAAGAACGGCATCA-
Iowa Black FQ-3'
```

For the amplification of Nb24

```
qPCR-AMD-24-5-F
GAGTGCGAGCTGGTGAG

qPCR-AMD-24-5-R
GCGTAGTCCCTGCTGATG

qPCR-AMD-24-5-P
CAAGGACGGCAGCACCTACTACAC
```

The rAAVs as prepared were listed in Table 1.

TABLE 1

| rAAV | Capsid polypeptide (VP1) in the rAAV (SEQ ID NO: ) | Product of the transgene in the rAAV |
|---|---|---|
| AAV2-GFP | 1 | GFP |
| AAV.GKG-GFP | 2 | GFP |
| AAV.LAE-GFP | 3 | GFP |
| AAV.LGP-GFP | 4 | GFP |
| AAV.NSP-GFP | 5 | GFP |
| AAV2-Nb24 | 1 | bi-valent Nb24 |
| AAV.GKG-Nb24 | 2 | bi-valent Nb24 |
| AAV.LAE-Nb24 | 3 | bi-valent Nb24 |
| AAV.LGP-Nb24 | 4 | bi-valent Nb24 |
| AAV.NSP-Nb24 | 5 | bi-valent Nb24 |
| AAV.7m8-Nb24 | 21 | bi-valent Nb24 |
| AAV.RH10-Nb24 | 22 | bi-valent Nb24 |
| AAV9-Nb24 | 18 | bi-valent Nb24 |

Example 2. In Vitro Test of the rAAVs in Retinal Cells Modified AAV Capsid

This Example was carried out to verify the expression of the GFP marker contained in the rAAVs as prepared in Example 1, and the test results show an enhanced expression of the GFP marker in retinal cells transduced with the rAAVs comprising a modified AAV capsid polypeptide.

Human retinal pigment epithelial cell (ARPE19 cells, ATCC: CRL-2302) were plated to 96-well plate (Thermo Scientific™ 165305). AAV2-GFP and AAV.LGP-GFP as prepared in Example 1 were added at various MOIs (800, 4,000, 20,000, and 100,000) to the ARPE19 cells 4 hours after the cells were plated. After 72 hours of incubation in 37C 5% CO2, the culture media was changed to PBS (Thermo, Catalog 10010072) and then, the transduced cells were detected for GFP protein with Automated fluorescence microscope (Agilent), 485/20 excitation, 508/20 emission filter setting.

Figure 2:
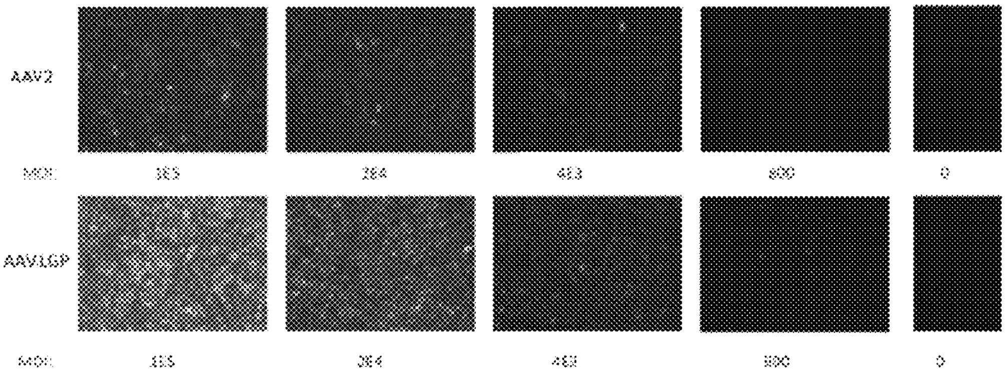
FIG. 2 shows the fluorescent microscopy of retinal cells transduced with rAAVs comprising a genome encoding GFP at various MOIs.

The rAAVs with a modified AAV2 capsid showed enhanced transduction rate as compared to that with a wildtype AAV2 capsid. As shown in FIG. 2, cells transduced with AAV.LGP-GFP exhibit much stronger fluorescent signal than cells transduced with AAV2-GFP. In particular, for AAV2-GFP, the fluorescent signal can be observed at the MOI of at least 4,000, but for AAV.LGP-GFP the fluorescent signal can be observed at the MOI of 800; and the cells transduced with AAV.LGP-GFP at the MOI of 4,000 exhibit comparable fluorescent signal to the cells transduced with AAV2-GFP at the MOI of 100,000.

Example 3. In Vitro Test of the rAAVs in Retinal Cells

This Example was carried out to verify the expression of the polypeptide of interest contained in the rAAVs as prepared in Example 1, and an enhanced expression of the polypeptide of interest were shown in the retinal cells transduced with the rAAVs comprising a modified AAV capsid polypeptide as compared to the rAAV comprising a wildtype capsid polypeptide.

ARPE19 cells were transduced with the rAAVs encoding bi-valent Nb24 as prepared in Example 1 at various MOIs (100,000, 30,000, 10,000, 3,000, 1,000, 300, 100 and 30) as described in Example 2. 72 hours after adding the rAAVs, the culture media were collected by pipetting, and then, detected for the Nb24 expression in the cell culture media by direct anti-VEGF ELISA.

In brief, a VEGF polypeptide (human VEGFA165A, R&D systems, catalog 293-VE/CF) was coated on an ELISA plate (Corning™ 3690) overnight at 4° C., after blocking with 3% BSA in PBST (Thermo, 37536), the harvested cell culture media containing bi-valent Nb24 was added to the plate, which was then incubated for 1 hour (RT). Anti-Nb24 antibody (Goat Anti-Nb24 polyclonal, Novamb) and anti-goat HRP antibody (Donkey anti-Goat IgG HRP, Invitrogen, catalog 34028) were added sequentially with a one-hour incubation (RT) after the addition of each antibody. The TMB solution (Thermo Scientific, catalog 34028) was added for HRP color development, which was then stopped by adding the stop buffer (Sulfoacid, Beyotime, catalog P0215). The absorbance OD450 was measured in a plate reader (SpectraMax i3x Multi-Mode Microplate Reader, Molecular Devices) for the calculation of the bi-valent Nb24 expression level in cell culture media. The expression levels of Nb24 were calculated based on a standard curve prepared with recombinant bi-valent Nb24 protein at a series of concentrations and were shown in FIG. 3 and the ED50 values (MOI for 50% max expression) of the rAAVs were calculated with Graphpad Prism and shown in Table 2.

TABLE 2

ED50 of the rAAVs

| rAAV | ED50 |
|---|---|
| AAV2-Nb24 | 556.2 |
| AAV.7m8-Nb24 | 546.4 |
| AAV.RH10-Nb24 | 3723 |
| AAV9-Nb24 | 3493 |
| AAV.GKG-Nb24 | 1717 |
| AAV.LAE-Nb24 | 8596 |
| AAV.LGP-Nb24 | 431.9 |
| AAV.NSP-Nb24 | 577.5 |

Figure 3:
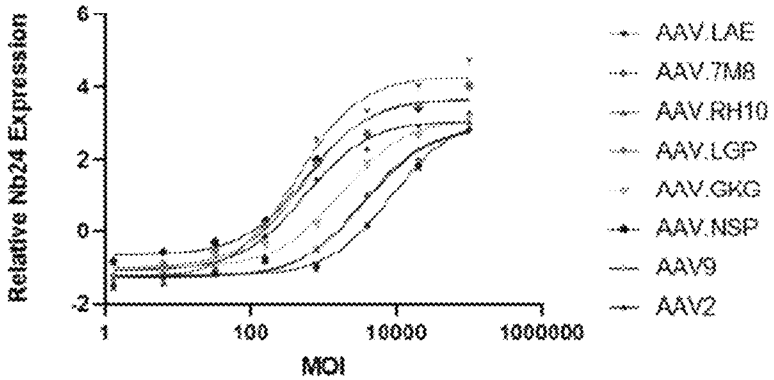
FIG. 3 shows the expression of Nb24 in retinal cells transduced with rAAVs comprising a genome encoding bi-valent Nb24 and various capsid polypeptides, the Y-axis shows the "1g" value of the concentration, the "0" point represents the concentration of "1".

According to FIG. 3, AAV.LGP-Nb24 achieved the highest expression of bi-valent Nb24, AAV.NSP-Nb24 showed an expression of bi-valent Nb24 higher than AAV2-Nb24 (wildtype), and comparable to AAV.7m8-Nb24 (reference), and AAV.GKG-Nb24 and AAV.LAE-Nb24 achieved an expression of Nb24 comparable to AAV2-Nb24. According to Table 2, AAV.LGP-Nb24 showed the lowest ED50, and the ED50 of AAV.NSP-Nb24 is comparable to AAV2-Nb24, and AAV.7m8-Nb24.

It demonstrated that the rAAVs comprising a modified AAV capsid polypeptide of the present invention achieved enhanced expression of the polypeptide encoded by the rAAVs (bi-valent Nb24) as compared to the rAAV comprising a wildtype capsid polypeptide or a reference capsid polypeptide.

Example 4. In Vivo Therapeutic Effect of rAAVs Comprising a Modified AAV Capsid Polypeptide This Example was carried out to verify the expression of transgene and the therapeutic efficacy in laser induced choroidal neovascularization (CNV) non-human primate (NHP) model achieved by the rAAVs comprising a modified AAV capsid polypeptide.

The study was carried out by a CRO company (JOINN LABORATORIES, China. In brief, ocular naïve cynomolgus monkeys were selected per serum AAV neutralization antibody (Nab) screening (20 monkeys with the lowest level of Nab). The selected monkeys were treated with laser for modeling (see Pennesi, et al., Animal models of age related macular degeneration. Mol Aspects Med, 2012. 33 (4): p. 487-509).

The rAAVs encoding bi-valent Nb24 prepared in Example 1 (as listed in Table 1) in formulation buffer (dPBS+200 mM NaCl+0.005% PF68, in which dPBS and PF68 were purchased from Thermo under Catalogs of 10010072 and 24040032, respectively) were administered to the eyes of monkeys as described in Table 3.

TABLE 3

| Group | Test Article | Name of the test article in FIG. 6-16 | ddPCR titer (vg/ml) | ROA * | Vol/eye (μL) | Dose (vg/eye) | No. of eyes | Animal ID #- |
|---|---|---|---|---|---|---|---|---|
| A | Vehicle | Vehicle | n/a | IVT | 50 | n/a | 6 | 291, 292, 309 |
| B | Eylea ® (Aflibercept) | Eylea | n/a | IVT | 50 | 2 mg | 4 | 293, 294 |
| C | AAV.LAE-Nb24 | SKG105 | 1E13 | IVT | 50 | 5E11 | 4 | 295, 296 |

TABLE 3-continued

| Group | Test Article | Name of the test article in FIG. 6-16 | ddPCR titer (vg/ml) | ROA * | Vol/eye (μL) | Dose (vg/eye) | No. of eyes | Animal ID #- |
|---|---|---|---|---|---|---|---|---|
| D | AAV.RH10-Nb24 | ssAAV-Rh10 | 1E13 | IVT | 50 | 5E11 | 4 | 297, 298 |
| E | AAV.LGP-Nb24 | SKG106 | 1E13 | IVT | 50 | 5E11 | 4 | 299, 300 |
| F | AAV.7m8-Nb24 | Reference | 1E13 | IVT | 50 | 5E11 | 4 | 301, 302 |
| G | AAV.GKG-Nb24 | SKG107 | 1E13 | IVT | 50 | 5E11 | 4 | 303, 304 |
| H | AAV.NSP-Nb24 | SKG108 | 1E13 | IVT | 50 | 5E11 | 4 | 305, 306 |
| I | AAV9-Nb24 | ssAAV9 | 1E13 | SRI | 50 | 5E11 | 6 | 307, 308, 310 |

* ROA: route of administration, IVT: intravitreal, SRI: sub-retinal injection.

Figure 4:
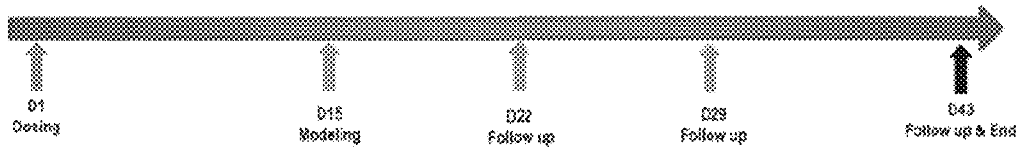
FIG. 4 shows the workflow of the study in laser induced choroidal neovascularization (CNV) non-human primate (NHP) model.

The study was carried out according to FIG. 4. In brief, the tested articles were intravitreal injected to the monkeys on Day 1, the eyes were imaged on Day 0, 22, 29 and 43, the monkeys were modeled on Day 15, and the sera of the monkeys were collected on Day 3, 7, 14, 22, 29 and 43. The monkeys #291-309 were sacrificed on Day 43, and their tissues (eye tissues, including retina, choroid, sclera, optic nerve, vitreous body, aqueous humor, ciliary body, iris, cornea and lens; and peripheral tissues including brain, heart, liver, kidney, lung, skeletal muscle and spleen) were collected, separately. The monkey #310 was administered with a second dose of AAV9-Nb24 on Day 44, and its eyes were further imaged on Day 51.

Samples comprising bi-valent Nb24 from the tissues were prepared by mixing the 30 mg tissue and 60 μL lysis buffer (T-PER™ Tissue Protein Extraction Reagent, Thermo, Catalog 78510) with proteinase inhibitors (Pierce™ Protease and Phosphatase Inhibitor Mini Tablets, Thermo, Catalog A32959) homogenizing the mixture with a homogenizer (2010 Geno/Grinder®-Automated Tissue Homogenizer and Cell Lyser, Spex SamplePrp) at 1,500 rpm for 2 min with 30s interval, centrifuging at 12,000 rpm for 20 min and collecting the supernatant. The total protein contents in the samples were determined with BCA kit (Thermo Fisher, Catalog 23235)

Figure 5:
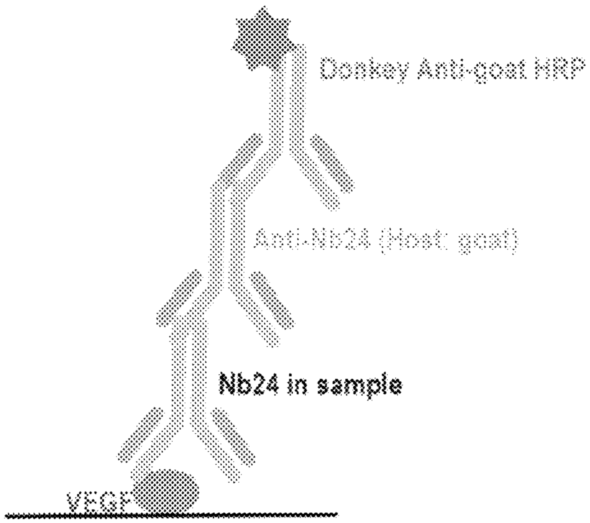
FIG. 5 shows the mechanism of the ELISA for the detection of Nb24.
Figure 6A:
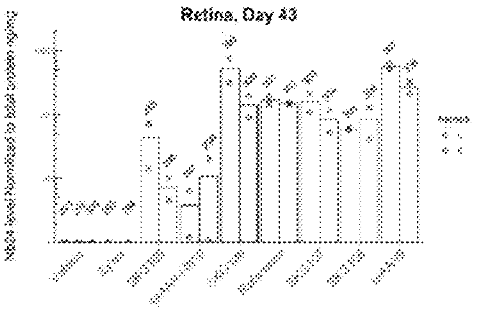
FIGS. 6A-6J show the Nb24 levels in eye tissues.
Figure 6B:
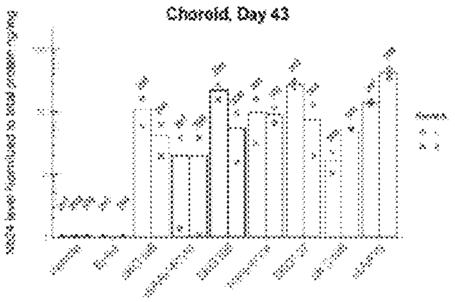
Figure 6C:
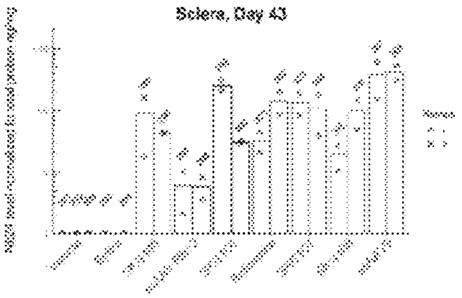
Figure 6D:
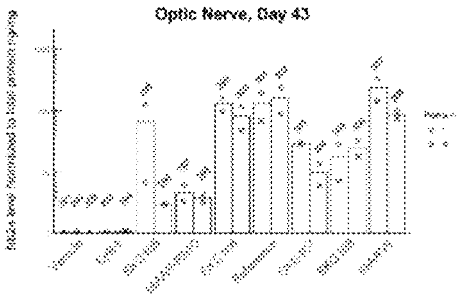
Figure 6E:
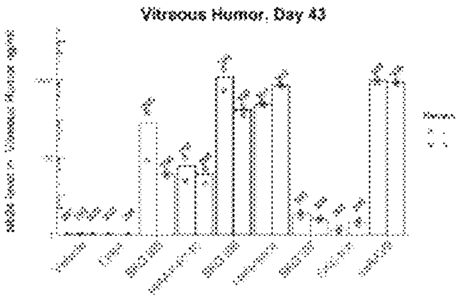
Figure 6F:
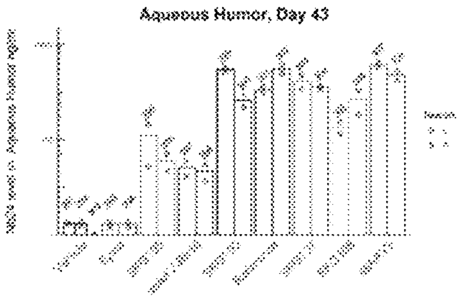
Figure 6G:
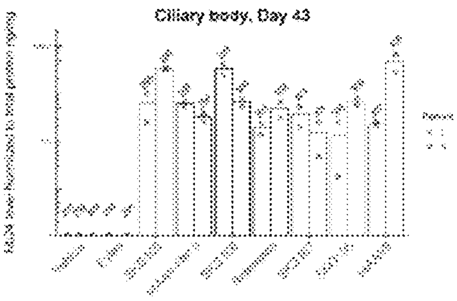
Figure 6H:
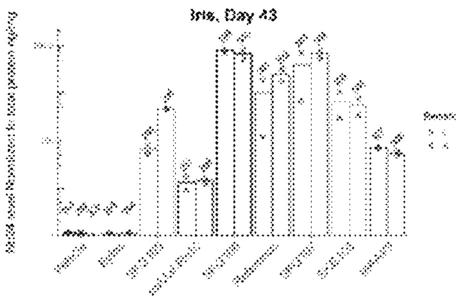
Figure 6I:
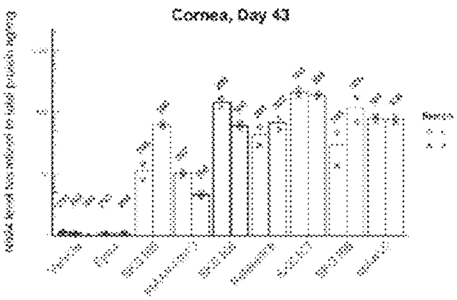
Figure 6J:
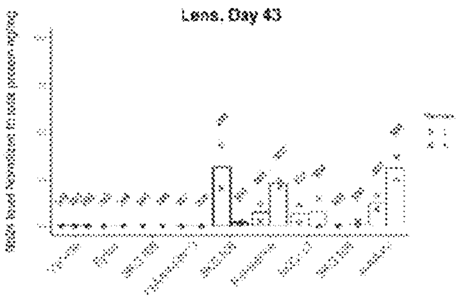

The Nb24 levels in tissues and sera were detected by ELISA (see FIG. 5). In brief, human VEGFA165A (R&D systems 293-VE/CF) was coated on the ELISA plate overnight at 4° C., after blocking with the blocking buffer (SuperBlock™ T20 (TBS) Blocking Buffer, Thermo Scientific, catalog 37536), the samples from the tissues and sera comprising equal content of total protein were added to the plate, followed by a one-hour incubation (RT). Anti-Nb24 antibody (Goat Anti-Nb24 polyclonal, Novamb) and anti-goat HRP antibody (Donkey anti-Goat IgG HRP, Invitrogen, catalog 34028) were added sequentially with a one-hour incubation (RT) after the addition of each antibody. The TMB solution (Thermo Scientific, catalog 34028) was added for HRP color development, which was then stopped by adding the stop buffer (Sulfoacid, Beyotime, catalog P0215). The absorbance OD450 was measured for the calculation of the bi-valent Nb24 expression level in the samples as described in Example 3.

Figure 7A:
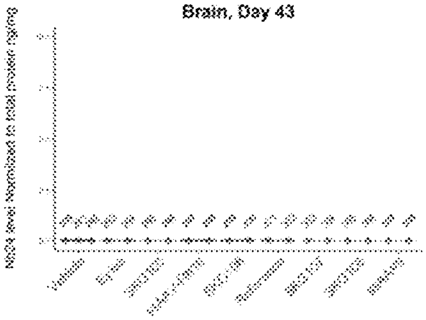
FIG. 7A-7H show the Nb24 levels in the peripheral tissues and sera.
Figure 7B:
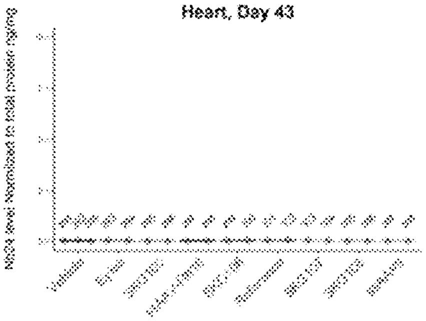
Figure 7C:
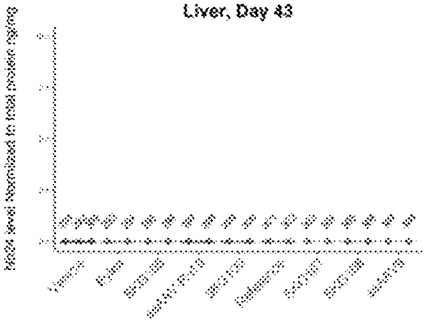
Figure 7D:
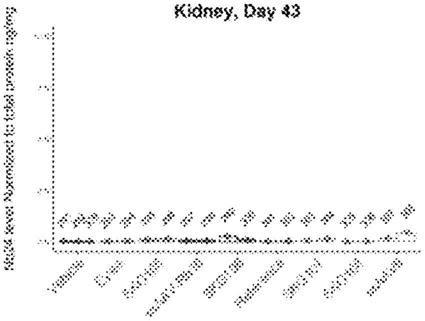
Figure 7E:
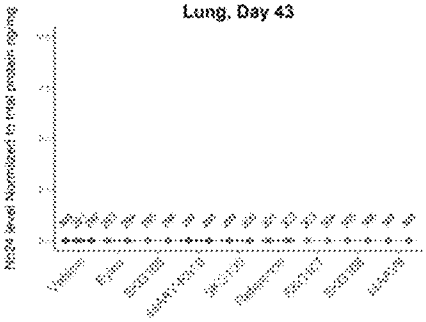
Figure 7F:
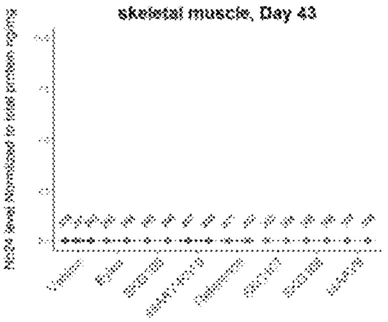
Figure 7G:
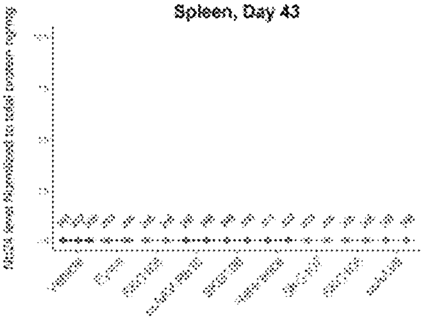
Figure 7H:
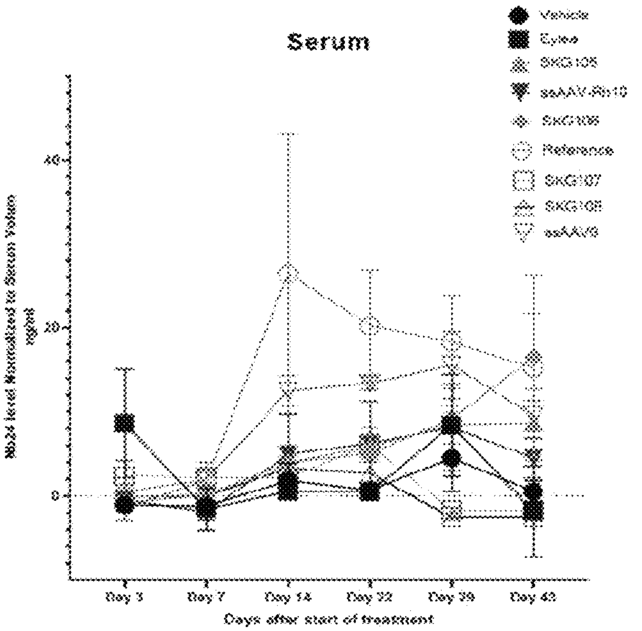
Figure 8A:
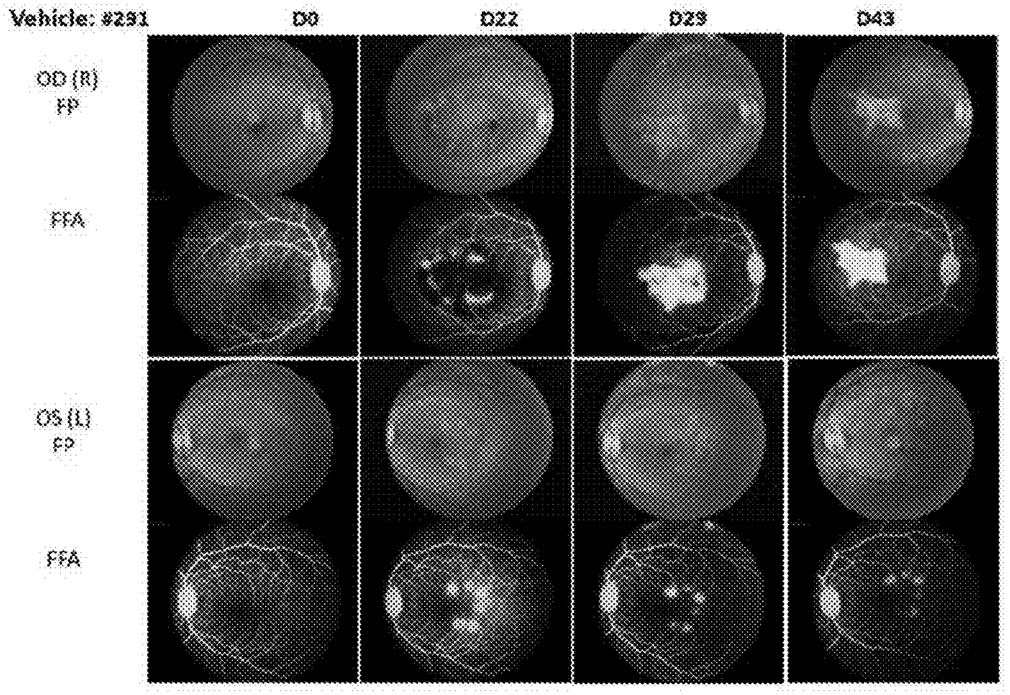
FIGS. 8A-16C show Fundus photography (FP) and Fundus photography (FFA) images of the left (OS) and right (OR) eyes of the monkeys treated with Vehicle (FIGS. 8A-8C), Eylea® (FIGS. 9A-9B), AAV.LAE-Nb24 (FIGS. 10A-10B), AAV.RH10-Nb24 (FIGS. 11A-11B), AAV.LGP-Nb24 (FIGS. 12A-12B), AAV.7m8-Nb24 (FIGS. 13A-13B), AAV.GKG-Nb24 (FIGS. 14A-14B), AAV.NSP-Nb24 (FIGS. 15A-15B) and AAV9-Nb24 (FIGS. 16A-16C).
Figure 8B:
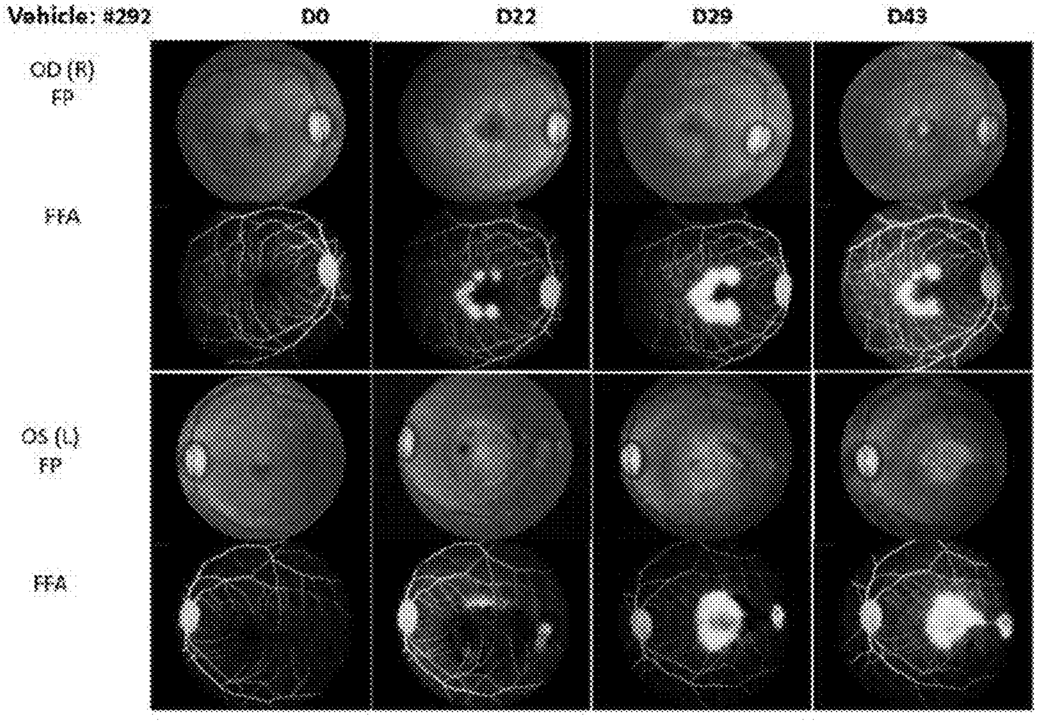
Figure 8C:
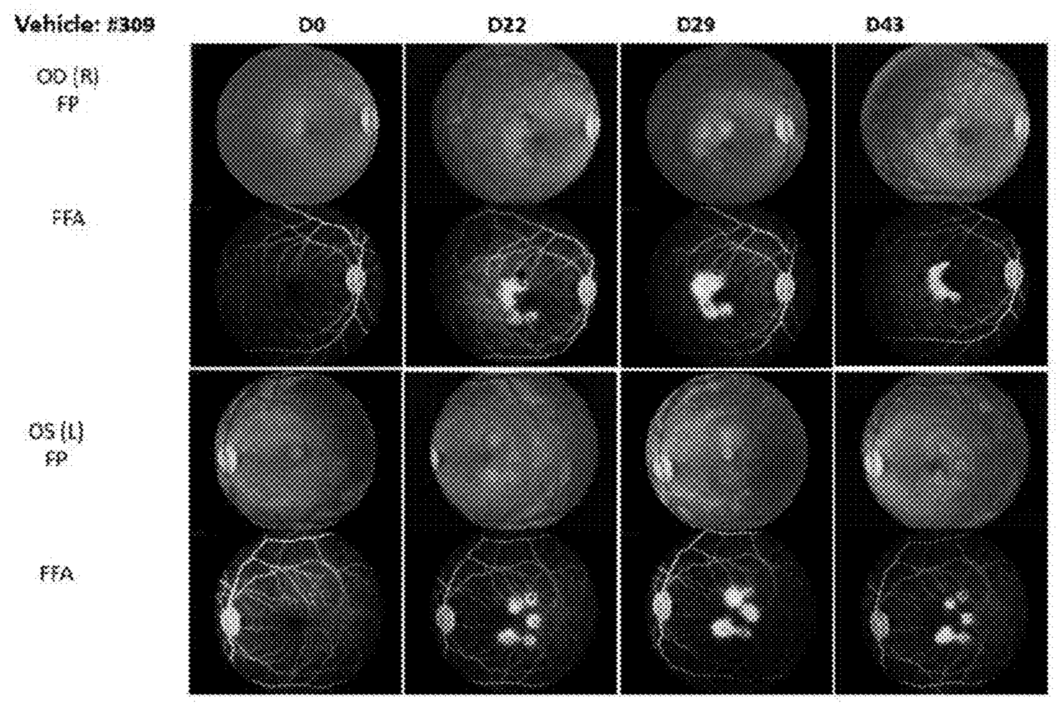
Figure 9A:
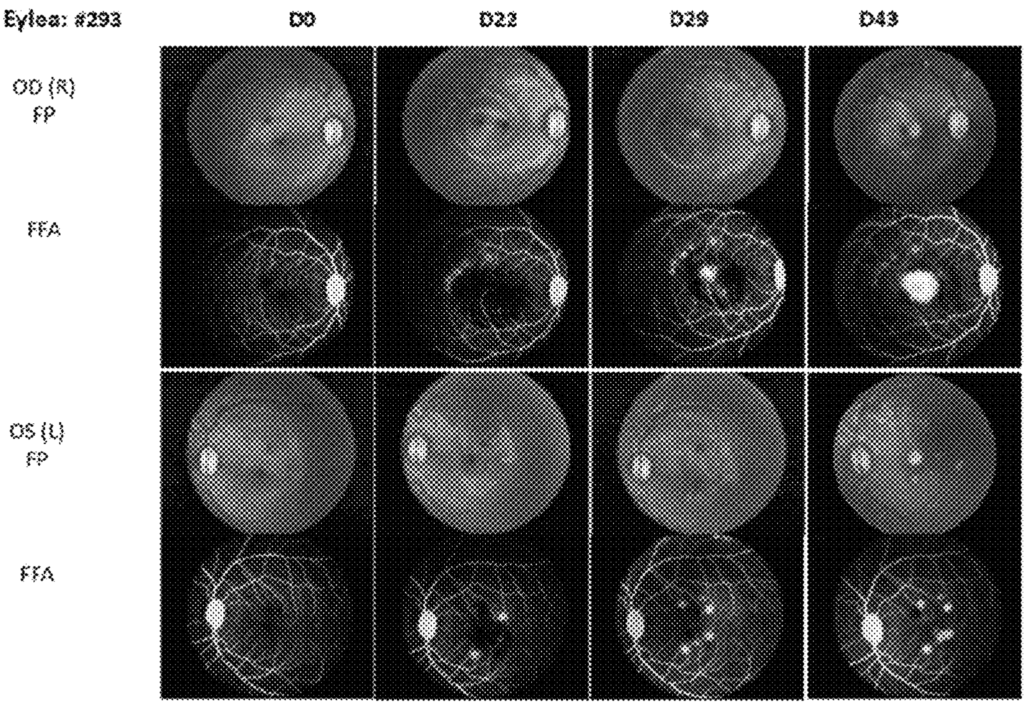
Figure 9B:
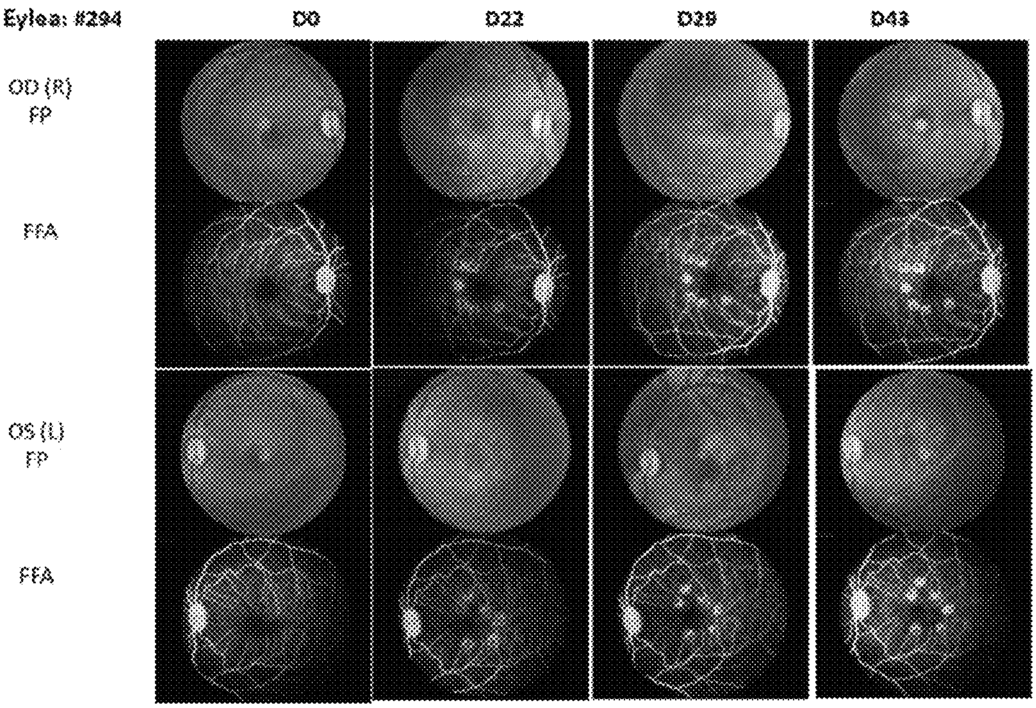
Figure 10A:
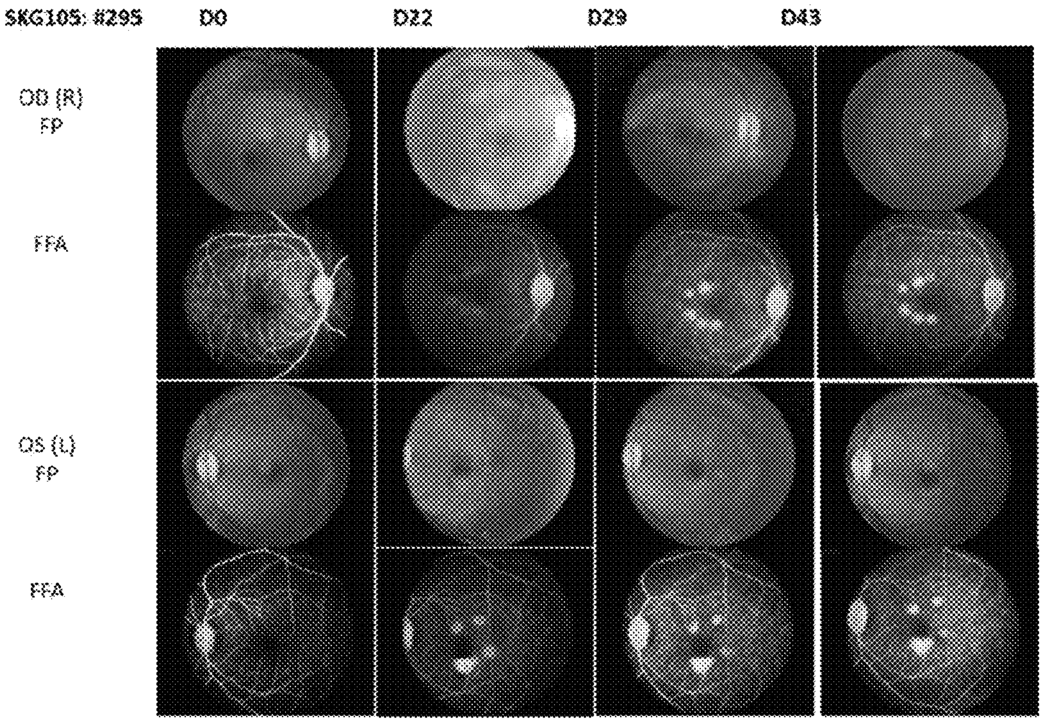
Figure 10B:
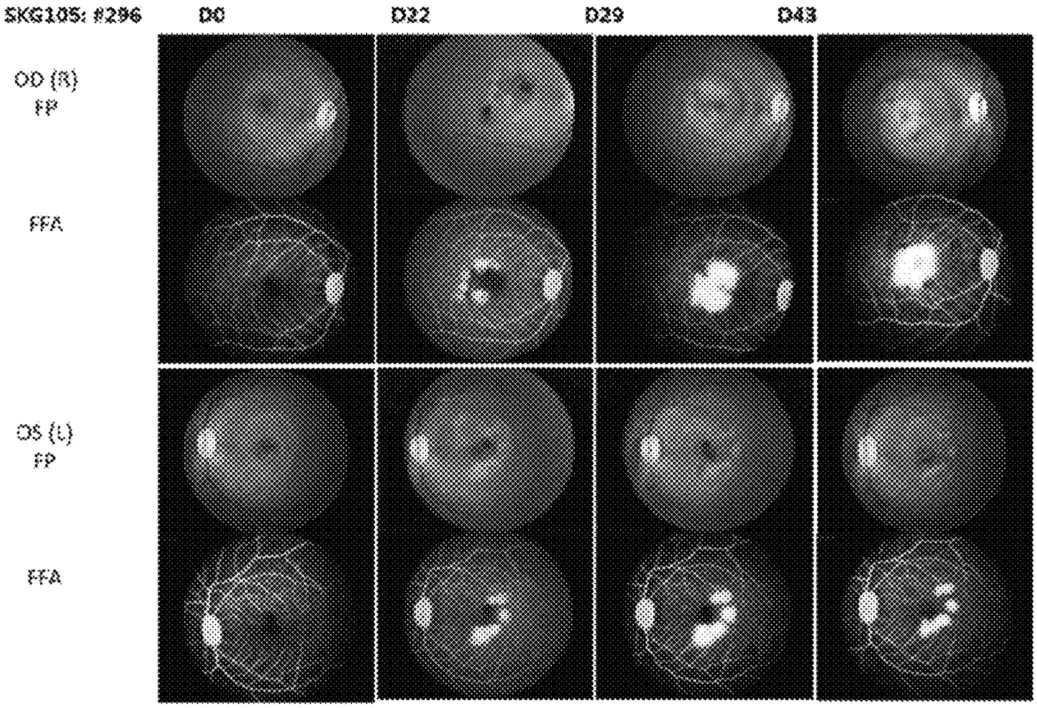
Figure 11A:
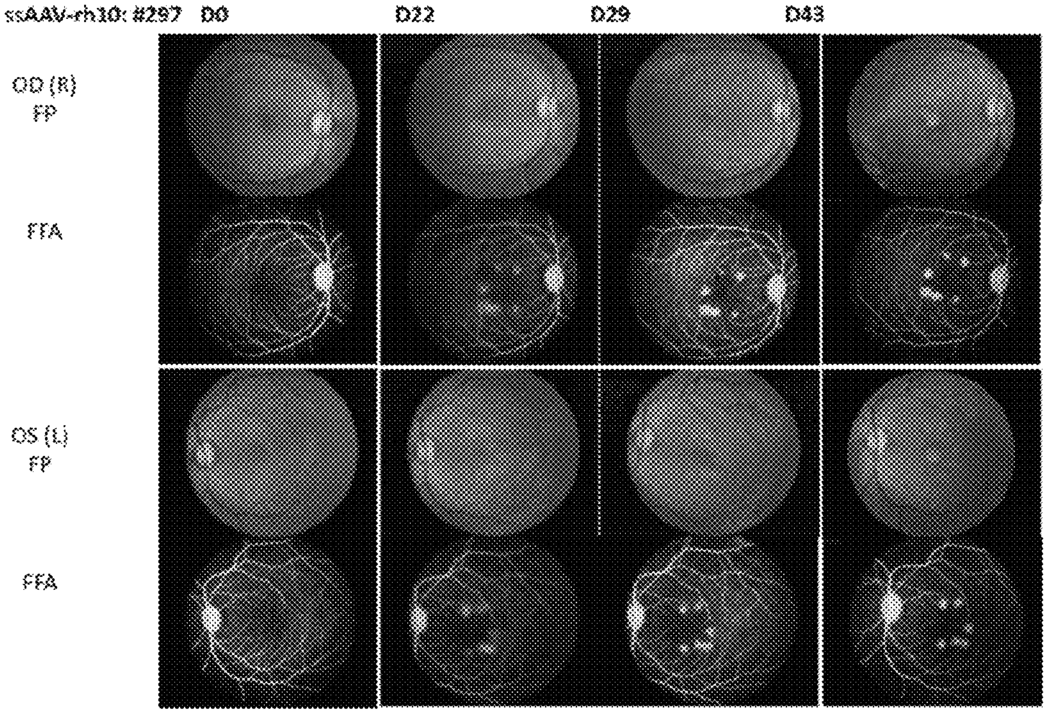
Figure 11B:
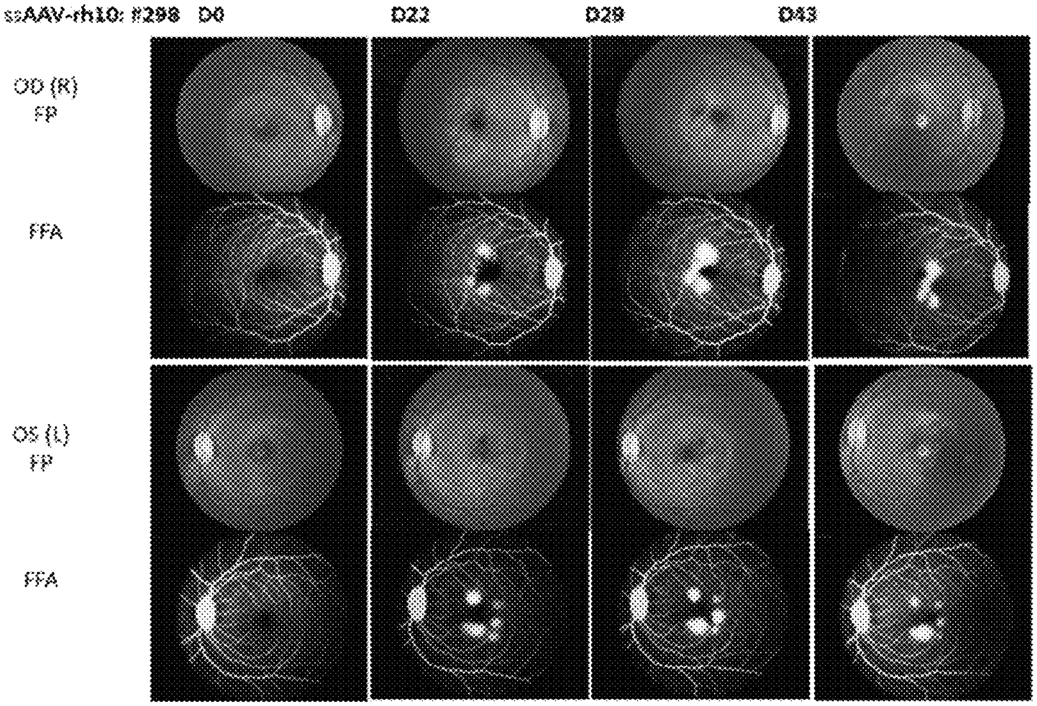
Figure 12A:
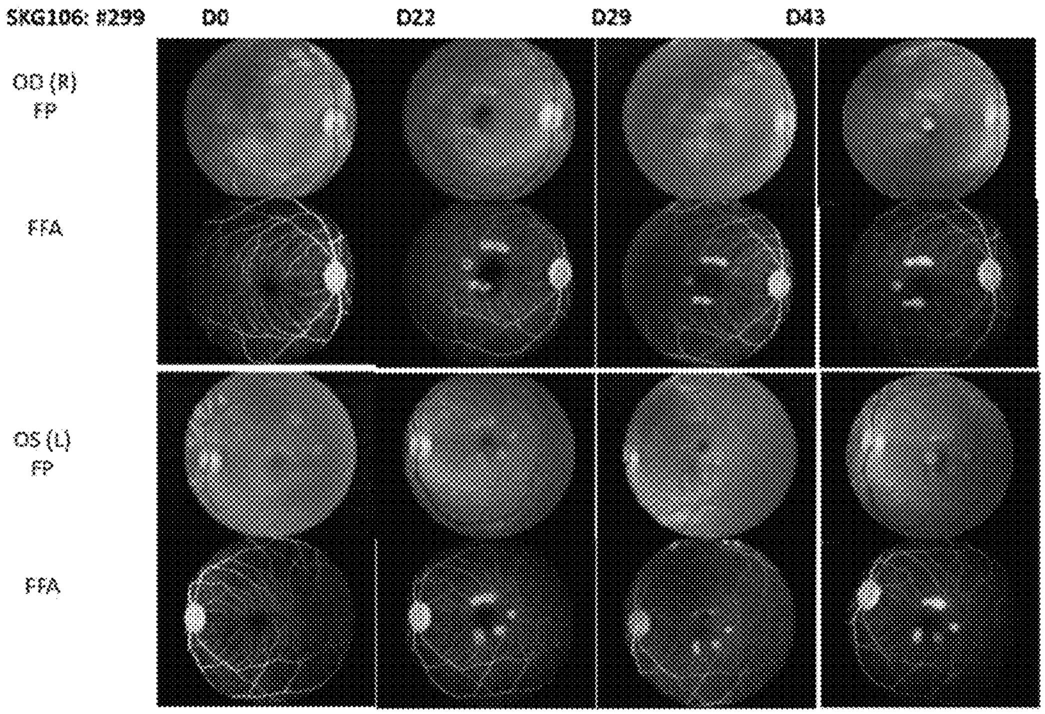
Figure 12B:
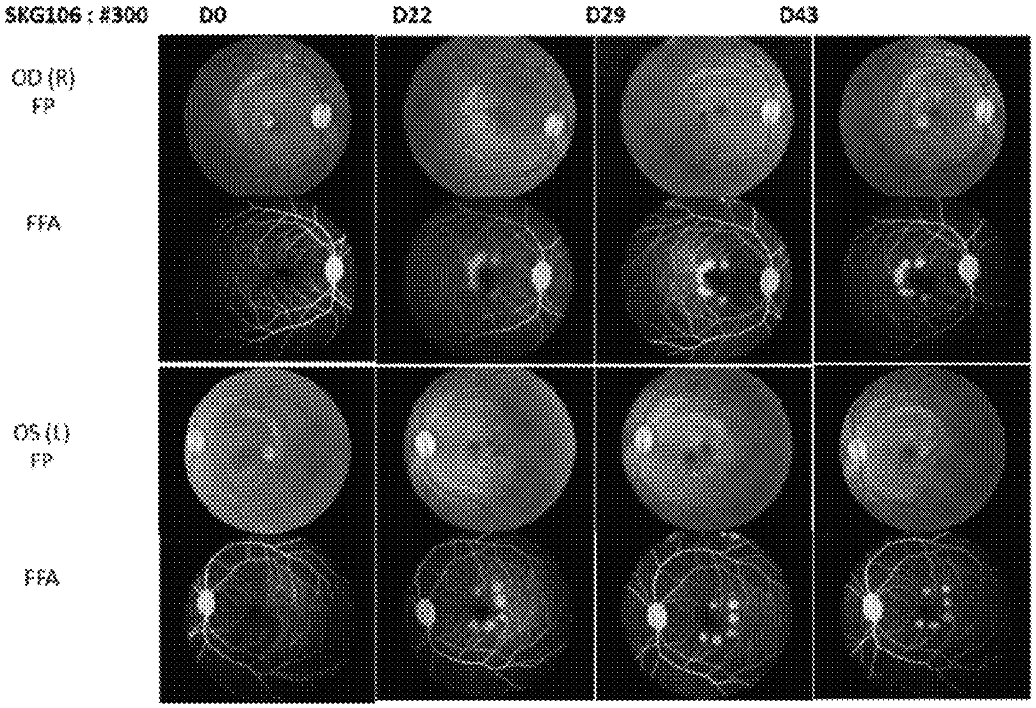
Figure 13A:
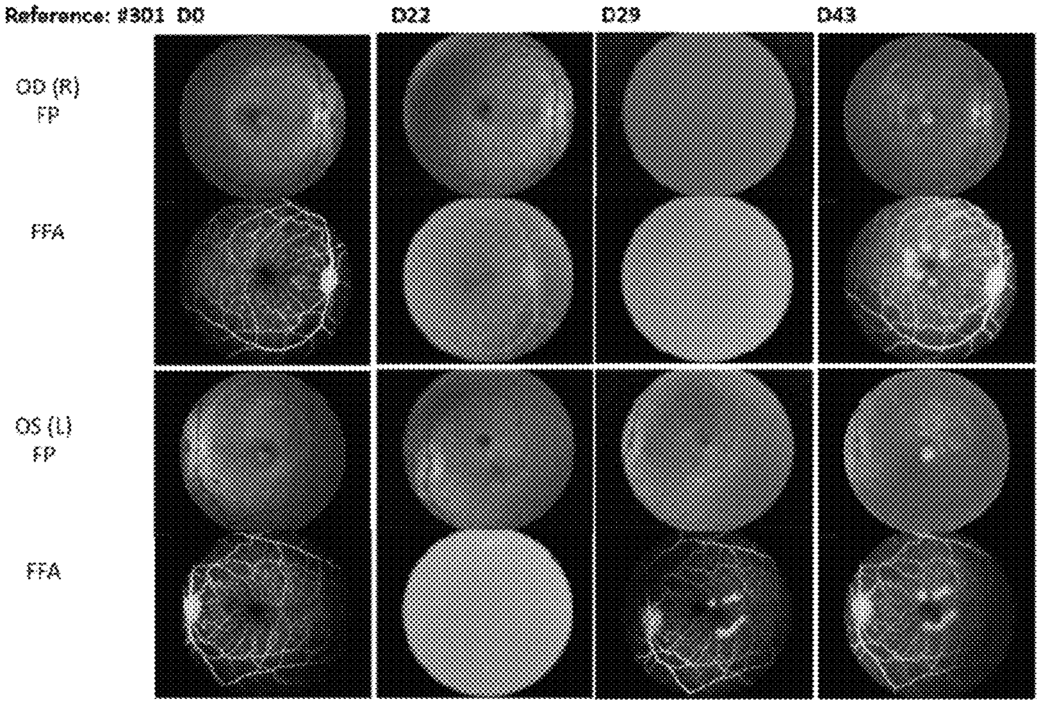
Figure 13B:
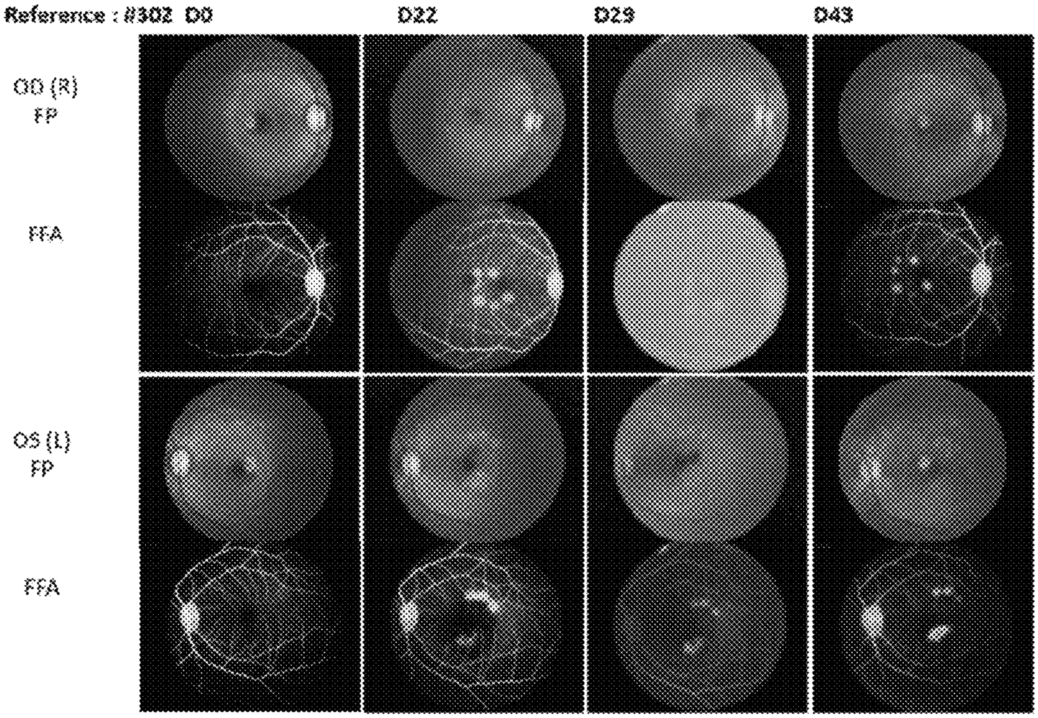
Figure 14A:
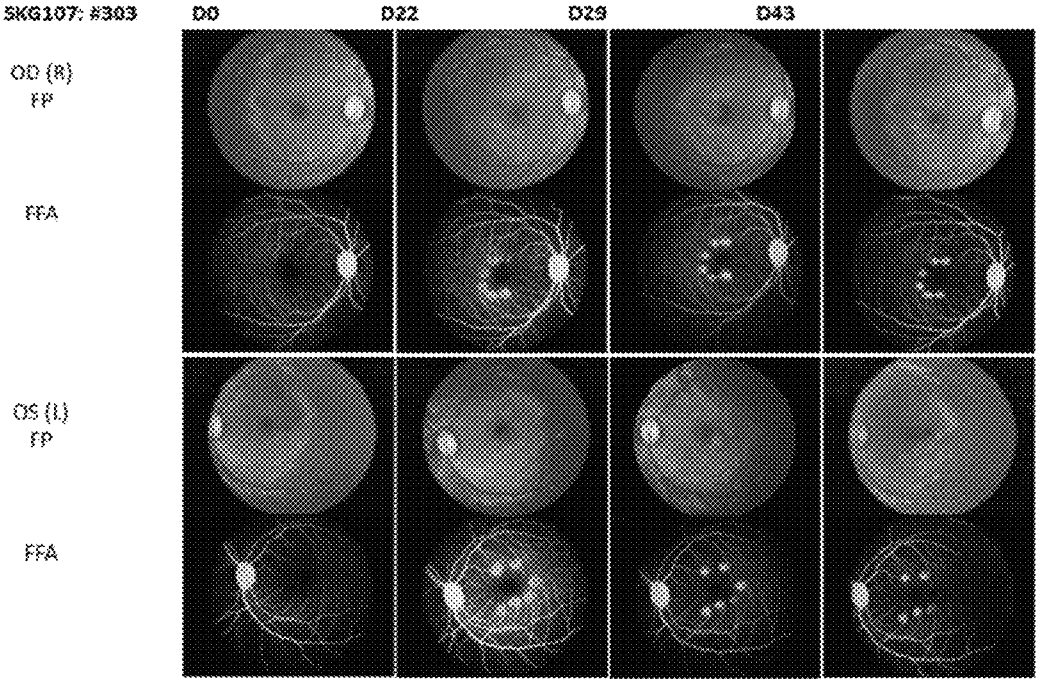
Figure 14B:
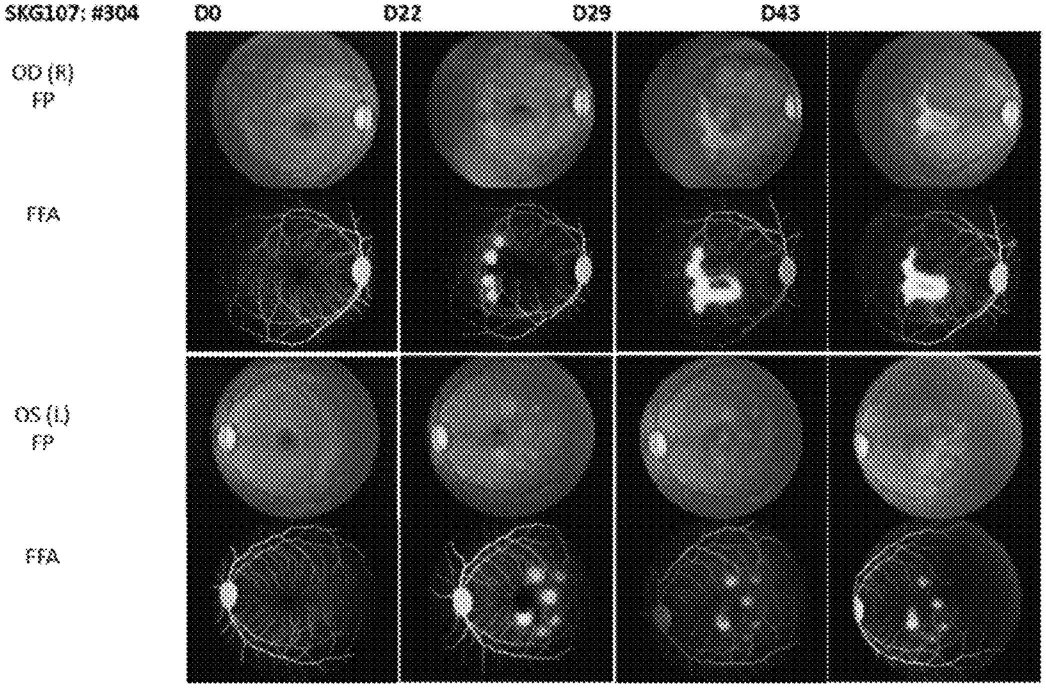
Figure 15A:
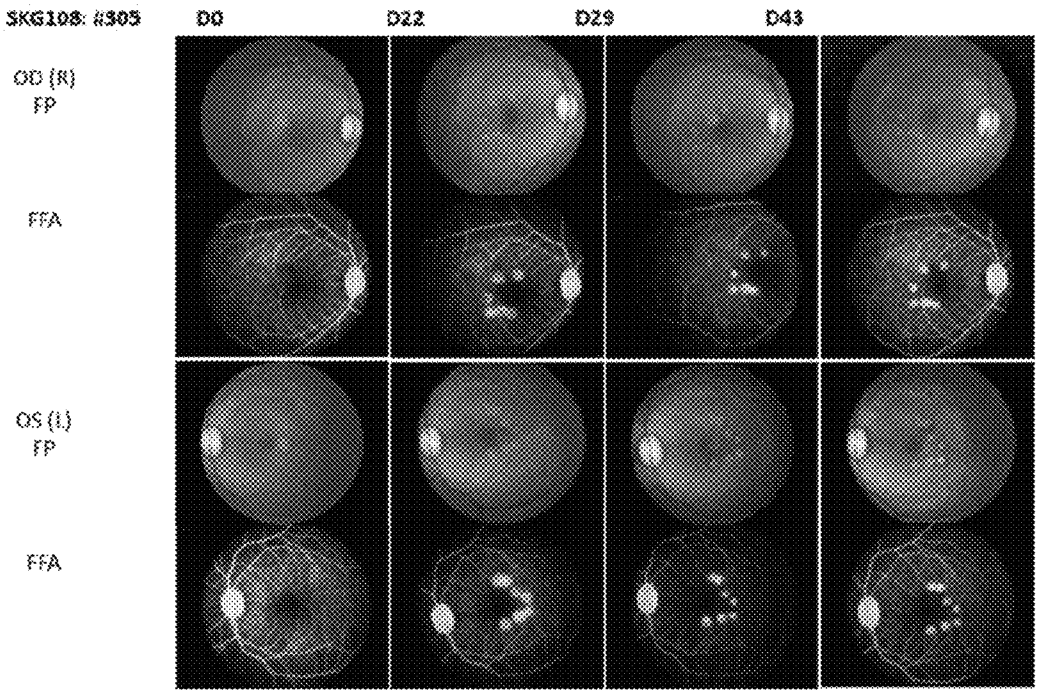
Figure 15B:
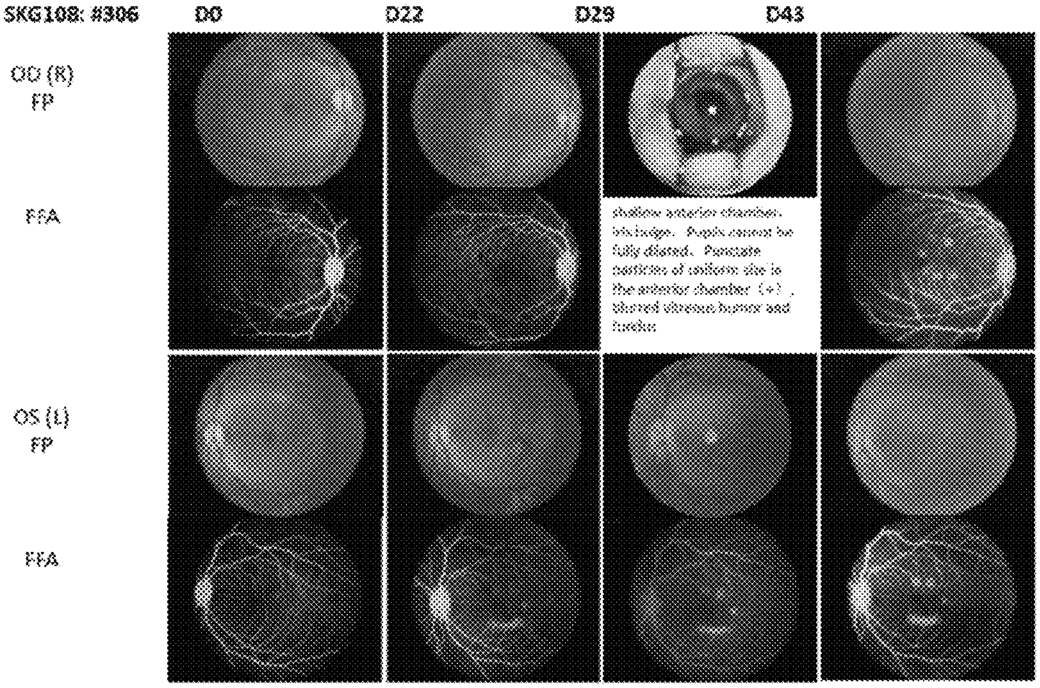
Figure 16A:
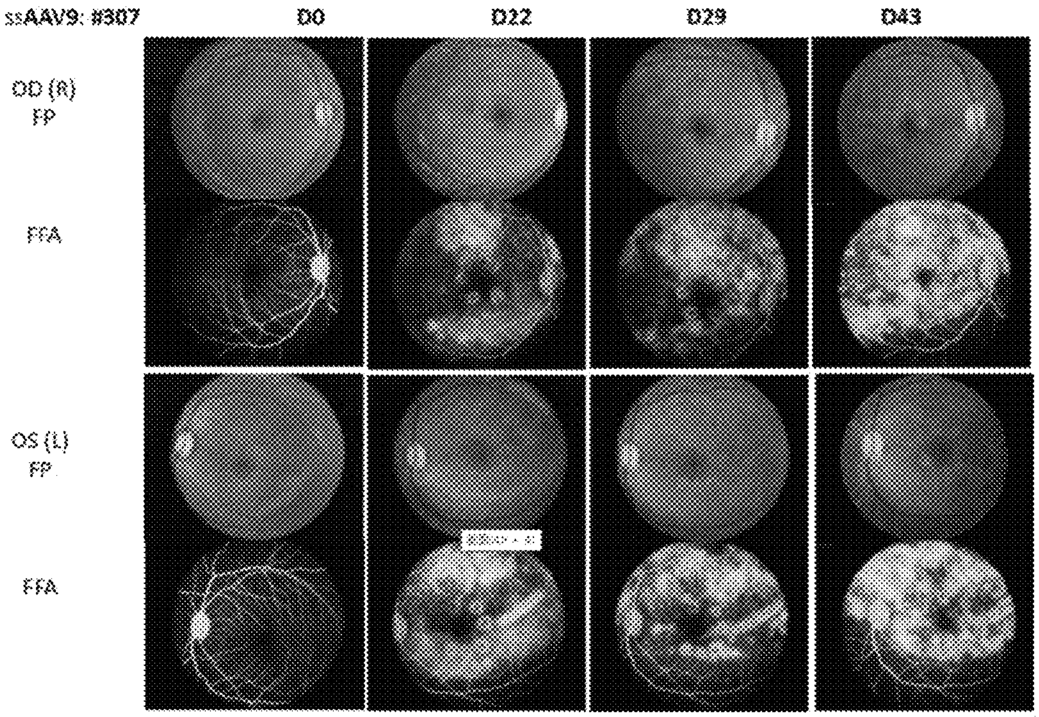
Figure 16B:
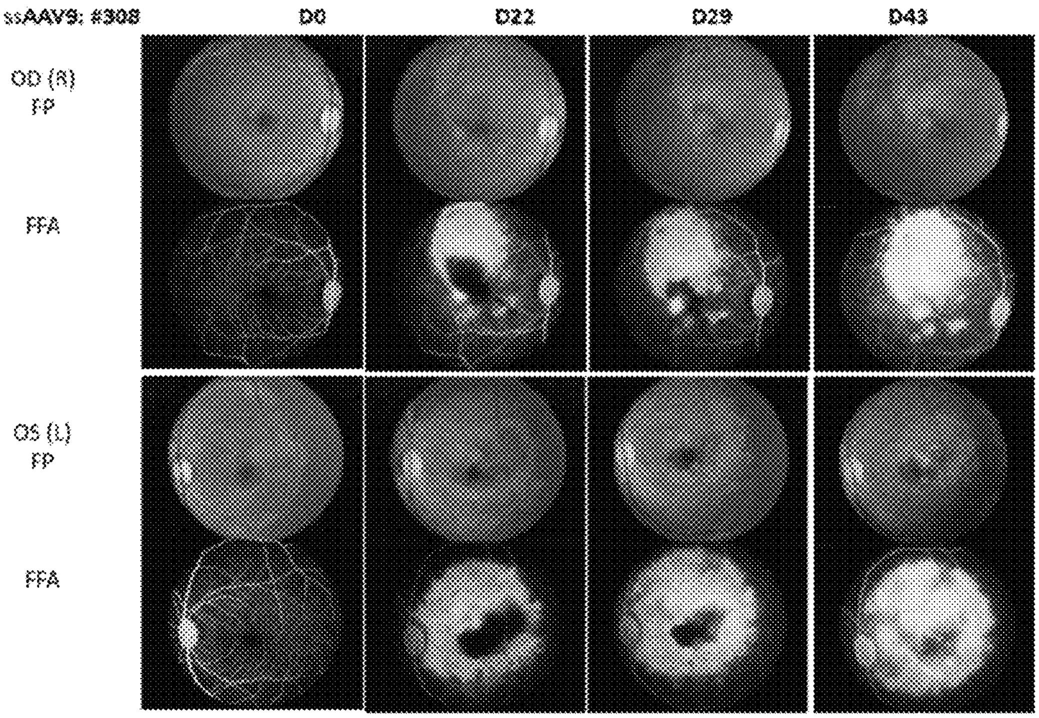
Figure 16C:
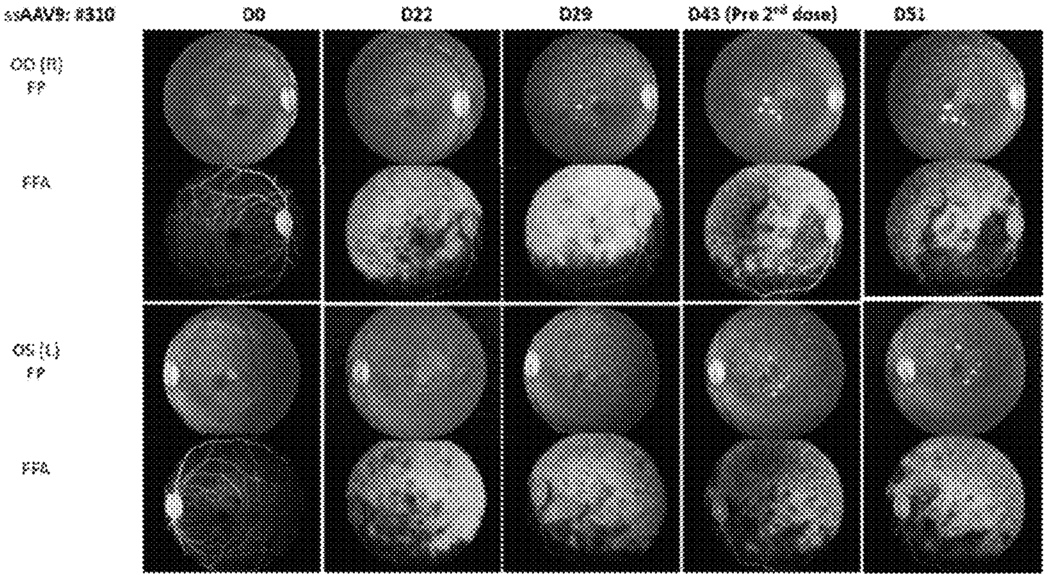

The expression of bi-valent Nb24 in eye tissues is shown in FIGS. 6A-6J, which shows that the administration of AAV.LGP-Nb24 achieved at least comparable and even higher expression of bi-valent Nb24 as compared to the reference (AAV.7m8-Nb24) throughout the eye compartments including retina and choroid where CNV occurs. As shown in FIG. 7, Nb24 was not expressed in the peripheral tissues (FIGS. 7A-G); and was not significantly expressed in sera (FIG. 7H).

Fundus fluorescein angiography (FFA) was used as the major in vivo endpoint for evaluation of fluorescein leakage of the RNV (Li et. al, 2018 and Cao et. al., 2018). Slit lamp microscopy and color fundus photography were performed to record ocular responses to the treatment as well. The images were shown in FIGS. 8-16. As compared with the clinical dose of Eylea® (2 mg/eye) (FIGS. 9A-9B), AAV2.LAE-Nb24 (FIGS. 10A-10B), AAV.RH10-Nb24 (FIGS. 11A-11B) and AAV2.LGP-Nb24 (FIGS. 12A-12B) provide partial or robust therapeutic efficacy in laser induced NHP CNV model, among which AAV2.LGP-Nb24 provided much robust therapeutic efficacy. The reference rAAV (AAV.7m8-Nb24) caused obvious ocular inflammatory response (evidenced by severe fluoresceine leakage in the anterior chamber) in 3 of 4 treated eyes (see FIGS. 13A-13B), which occurred in none of the monkey treated with any of AAV.GKG-Nb24, AAV.LAE-Nb24, AAV.LGP-Nb24, and AAV.NSP-Nb24. AAV9-Nb24 induced extensive choroidal leakage 7-14 days post sub-retinal injection (see FIGS. 16A-16C).

It can be seen that the rAAV comprising the modified capsid polypeptide achieved superior ocular transduction, robust transgene expression (evidenced by high levels of bi-valent Nb24 in ocular and surrounding tissues meaning robust blockage of retinal neovascularization), safety (evidenced by minimalized peripheral Nb24 expression), and therapeutic effect (evidenced by reduced leakage in retina).

SEQUENCES

```
SEQ ID NO: 1 capsid AAV2
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
```

-continued

FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNRQAATADVNTQGVLPGMVWQDRDVY
LQGPIWAKIPHTDGHFHPSPLMGGFGLKHPPPQILIKNTPVPANPSTTFSAAKFASFITQYSTGQVSV
EIEWELQKENSKRWNPEIQYTSNYNKSVNVDFTVDTNGVYSEPRPIGTRYLTRNL

SEQ ID NO: 2 capsid AAV2_GKG, obtained by inserting SEQ ID NO: 10 between positions 587 and 588 of SEQ ID NO: 1
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNAAAGKGPTTKAARQAATADVNTQGV
LPGMVWQDRDVYLQGPIWAKIPHTDGHFHPSPLMGGFGLKHPPPQILIKNTPVPANPSTTFSAAKFAS
FITQYSTGQVSVEIEWELQKENSKRWNPEIQYTSNYNKSVNVDFTVDTNGVYSEPRPIGTRYLTRNL SEQ ID NO: 3 capsid AAV2_LAE obtained by inserting SEQ ID NO: 11 between positions 587 and 588 of SEQ ID NO: 1
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNAAALAEPSRPAARQAATADVNTQGV
LPGMVWQDRDVYLQGPIWAKIPHTDGHFHPSPLMGGFGLKHPPPQILIKNTPVPANPSTTFSAAKFAS
FITQYSTGQVSVEIEWELQKENSKRWNPEIQYTSNYNKSVNVDFTVDTNGVYSEPRPIGTRYLTRNL SEQ ID NO: 4 capsid AAV2_LGP obtained by inserting SEQ ID NO: 12 between positions 587 and 588 of SEQ ID NO: 1
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNALALGPPSKPAARQAATADVNTQGV
LPGMVWQDRDVYLQGPIWAKIPHTDGHFHPSPLMGGFGLKHPPPQILIKNTPVPANPSTTFSAAKFAS
FITQYSTGQVSVEIEWELQKENSKRWNPEIQYTSNYNKSVNVDFTVDTNGVYSEPRPIGTRYLTRNL SEQ ID NO: 5 capsid AAV2_NSP obtained by inserting SEQ ID NO: 13 between positions 587 and 588 of SEQ ID NO: 1
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNAAGNSPTGRNAARQAATADVNTQGV
LPGMVWQDRDVYLQGPIWAKIPHTDGHFHPSPLMGGFGLKHPPPQILIKNTPVPANPSTTFSAAKFAS
FITQYSTGQVSVEIEWELQKENSKRWNPEIQYTSNYNKSVNVDFTVDTNGVYSEPRPIGTRYLTRNL SEQ ID NO: 6 inserted peptide_GKG
GKGPTTK SEQ ID NO: 7 inserted peptide_LAE
LAEPSRP SEQ ID NO: 8 inserted peptide_LGP
LGPPSKP SEQ ID NO: 9 inserted peptide_NSP
NSPTGRN SEQ ID NO: 10 inserted peptide_GKG full
AAAGKGPTTKAA SEQ ID NO: 11 inserted peptide_LAE full
AAALAEPSRPAA SEQ ID NO: 12 inserted peptide_LGP full
ALALGPPSKPAA SEQ ID NO: 13 inserted peptide_NSP full
AAGNSPTGRNAA SEQ ID NO: 14 coding sequence_AAV2 GKG
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACGCCGCCG
CCGGCAAGGGCCCCACCACCAAGGCCGCCAGACAAGCAGCTACCGCAGATGTCAACACACAAGGCGTT
CTTCCAGGCATGGTCTGGCAGGACAGAGATGTGTACCTTCAGGGGCCCATCTGGGCAAAGATTCCACA
CACGGACGGACATTTTCACCCCTCTCCCCTCATGGGTGGATTCGGACTTAAACACCCTCCTCCACAGA
TTCTCATCAAGAACACCCCAGTACCTGCGAATCCTTCGACCACCTTCAGTGCGGCAAAGTTTGCTTCC
TTCATCACACAGTACTCCACGGGACAGGTCAGCGTGGAGATCGAGTGGGAGCTGCAGAAGGAAAACAG
CAAACGCTGGAATCCCGAAATTCAGTACACTTCCAACTACAACAAGTCTGTTAATGTGGACTTTACTG
TGGACACTAATGGCGTGTATTCAGAGCCTCGCCCCATTGGCACCAGATACCTGACTCGTAATCTGTAA SEQ ID NO: 15 coding sequence_AAV2_LAE
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACGCCGCCG
CCCTGGCCGAGCCCAGCAGGCCCGCCGCCAGACAAGCAGCTACCGCAGATGTCAACACACAAGGCGTT
CTTCCAGGCATGGTCTGGCAGGACAGAGATGTGTACCTTCAGGGGCCCATCTGGGCAAAGATTCCACA
CACGGACGGACATTTTCACCCCTCTCCCCTCATGGGTGGATTCGGACTTAAACACCCTCCTCCACAGA
TTCTCATCAAGAACACCCCAGTACCTGCGAATCCTTCGACCACCTTCAGTGCGGCAAAGTTTGCTTCC
TTCATCACACAGTACTCCACGGGACAGGTCAGCGTGGAGATCGAGTGGGAGCTGCAGAAGGAAAACAG
CAAACGCTGGAATCCCGAAATTCAGTACACTTCCAACTACAACAAGTCTGTTAATGTGGACTTTACTG
TGGACACTAATGGCGTGTATTCAGAGCCTCGCCCCATTGGCACCAGATACCTGACTCGTAATCTGTAA -continued SEQ ID NO: 16 coding sequence_AAV2_LGP
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACGCCCTGG
CCCTGGGCCCCCCCAGCAAGCCCGCCGCCAGACAAGCAGCTACCGCAGATGTCAACACACAAGGCGTT
CTTCCAGGCATGGTCTGGCAGGACAGAGATGTGTACCTTCAGGGGCCCATCTGGGCAAAGATTCCACA
CACGGACGGACATTTTCACCCCTCTCCCCTCATGGGTGGATTCGGACTTAAACACCCTCCTCCACAGA
TTCTCATCAAGAACACCCCAGTACCTGCGAATCCTTCGACCACCTTCAGTGCGGCAAAGTTTGCTTCC
TTCATCACACAGTACTCCACGGGACAGGTCAGCGTGGAGATCGAGTGGGAGCTGCAGAAGGAAAACAG
CAAACGCTGGAATCCCGAAATTCAGTACACTTCCAACTACAACAAGTCTGTTAATGTGGACTTTACTG
TGGACACTAATGGCGTGTATTCAGAGCCTCGCCCCATTGGCACCAGATACCTGACTCGTAATCTGTAA SEQ ID NO: 17 coding sequence_AAV2_NSP
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACGCCGCCG
GCAACAGCCCCACCGGCAGGAACGCCGCCAGACAAGCAGCTACCGCAGATGTCAACACACAAGGCGTT
CTTCCAGGCATGGTCTGGCAGGACAGAGATGTGTACCTTCAGGGGCCCATCTGGGCAAAGATTCCACA
CACGGACGGACATTTTCACCCCTCTCCCCTCATGGGTGGATTCGGACTTAAACACCCTCCTCCACAGA
TTCTCATCAAGAACACCCCAGTACCTGCGAATCCTTCGACCACCTTCAGTGCGGCAAAGTTTGCTTCC
TTCATCACACAGTACTCCACGGGACAGGTCAGCGTGGAGATCGAGTGGGAGCTGCAGAAGGAAAACAG
CAAACGCTGGAATCCCGAAATTCAGTACACTTCCAACTACAACAAGTCTGTTAATGTGGACTTTACTG
TGGACACTAATGGCGTGTATTCAGAGCCTCGCCCCATTGGCACCAGATACCTGACTCGTAATCTGTAA SEQ ID NO: 18 AAV9 capsid
MAADGYLPDWLEDNLSEGIREWWALKPGAPQPKANQQHQDNARGLVLPGYKYLGPGNGLDKGEPVNAA
DAAALEHDKAYDQQLKAGDNPYLKYNHADAEFQERLKEDTSFGGNLGRAVFQAKKRLLEPLGLVEEAA
KTAPGKKRPVEQSPQEPDSSAGIGKSGAQPAKKRLNFGQTGDTESVPDPQPIGEPPAAPSGVGSLTMA
SGGGAPVADNNEGADGVGSSSGNWHCDSQWLGDRVITTSTRTWALPTYNNHLYKQISNSTSGGSSNDN
AYFGYSTPWGYFDFNRFHCHFSPRDWQRLINNNWGFRPKRLNFKLFNIQVKEVTDNNGVKTIANNLTS
TVQVFTDSDYQLPYVLGSAHEGCLPPFPADVFMIPQYGYLTLNDGSQAVGRSSFYCLEYFPSQMLRTG
NNFQFSYEFENVPFHSSYAHSQSLDRLMNPLIDQYLYYLSKTINGSGQNQQTLKFSVAGPSNMAVQGR -continued

```
NYIPGPSYRQQRVSTTVTQNNNSEFAWPGASSWALNGRNSLMNPGPAMASHKEGEDRFFPLSGSLIFG
KQGTGRDNVDADKVMITNEEEIKTTNPVATESYGQVATNHQSAQAQAQTGWVQNQGILPGMVWQDRDV
YLQGPIWAKIPHTDGNFHPSPLMGGFGMKHPPPQILIKNTPVPADPPTAFNKDKLNSFITQYSTGQVS
VEIEWELQKENSKRWNPEIQYTSNYYKSNNVEFAVNTEGVYSEPRPIGTRYLTRNL

SEQ ID NO: 19 rAAV genome encoding GFP
ACTCCATCACTAGGGGTTCCTTGTAGTTAATGATTAACCCGCCATGCTACTTATCTACCAGGGTAATG
GGGATCCTCTAGAACTATAGCTAGTCGACATAACGCGTCAATTGCTAGTCGACATTGATTATTGACTA
GTTATTAATAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATAATGACGTA
TGTTCCCATAGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAATGACGGTAAA
TGGCCCGCCTGGCATTATGCCCAGTACATGACCTTATGGGACTTTCCTACTTGGCAGTACATCTACGT
ATTAGTCATCGCTATTACCATGGTCGAGGTGAGCCCCACGTTCTGCTTCACTCTCCCCATCTCCCCCC
CCTCCCCACCCCCAATTTTGTATTTATTTATTTTTTAATTATTTTGTGCAGCGATGGGGGGGGGGGG
GGGGGGGGGCGCGCGCCAGGCGGGGGGGGGGGGGGCGAGGGGGGGGGCGGGGCGAGGCGGAGAGGTGC
GGCGGCAGCCAATCAGAGCGGCGCGCTCCGAAAGTTTCCTTTTATGGCGAGGCGGCGGCGGCGGCGGC
CCTATAAAAAGCGAAGCGCGCGGCGGGCGGAAGCTTCGTTTAGTGAACCGTCAGATCGCCTGGAGACG
CCATCCACGCTGTTTTGACCTCCATAGAAGACACCGGGACCGATCCAGCCTCCGCGGATTCGAATCCC
GGCCGGGAACGGTGCATTGGAACGCGGATTCCCCGTGCCAAGAGTGACGTAAGTACCGCCTATAGAGT
CTATAGGCCCACAAAAAATGCTTTCTTCTTTTAATATACTTTTTTGTTTATCTTATTTCTAATACTTT
CCCTAATCTCTTTCTTTCAGGGCAATAATGATACAATGTATCATGCCTCTTTGCACCATTCTAAAGAA
TAACAGTGATAATTTCTGGGTTAAGGCAATAGCAATATTTCTGCATATAAATATTTCTGCATATAAAT
TGTAACTGATGTAAGAGGTTTCATATTGCTAATAGCAGCTACAATCCAGCTACCATTCTGCTTTTATT
TTATGGTTGGGATAAGGCTGGATTATTCTGAGTCCAAGCTAGGCCCTTTTGCTAATCATGTTCATACC
TCTTATCTTCCTCCCACAGCTCCTGGGCAACGTGCTGGTCTGTGTGCTGGCCCATCACTTTGGCAAAG
AATTGAGCTCCTTCCTACTCAAAGCCACATGAATAGGAGGAGCCACCATGAGTCCTGCCCAGTTCCTG
TTTCTGTTAGTGCTCTGGATTCGGGAAACCAACGGTGATGTTGTGACCGGTGCCGCCACCATGGTGAG
CAAGGGCGAGGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTGAAGTTCATT
TGCACCACCGGCAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCCCGAAGGCTACG
TCCAGGAGCGCACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAAGAACGGCA
TCAAGGTGAACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCACCCAGTCCGC
CCTGAGCAAAGACCCCAACGAGAAGCGCGATCACATGGTCCTGCTGGAGTTCGTGACCGCCGCCGGGA
TCACTCTCGGCATGGACGAGCTGTACAAGTAATAGTAATAGTGTACAGGTACCTCGATGGATTTCCAA
GGTTAATTCATTGGAATTGAAAATTAACAGAGATCTAGAGCTGAATTCCTGCAGCCAGGGGGATCAGC
CTGGGTGGCATCCCTGTGACCCCTCCCCAGTGCCTCTCCTGGCCCTGGAAGTTGCCACTCCAGTGCCC
ACCAGCCTTGTCCTAATAAAATTAAGTTGCATCATTTTGTCTGACTAGGTGTCCTTCTATAATATTAT
GGGGTGGAGGGGGGTGGTATGGAGCAAGGGGCAAGTTGGGAAGACAACCTGTAGGGCCTGCGGGGTCT
ATTGGGAACCAAGCTGGAGTGCAGTGGCACAATCTTGGCTCACTGCAATCTCCGCCTCCTGGGTTCAA
GCGATTCTCCTGCCTCAGCCTCCCGAGTTGTTGGGATTCCAGGCATGCATGACCAGGCTCAGCTAATT
TTTGTTTTTTTGGTAGAGACGGGGTTTCACCATATTGGCCAGGCTGGTCTCCAACTCCTAATCTCAGG
TGATCTACCCACCTTGGCCTCCCAAATTGCTGGGATTACAGGCGTGAACCACTGCTCCCTTCCCTGTC
CTTCGGACCGAGCGGCCGCGCCTAGGTAGATAAGTAGCATGGCGGGTTAATCATTAACTACAAGGAAC
CCCTAGTGATGGAGTTGGCCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGCGCGCAGCCCTGCCTGCAG
GCATTTAATTAACCTAATTCG

SEQ ID NO: 20 rAAV genome encoding bi-valent Nb24 construct
CAATTGACATTATTGAAGCATTTATCAGGGTTATTGTCTCAGACTGCGCGCTCGCTCGCTCACTGAGG
CCGCCCGGGCAAAGCCCGGGCGTCGGGCGACCTTTGGTCGCCCGGCCTCAGTGAGCGAGCGAGCGCGC
AGAGAGGGAGTGGCCAACTCCATCACTAGGGGTTCCTTGTAGTTAATGATTAACCCGCCATGCTACTT
ATCTACCAGGGTAATGGGGATCCTCTAGAACTATAGCTAGTCGACATAACGCGTCAATTGCTAGTCGA
CATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATTGA
CGTCAATAATGACGTATGTTCCCATAGTAACGCCAATAGGGACTTTCCATTGACGTCAATGGGTGGAG
TATTTACGGTAAACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGACTTTCCTACTT
GGCAGTACATCTACGTATTAGTCATCGCTATTACCATGGTCGAGGTGAGCCCCACGTTCTGCTTCACT
CTCCCCATCTCCCCCCCCTCCCCACCCCCAATTTTGTATTTATTTATTTTTTAATTATTTTGTGCAGC
GATGGGGGCGGGGGGGGGGGGGGGGGGCGCGCCAGGCGGGGCGGGGGGGGCGAGGGGCGGGGCGGGG
CGAGGCGGAGAGGTGCGGCGGCAGCCAATCAGAGCGGCGCGCTCCGAAAGTTTCCTTTTATGGCGAGG
CGGCGGCGGCGGCCCTATAAAAAGCGAAGCGCGCGGCGGGCGGAAGCTTCGTTTAGTGAACCGTC
AGATCGCCTGGAGACGCCATCCACGCTGTTTTGACCTCCATAGAAGACACCGGGACCGATCCAGCCTC
CGCGGATTCGAATCCCGGCCGGGAACGGTGCATTGGAACGCGGATTCCCCGTGCCAAGAGTGACGTAA
GTACCGCCTATAGAGTCTATAGGCCCACAAAAAATGCTTTCTTCTTTTAATATACTTTTTTGTTTATC
TTATTTCTAATACTTTCCCTAATCTCTTTCTTTCAGGGCAATAATGATACAATGTATCATGCCTCTTT
GCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTA
CCATTCTGCTTTTATTTTATGGTTGGGATAAGGCTGGATTATTCTGAGTCCAAGCTAGGCCCTTTTGC
TAATCATGTTCATACCTCTTATCTTCCTCCCACAGCTCCTGGGCAACGTGCTGGTCTGTGTGCTGGCC
CATCACTTTGGCAAAGAATTGAGCTCCTTCCTACTCAAAGCCACATGAATAGGAGGAGCCACCATGAG
TCCTGCCCAGTTCCTGTTTCTGTTAGTGCTCTGGATTCGGGAAACCAACGGTGATGTTGTGACCGGTG
CCGCCACCATGAAGTACCTGCTGCCCACCGCCGCCGCCGGCCTGCTGCTGCTGGCCGCCCAGCCCGCC
ATGGCCGAGGTGCAGCTGCAGGAGAGCGGCGGCGGCCTGGTGCAGCCCGGCGGCAGCCTGAGGCTGAG
```

-continued

CTGCACCGCCAGCGGCTTCACCTTCGACGACCCCGACGTGGGCTGGTTCAGGCAGGCCCCCGGCAACG
AGTGCGAGCTGGTGAGCACCATCAGCAAGGACGGCAGCACCTACTACACCGACAGCGTGAAGGGCAGG
TTCACCATCAGCAGGGACTACGCCAAGAACACCGTGTACCTGCAGATGAACAGCCTGAGGGCCGAGGA
CACCGCCGTGTACTACTGCGCCGCCGACAGCAACCCCATCGCCCCCATCAGGACCTGCCTGGGCTGGT
ACAACTACTGGGGCCAGGGCACCCTGGTGACCGTGAGCAGCGGAGGAGGCGGCTCTGGCGGAGGCGGC
TCTGAAGTGCAACTGCAGGAGTCCGGTGGGGGTCTGGTTCAGCCCGGCGGATCCCTGCGGCTTAGCTG
TACCGCGTCCGGTTTCACCTTCGATGACCCTGACGTGGGCTGGTTCCGTCAGGCCCCAGGCAACGAGT
GTGAACTGGTGTCCACCATCTCCAAGGATGGGTCCACCTACTATACCGATTCTGTGAAAGGCCGCTTT
ACCATCAGTCGCGATTACGCTAAGAATACCGTGTACTTGCAGATGAATTCCCTCCGTGCCGAGGACAC
CGCGGTTTACTATTGTGCCGCAGACAGCAACCCTATTGCTCCCATCAGAACCTGCCTTGGTTGGTACA
ATTACTGGGGTCAGGGAACCTTGGTCACAGTGTCTAGCTAATAGTGTACAGGTACCTCGATGGATTTC
CAAGGTTAATTCATTGGAATTGAAAATTAACAGAGATCTAGAGCTGAATTCCTGCAGCCAGGGGGATC
AGCCTGGGTGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTATAATAT
TATGGGGTGGAGGGGGGTGGTATGGAGCAAGGGGCAAGTTGGGAAGACAACCTGTAGGGCCTGCGGGG
TCTATTGGGAACCAAGCTGGAGTGCAGTGGCACAATCTTGGCTCACTGCAATCTCCGCCTCCTGGGTT
CAAGCGATTCTCCTGCCTCAGCCTCCCGAGTTGTTGGGATTCCAGGCATGCATGACCAGGCTCAGCTA
ATTTTTGTTTTTTTGGTAGAGACGGGGTTTCACCATATTGGCCAGGCTGGTCTCCAACTCCTAATCTC
AGGTGATCTACCCACCTTGGCCTCCCAAATTGCTGGGATTACAGGCGTGAACCACTGCTCCCTTCCCT
GTCCTTCGGACCGAGCGGCCGCGGTACTAATTAACTAATAAAGCACAGAAGAGGAAAAAATCAAAGCT
AGATGGATGATAGATACATAGATAGATAGGAAGATTTTTTTTAATGACTCAAGGGAGTCCTGAAAGGA
AATACCAGACTTGTCTTTCTGACTACAGATGAACAGACATAAAACAAGTGTGCCTATTTTCCATTGAA
GAAAAACAAGCATTTTTTCTAAAGCCAGAAAAACCTACATCTGAAAAGAAAAAAGAAACTATTCTAAG
TTAAGAAAATAATTCTTTCTTGGATAAATTATGTCAACTTTTAACTTCCTAGAAATTGTAGGCATTAT
TTATTAGAAGTCAGTAACCAACTCTAGCTTTTTCCTTGTAGAAGTCCCTGGGAAAGGCCTACCCAAAC
ATAAAATCCTTACTGTTGAATACAATTGTTACTAATTGACAAATTCAGGCCTTTGTCACTCTCACATA
TACTTTGTGCATACTTTTTCATTTAACAAATGAAAAGAATAATATTAGTCCATTTAGTTTTCACCACA
ACATTATAATGTAATATATTGTTAAATACAAAGAAACCTAAAAAAATCTCAAATTCATCATGACTGAA
TAGAAACTTTGAATTGATTTTCCTATATCTAATGAAGAGCCCTAGCTTTAAAACAAAATTGATGAAAC
CTAAAAGAATCTTTTCTTTTTTTTTTTTTTTTTTTGAGATGGAGTCTCGCTCTTTCGCCCAGACTGGA
GTGCAGTGGCACTATCTCGGCTCACTTGCAAGCTCCGCCTCCCGAGTTCACGCCATTCTTCTGCCTCA
GCCTCCCGAGTAGCTGGGACTACAGGCGCCCGCCATCACGCCCGGCTAATTTTTTGTATCTTTAGTAG
AGACGGGGTTTCACCGTGTGCCAGGGTGGTCTCGATCTCCTGACCTCGTCATCCGCCCACCTCGGCCT
CCCAAAGTGCTGGGATTACAGTCATGAGCCACCGCGCCCGGCCAAGAATCTTTTCTTACAGTACTAAT
GAGGCATTTTGCATATGTGCATCCTACTAAAAGATTAATAGTTTAGAAATTAAAATATTTAATTCTCA
ATGATATCTGCATACTTAAAATTAATGTTTCTTAAGAAATACTTGAACAATTGCATCTTCTGGATTTG
CAAAGTAAAAATTTCTGCATTTTTCTCTGAAAACCTCTGGCATTAATTCTATATGAACATTCTATACT
GAGAGAAATAAACCTACATAATTGTTAGTCATTTCTAAATTTCCTGTTCTTCAAACTTTGAAACTCTG
TTTAGTCAGTCATCAACGGGCTCTGGCATGAGGGTAAATGCAAATATTTAGAGTAAGAGTTATAAATA
TGGTTTAGAGATTCTCTTTACTCGGTAAACAGAAAAATAGCCCCAATGATTTTTAAATGTTTTCTCAT
CTTTGTGGGAGAAGTTTAAAAATAGAGAGTAGTTAAGAAAAGTATTTTCTTTAGAAAGAATAAGTGTA
CTGATCGCGGCCGCGCCTAGGTAGATAAGTAGCATGGCGGGTTAATCATTAACTACAAGGAACCCCTA
GTGATGGAGTTGGCCACTCCCTCTCTGCGCGCTCGCTCGCTCACTGAGGCCGGGCGACCAAAGGTCGC
CCGACGCCCGGGCTTTGCCCGGGCGGCCTCAGTGAGCGAGCGAGCGCGCAGCCCTGCCTGCAGGCATT
TAATTAACCTAATTC

SEQ ID NO: 21 AAV2_7m8 amino acid sequence
MAADGYLPDWLEDTLSEGIRQWWKLKPGPPPPKPAERHKDDSRGLVLPGYKYLGPFNGLDKGEPVNEA
DAAALEHDKAYDRQLDSGDNPYLKYNHADAEFQERLKEDTSFGGNLGRAVFQAKKRVLEPLGLVEEPV
KTAPGKKRPVEHSPVEPDSSSGTGKAGQQPARKRLNFGQTGDADSVPDPQPLGQPPAAPSGLGTNTMA
TGSGAPMADNNEGADGVGNSSGNWHCDSTWMGDRVITTSTRTWALPTYNNHLYKQISSQSGASNDNHY
FGYSTPWGYFDFNRFHCHFSPRDWQRLINNNWGFRPKRLNFKLFNIQVKEVTQNDGTTTIANNLTSTV
QVFTDSEYQLPYVLGSAHQGCLPPFPADVFMVPQYGYLTLNNGSQAVGRSSFYCLEYFPSQMLRTGNN
FTFSYTFEDVPFHSSYAHSQSLDRLMNPLIDQYLYYLSRTNTPSGTTTQSRLQFSQAGASDIRDQSRN
WLPGPCYRQQRVSKTSADNNNSEYSWTGATKYHLNGRDSLVNPGPAMASHKDDEEKFFPQSGVLIFGK
QGSEKTNVDIEKVMITDEEEIRTTNPVATEQYGSVSTNLQRGNLALGETTRPARQAATADVNTQGVLP
GMVWQDRDVYLQGPIWAKIPHTDGHFHPSPLMGGFGLKHPPPQILIKNTPVPANPSTTFSAAKFASFI
TQYSTGQVSVEIEWELQKENSKRWNPEIQYTSNYNKSVNVDFTVDTNGVYSEPRPIGTRYLTRNL SEQ ID NO: 22 AAV_RH10 amino acid sequence
1MAADGYLPDWLEDNLSEGIREWWDLKPGAPKPKANQQKQDDGRGLVLPGYKYLGPFNGLDKGEPVNA
ADAAALEHDKAYDQQLKAGDNPYLRYNHADAEFQERLQEDTSFGGNLGRAVFQAKKRVLEPLGLVEEG
AKTAPGKKRPVEPSPQRSPDSSTGIGKKGQQPAKKRLNFGQTGDSESVPDPQPIGEPPAGPSGLGSGT
MAAGGGAPMADNNEGADGVGSSSGNWHCDSTWLGDRVITTSTRTWALPTYNNHLYKQISNGTSGGSTN
DNTYFGYSTPWGYFDFNRFHCHFSPRDWQRLINNNWGFRPKRLNFKLFNIQVKEVTQNEGTKTIANNL
TSTIQVFTDSEYQLPYVLGSAHQGCLPPFPADVFMIPQYGYLTLNNGSQAVGRSSFYCLEYFPSQMLR
TGNNFEFSYQFEDVPFHSSYAHSQSLDRLMNPLIDQYLYYLSRTQSTGGTAGTQQLLFSQAGPNNMSA
QAKNWLPGPCYRQQRVSTTLSQNNNSNFAWTGATKYHLNGRDSLVNPGVAMATHKDDEERFFPSSGVL
MFGKQGAGKDNVDYSSVMLTSEEEIKTTNPVATEQYGVVADNLQQQNAAPIVGAVNSQGALPGMVWQN
RDVYLQGPIWAKIPHTDGNFHPSPLMGGFGLKHPPPQILIKNTPVPADPPTTFSQAKLASFITQYSTG
QVSVEIEWELQKENSKRWNPEIQYTSNYYKSTNVDFAVNTDGTYSEPRPIGTRYLTRNL SEQ ID NO: 23 nucleotide sequence encoding AAV2 REP
ATGCCGGGGTTTTACGAGATTGTGATTAAGGTCCCCAGCGACCTTGACGAGCATCTGCCCGGCATTTC
TGACAGCTTTGTGAACTGGGTGGCCGAGAAGGAATGGGAGTTGCCGCCAGATTCTGACATGGATCTGA
ATCTGATTGAGCAGGCACCCCTGACCGTGGCCGAGAAGCTGCAGCGCGACTTTCTGACGGAATGGCGC
CGTGTGAGTAAGGCCCCGGAGGCTCTTTTCTTTGTGCAATTTGAGAAGGGAGAGAGCTACTTCCACAT
GCACGTGCTCGTGGAAACCACCGGGGTGAAATCCATGGTTTTGGGACGTTTCCTGAGTCAGATTCGCG
AAAAACTGATTCAGAGAATTTACCGCGGGATCGAGCCGACTTTGCCAAACTGGTTCGCGGTCACAAAG -continued ACCAGAAATGGCGCCGGAGGCGGGAACAAGGTGGTGGATGAGTGCTACATCCCCAATTACTTGCTCCC
CAAAACCCAGCCTGAGCTCCAGTGGGCGTGGACTAATATGGAACAGTATTTAAGCGCCTGTTTGAATC
TCACGGAGCGTAAACGGTTGGTGGCGCAGCATCTGACGCACGTGTCGCAGACGCAGGAGCAGAACAAA
GAGAATCAGAATCCCAATTCTGATGCGCCGGTGATCAGATCAAAAACTTCAGCCAGGTACATGGAGCT
GGTCGGGTGGCTCGTGGACAAGGGGATTACCTCGGAGAAGCAGTGGATCCAGGAGGACCAGGCCTCAT
ACATCTCCTTCAATGCGGCCTCCAACTCGCGGTCCCAAATCAAGGCTGCCTTGGACAATGCGGGAAAG
ATTATGAGCCTGACTAAAACCGCCCCCGACTACCTGGTGGGCCAGCAGCCCGTGGAGGACATTTCCAG
CAATCGGATTTATAAAATTTTGGAACTAAACGGGTACGATCCCCAATATGCGGCTTCCGTCTTTCTGG
GATGGGCCACGAAAAAGTTCGGCAAGAGGAACACCATCTGGCTGTTTGGGCCTGCAACTACCGGGAAG
ACCAACATCGCGGAGGCCATAGCCCACACTGTGCCCTTCTACGGGTGCGTAAACTGGACCAATGAGAA
CTTTCCCTTCAACGACTGTGTCGACAAGATGGTGATCTGGTGGGAGGAGGGGAAGATGACCGCCAAGG
TCGTGGAGTCGGCCAAAGCCATTCTCGGAGGAAGCAAGGTGCGCGTGGACCAGAAATGCAAGTCCTCG
GCCCAGATAGACCCGACTCCCGTGATCGTCACCTCCAACACCAACATGTGCGCCGTGATTGACGGGAA
CTCAACGACCTTCGAACACCAGCAGCCGTTGCAAGACCGGATGTTCAAATTTGAACTCACCCGCCGTC
TGGATCATGACTTTGGGAAGGTCACCAAGCAGGAAGTCAAAGACTTTTTCCGGTGGGCAAAGGATCAC
GTGGTTGAGGTGGAGCATGAATTCTACGTCAAAAAGGGTGGAGCCAAGAAAAGACCCGCCCCCAGTGA
CGCAGATATAAGTGAGCCCAAACGGGTGCGCGAGTCAGTTGCGCAGCCATCGACGTCAGACGCGGAAG
CTTCGATCAACTACGCAGACAGGTACCAAAACAAATGTTCTCGTCACGTGGGCATGAATCTGATGCTG
TTTCCCTGCAGACAATGCGAGAGAATGAATCAGAATTCAAATATCTGCTTCACTCACGGACAGAAAGA
CTGTTTAGAGTGCTTTCCCGTGTCAGAATCTCAACCCGTTTCTGTCGTCAAAAAGGCGTATCAGAAAC
TGTGCTACATTCATCATATCATGGGAAAGGTGCCAGACGCTTGCACTGCCTGCGATCTGGTCAATGTG
GATTTGGATGACTGCATCTTTGAACAATAA SEQ ID NO: 24 (Nb amino acid sequence)
EVQLQESGGGLVQPGGSLRLSCTASGFTFDDPDVGWFRQAPGNECELVSTISKDGSTYYTDSVKGRFT
ISRDYAKNTVYLQMNSLRAEDTAVYYCAADSNPIAPIRTCLGWYNYWGQGTLVTVSS SEQ ID NO: 25 coding sequence AAV2 capsid
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACAGACAAG
CAGCTACCGCAGATGTCAACACACAAGGCGTTCTTCCAGGCATGGTCTGGCAGGACAGAGATGTGTAC
CTTCAGGGGCCCATCTGGGCAAAGATTCCACACACGGACGGACATTTTCACCCCTCTCCCCTCATGGG
TGGATTCGGACTTAAACACCCTCCTCCACAGATTCTCATCAAGAACACCCCAGTACCTGCGAATCCTT
CGACCACCTTCAGTGCGGCAAAGTTTGCTTCCTTCATCACACAGTACTCCACGGGACAGGTCAGCGTG
GAGATCGAGTGGGAGCTGCAGAAGGAAAACAGCAAACGCTGGAATCCCGAAATTCAGTACACTTCCAA
CTACAACAAGTCTGTTAATGTGGACTTTACTGTGGACACTAATGGCGTGTATTCAGAGCCTCGCCCCA
TTGGCACCAGATACCTGACTCGTAATCTGTAA SEQ ID NO: 26 coding sequence AAV2_7m8
ATGGCTGCCGATGGTTATCTTCCAGATTGGCTCGAGGACACTCTCTCTGAAGGAATAAGACAGTGGTG
GAAGCTCAAACCTGGCCCACCACCACCAAAGCCCGCAGAGCGGCATAAGGACGACAGCAGGGGTCTTG
TGCTTCCTGGGTACAAGTACCTCGGACCCTTCAACGGACTCGACAAGGGAGAGCCGGTCAACGAGGCA
GACGCCGCGGCCCTCGAGCACGACAAAGCCTACGACCGGCAGCTCGACAGCGGAGACAACCCGTACCT
CAAGTACAACCACGCCGACGCGGAGTTTCAGGAGCGCCTTAAAGAAGATACGTCTTTTGGGGGCAACC
TCGGACGAGCAGTCTTCCAGGCGAAAAAGAGGGTTCTTGAACCTCTGGGCCTGGTTGAGGAACCTGTT
AAGACGGCTCCGGGAAAAAAGAGGCCGGTAGAGCACTCTCCTGTGGAGCCAGACTCCTCCTCGGGAAC
CGGAAAGGCGGGCCAGCAGCCTGCAAGAAAAAGATTGAATTTTGGTCAGACTGGAGACGCAGACTCAG
TACCTGACCCCCAGCCTCTCGGACAGCCACCAGCAGCCCCCTCTGGTCTGGGAACTAATACGATGGCT
ACAGGCAGTGGCGCACCAATGGCAGACAATAACGAGGGCGCCGACGGAGTGGGTAATTCCTCGGGAAA
TTGGCATTGCGATTCCACATGGATGGGCGACAGAGTCATCACCACCAGCACCCGAACCTGGGCCCTGC
CCACCTACAACAACCACCTCTACAAACAAATTTCCAGCCAATCAGGAGCCTCGAACGACAATCACTAC
TTTGGCTACAGCACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTT
CAGGTGTTTACTGACTCGGAGTACCAGCTCCCGTACGTCCTCGGCTCGGCGCATCAAGGATGCCTCCC -continued

```
GCCGTTCCCAGCAGACGTCTTCATGGTGCCACAGTATGGATACCTCACCCTGAACAACGGGAGTCAGG
CAGTAGGACGCTCTTCATTTTACTGCCTGGAGTACTTTCCTTCTCAGATGCTGCGTACCGGAAACAAC
TTTACCTTCAGCTACACTTTTGAGGACGTTCCTTTCCACAGCAGCTACGCTCACAGCCAGAGTCTGGA
CCGTCTCATGAATCCTCTCATCGACCAGTACCTGTATTACTTGAGCAGAACAAACACTCCAAGTGGAA
CCACCACGCAGTCAAGGCTTCAGTTTTCTCAGGCCGGAGCGAGTGACATTCGGGACCAGTCTAGGAAC
TGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGG
CCATGGCAAGCCACAAGGACGATGAAGAAAAGTTTTTCCTCAGAGCGGGGTTCTCATCTTTGGGAAG
CAAGGCTCAGAGAAAACAAATGTGGACATTGAAAAGGTCATGATTACAGACGAAGAGGAAATCAGGAC
AACCAATCCCGTGGCTACGGAGCAGTATGGTTCTGTATCTACCAACCTCCAGAGAGGCAACCTAGCAC
TCGGCGAAACAACAAGACCTGCTAGACAAGCAGCTACCGCAGATGTCAACACACAAGGCGTTCTTCCA
GGCATGGTCTGGCAGGACAGAGATGTGTACCTTCAGGGGCCCATCTGGGCAAAGATTCCACACACGGA
CGGACATTTTCACCCCTCTCCCCTCATGGGTGGATTCGGACTTAAACACCCTCCTCCACAGATTCTCA
TCAAGAACACCCCAGTACCTGCGAATCCTTCGACCACCTTCAGTGCGGCAAAGTTTGCTTCCTTCATC
ACACAGTACTCCACGGGACAGGTCAGCGTGGAGATCGAGTGGGAGCTGCAGAAGGAAAACAGCAAACG
CTGGAATCCCGAAATTCAGTACACTTCCAACTACAACAAGTCTGTTAATGTGGACTTTACTGTGGACA
CTAATGGCGTGTATTCAGAGCCTCGCCCCATTGGCACCAGATACCTGACTCGTAATCTGTAA

SEQ ID NO: 27 coding sequence AAV_RH10
ATGGCTGCCGATGGTTATCTTCCAGATTGGCTCGAGGACAACCTCTCTGAGGGCATTCGC
GAGTGGTGGGACTTGAAACCTGGAGCCCCGAAACCCAAAGCCAACCAGCAAAAGCAGGAC
GACGGCCGGGGTCTGGTGCTTCCTGGCTACAAGTACCTCGGACCCTTCAACGGACTCGAC
AAGGGGGAGCCCGTCAACGCGGCGGACGCAGCGGCCCTCGAGCACGACAAGGCCTACGAC
CAGCAGCTCAAAGCGGGTGACAATCCGTACCTGCGGTATAACCACGCCGACGCCGAGTTT
CAGGAGCGTCTGCAAGAAGATACGTCTTTTGGGGGCAACCTCGGGCGAGCAGTCTTCCAG
GCCAAGAAGCGGGTTCTCGAACCTCTCGGTCTGGTTGAGGAAGGCGCTAAGACGGCTCCT
GGAAAGAAGAGACCGGTAGAGCCATCACCCCAGCGTTCTCCAGACTCCTCTACGGGCATC
GGCAAGAAAGGCCAGCAGCCCGCGAAAAAGAGACTCAACTTTGGGCAGACTGGCGACTCA
GAGTCAGTGCCCGACCCTCAACCAATCGGAGAACCCCCCGCAGGCCCCTCTGGTCTGGGA
TCTGGTACAATGGCTGCAGGCGGTGGCGCTCCAATGGCAGACAATAACGAAGGCGCCGAC
GGAGTGGGTAGTTCCTCAGGAAATTGGCATTGCGATTCCACATGGCTGGGCGACAGAGTC
ATCACCACCAGCACCCGAACCTGGGCCCTCCCCACCTACAACAACCACCTCTACAAGCAA
ATCTCCAACGGGACTTCGGGAGGAAGCACCAACGACAACACCTACTTCGGCTACAGCACC
CCCTGGGGGTATTTTGACTTTAACAGATTCCACTGCCACTTCTCACCACGTGACTGGCAG
CGACTCATCAACAACAACTGGGGATTCCGGCCCAAGAGACTCAACTTCAAGCTCTTCAAC
ATCCAGGTCAAGGAGGTCACGCAGAATGAAGGCACCAAGACCATCGCCAATAACCTTACC
AGCACGATTCAGGTCTTTACGGACTCGGAATACCAGCTCCCGTACGTCCTCGGCTCTGCG
CACCAGGGCTGCCTGCCTCCGTTCCCGGCGGACGTCTTCATGATTCCTCAGTACGGGTAC
CTGACTCTGAACAATGGCAGTCAGGCCGTGGGCCGTTCCTCCTTCTACTGCCTGGAGTAC
TTTCCTTCTCAAATGCTGAGAACGGGCAACAACTTTGAGTTCAGCTACCAGTTTGAGGAC
GTGCCTTTTCACAGCAGCTACGCGCACAGCCAAAGCCTGGACCGGCTGATGAACCCCCTC
ATCGACCAGTACCTGTACTACCTGTCTCGGACTCAGTCCACGGGAGGTACCGCAGGAACT
CAGCAGTTGCTATTTTCTCAGGCCGGGCCTAATAACATGTCGGCTCAGGCCAAAAACTGG
CTACCCGGGCCCTGCTACCGGCAGCAACGCGTCTCCACGACACTGTCGCAAAATAACAAC
AGCAACTTTGCCTGGACCGGTGCCACCAAGTATCATCTGAATGGCAGAGACTCTCTGGTA
AATCCCGGTGTCGCTATGGCAACCCACAAGGACGACGAAGAGCGATTTTTTCCGTCCAGC
GGAGTCTTAATGTTTGGGAAACAGGGAGCTGGAAAAGACAACGTGGACTATAGCAGCGTT
ATGCTAACCAGTGAGGAAGAAATTAAAACCACCAACCCAGTGGCCACAGAACAGTACGGC
GTGGTGGCCGATAACCTGCAACAGCAAAACGCCGCTCCTATTGTAGGGGCCGTCAACAGT
CAAGGAGCCTTACCTGGCATGGTCTGGCAGAACCGGGACGTGTACCTGCAGGGTCCTATC
TGGGCCAAGATTCCTCACACGGACGGAAACTTTCATCCCTCGCCGCTGATGGGAGGCTTT
GGACTGAAACACCCGCCTCCTCAGATCCTGATTAAGAATACACCTGTTCCCGCGGATCCT
CCAACTACCTTCAGTCAAGCTAAGCTGGCGTCGTTCATCACGCAGTACAGCACCGGACAG
GTCAGCGTGGAAATTGAATGGGAGCTGCAGAAAGAAAACAGCAAACGCTGGAACCCAGAG
ATTCAATACACTTCCAACTACTACAAATCTACAAATGTGGACTTTGCTGTTAACACAGAT
GGCACTTATTCTGAGCCTCGCCCCATCGGCACCCGTTACCTCACCCGTAATCTG
```

The invention claimed is:

1. A modified adeno-associated virus (AAV) capsid polypeptide comprising, as compared to the parental AAV capsid polypeptide, a peptide inserted into loop IV, and wherein the inserted peptide comprises the amino acid sequence of Formula I:

spacer1-X1-X2-X3-X4-X5-X6-X7-spacer2 (I), wherein the spacers 1 and 2 independently comprise one or more amino acids selected from A, L and G, and wherein X1-X2-X3-X4-X5-X6-X7 is the amino acid sequence selected from SEQ ID NO: 6, SEQ ID NO: 7, SEQ ID NO: 8 and SEQ ID NO: 9.

2. The modified AAV capsid polypeptide of claim 1, wherein the inserted peptide comprises the amino acid sequence of Formula II:

$$Y1-Y2-Y3-X1-X2-X3-X4-X5-X6-X7-Y4-Y5, \quad \text{(II)}$$

wherein spacer 1 consists of amino acids Y1, Y2 and Y3, spacer 2 consists of amino acids Y4 and Y5, wherein Y1, Y2, Y3, Y4 and Y5 are each independently selected from A, L and G.

3. The modified AAV capsid polypeptide of claim 1, wherein the inserted peptide comprises the amino acid sequence selected from SEQ ID NO: 10, SEQ ID NO: 11, SEQ ID NO: 12, and SEQ ID NO: 13.

4. The modified AAV capsid polypeptide of claim 1, wherein the parental AAV capsid polypeptide is an AAV2 capsid polypeptide comprising the amino acid sequence of SEQ ID NO: 1, amino acids 138-735 of SEQ ID NO: 1, or amino acids 203-735 of SEQ ID NO: 1, or a variant thereof which is at least 90% identical to SEQ ID NO: 1 over the full length, amino acids 138-735, or amino acids 203-735.

5. The modified AAV capsid polypeptide of claim 1, wherein the peptide is inserted between positions corresponding to positions 587 and 588 of SEQ ID NO: 1.

6. The modified AAV capsid polypeptide of claim 1, comprising the amino acid sequence selected from SEQ ID NOs: 2, 3, 4 and 5, amino acids 138-747 of SEQ ID NO: 2, 3, 4 or 5, or amino acids 203-747 of SEQ ID NO: 2, 3, 4 or 5.

7. A polynucleotide encoding the modified AAV capsid polypeptide of claim 1.

8. A vector comprising the polynucleotide of claim 7.

9. A host cell comprising the polynucleotide of claim 7.

10. A kit for packaging an rAAV comprising the polynucleotide of claim 7.

11. A recombinant adeno-associated virus (rAAV) comprising a modified AAV capsid polypeptide and a genome encoding a gene product, wherein the modified AAV capsid polypeptide comprises, as compared to the parental AAV capsid polypeptide, a peptide inserted into loop IV, and wherein the inserted peptide comprises the amino acid sequence of Formula I:

spacer1-*X*1-*X*2-*X*3-*X*4-*X*5-*X*6-*X*7-spacer2 (I), wherein the spacers 1 and 2 independently comprise one or more amino acids selected from A, L and G, and wherein X1-X2-X3-X4-X5-X6-X7 is the amino acid sequence selected from SEQ ID NO: 6, SEQ ID NO: 7, SEQ ID NO: 8 and SEQ ID NO: 9.

12. The rAAV of claim 11, wherein the inserted peptide comprises the amino acid sequence of Formula II:

Y1-Y2-Y3-X1-X2-X3-X4-X5-X6-X7-Y4-Y5 (II), wherein spacer 1 consists of amino acids Y1, Y2 and Y3, spacer 2 consists of amino acids Y4 and Y5, wherein Y1, Y2, Y3, Y4 and Y5 are independently selected from A, L and G.

13. The rAAV of claim 11, wherein the inserted peptide comprises the amino acid sequence selected from SEQ ID NO: 10, SEQ ID NO: 11, SEQ ID NO: 12 and SEQ ID NO: 13.

14. The rAAV of claim 11, wherein the parental AAV capsid polypeptide is an AAV2 capsid polypeptide comprising the amino acid sequence of SEQ ID NO:1, amino acids 138-735 of SEQ ID NO: 1, or amino acids 203-735 of SEQ ID NO: 1, or a variant thereof which is at least 90% identical to SEQ ID NO: 1 over the full length, amino acids 138-735, or amino acids 203-735.

15. The rAAV of claim 11, wherein the peptide is inserted between positions corresponding to positions 587 and 588 of SEQ ID NO: 1.

16. The rAAV of claim 11, wherein the modified AAV capsid polypeptide comprises the amino acid sequence selected from SEQ ID NOs: 2, 3, 4 and 5, amino acids 138-747 of SEQ ID NO: 2, 3, 4 or 5, or amino acids 203-747 of SEQ ID NO: 2, 3, 4 or 5.

17. A pharmaceutical composition comprising the rAAV of claim 11.

18. A method of treating a retinal disease comprising the administration of the rAAV of claim 11 to an eye of a subject in need thereof.

19. The modified AAV capsid polypeptide of claim 1, wherein the spacers 1 and 2 independently comprise one to ten amino acids selected from A, L and G.

20. The modified AAV capsid polypeptide of claim 1, wherein the spacers 1 and 2 independently comprise one to three amino acids selected from A, L and G.

* * * * *

SEQUENCE LISTING

```
Sequence total quantity: 27
SEQ ID NO: 1            moltype = AA  length = 735
FEATURE                 Location/Qualifiers
source                  1..735
                        mol_type = protein
                        organism = adeno-associated virus 2
SEQUENCE: 1
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
```

```
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 2            moltype = AA  length = 747
FEATURE                 Location/Qualifiers
REGION                  1..747
                        note = GKG
source                  1..747
                        mol_type = protein
                        organism = synthetic construct
SEQUENCE: 2
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNAAA GKGPTTKAAR  600
QAATADVNTQ GVLPGMVWQD RDVYLQGPIW AKIPHTDGHF HPSPLMGGFG LKHPPPQILI  660
KNTPVPANPS TTFSAAKFAS FITQYSTGQV SVEIEWELQK ENSKRWNPEI QYTSNYNKSV  720
NVDFTVDTNG VYSEPRPIGT RYLTRNL                                     747

SEQ ID NO: 3            moltype = AA  length = 747
FEATURE                 Location/Qualifiers
REGION                  1..747
                        note = LAE
source                  1..747
                        mol_type = protein
                        organism = synthetic construct
SEQUENCE: 3
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNAAA LAEPSRPAAR  600
QAATADVNTQ GVLPGMVWQD RDVYLQGPIW AKIPHTDGHF HPSPLMGGFG LKHPPPQILI  660
KNTPVPANPS TTFSAAKFAS FITQYSTGQV SVEIEWELQK ENSKRWNPEI QYTSNYNKSV  720
NVDFTVDTNG VYSEPRPIGT RYLTRNL                                     747

SEQ ID NO: 4            moltype = AA  length = 747
FEATURE                 Location/Qualifiers
REGION                  1..747
                        note = LGP
source                  1..747
                        mol_type = protein
                        organism = synthetic construct
SEQUENCE: 4
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNALA LGPPSKPAAR  600
QAATADVNTQ GVLPGMVWQD RDVYLQGPIW AKIPHTDGHF HPSPLMGGFG LKHPPPQILI  660
KNTPVPANPS TTFSAAKFAS FITQYSTGQV SVEIEWELQK ENSKRWNPEI QYTSNYNKSV  720
NVDFTVDTNG VYSEPRPIGT RYLTRNL                                     747

SEQ ID NO: 5            moltype = AA  length = 747
FEATURE                 Location/Qualifiers
REGION                  1..747
                        note = NSP
source                  1..747
                        mol_type = protein
                        organism = synthetic construct
SEQUENCE: 5
```

-continued

```
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNAAG NSPTGRNAAR  600
QAATADVNTQ GVLPGMVWQD RDVYLQGPIW AKIPHTDGHF HPSPLMGGFG LKHPPPQILI  660
KNTPVPANPS TTFSAAKFAS FITQYSTGQV SVEIEWELQK ENSKRWNPEI QYTSNYNKSV  720
NVDFTVDTNG VYSEPRPIGT RYLTRNL                                    747

SEQ ID NO: 6           moltype = AA  length = 7
FEATURE                Location/Qualifiers
REGION                 1..7
                       note = GKG insert
source                 1..7
                       mol_type = protein
                       organism = synthetic construct
SEQUENCE: 6
GKGPTTK                                                          7

SEQ ID NO: 7           moltype = AA  length = 7
FEATURE                Location/Qualifiers
REGION                 1..7
                       note = LAE insert
source                 1..7
                       mol_type = protein
                       organism = synthetic construct
SEQUENCE: 7
LAEPSRP                                                          7

SEQ ID NO: 8           moltype = AA  length = 7
FEATURE                Location/Qualifiers
REGION                 1..7
                       note = LGP insert
source                 1..7
                       mol_type = protein
                       organism = synthetic construct
SEQUENCE: 8
LGPPSKP                                                          7

SEQ ID NO: 9           moltype = AA  length = 7
FEATURE                Location/Qualifiers
REGION                 1..7
                       note = NSP insert
source                 1..7
                       mol_type = protein
                       organism = synthetic construct
SEQUENCE: 9
NSPTGRN                                                          7

SEQ ID NO: 10          moltype = AA  length = 12
FEATURE                Location/Qualifiers
REGION                 1..12
                       note = GKG full insert
source                 1..12
                       mol_type = protein
                       organism = synthetic construct
SEQUENCE: 10
AAAGKGPTTK AA                                                    12

SEQ ID NO: 11          moltype = AA  length = 12
FEATURE                Location/Qualifiers
REGION                 1..12
                       note = LAE full insert
source                 1..12
                       mol_type = protein
                       organism = synthetic construct
SEQUENCE: 11
AAALAEPSRP AA                                                    12

SEQ ID NO: 12          moltype = AA  length = 12
FEATURE                Location/Qualifiers
REGION                 1..12
                       note = LGP full insert
source                 1..12
```

```
                        mol_type = protein
                        organism = synthetic construct
SEQUENCE: 12
ALALGPPSKP AA                                                          12

SEQ ID NO: 13           moltype = AA  length = 12
FEATURE                 Location/Qualifiers
REGION                  1..12
                        note = NSP full insert
source                  1..12
                        mol_type = protein
                        organism = synthetic construct
SEQUENCE: 13
AAGNSPTGRN AA                                                          12

SEQ ID NO: 14           moltype = DNA  length = 2244
FEATURE                 Location/Qualifiers
misc_feature            1..2244
                        note = GKG coding sequence
source                  1..2244
                        mol_type = other DNA
                        organism = synthetic construct
SEQUENCE: 14
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cgccgccgcc ggcaagggcc ccaccaccaa ggccgccaga  1800
caagcagcta ccgcagatgt caacacacaa ggcgttcttc caggcatggt ctggcaggac  1860
agagatgtgt accttcaggg gcccatctgg gcaaagattc cacacacgga cggacatttt  1920
cacccctctc ccctcatggg tggattcgga cttaaacacc ctcctccaca gattctcatc  1980
aagaacaccc cagtacctgc gaatccttcg accaccttca gtgcggcaaa gtttgcttcc  2040
ttcatcacac agtactccac gggacaggtc agcgtggaga tcgagtggga gctgcagaag  2100
gaaaacagca aacgctggaa tcccgaaatt cagtacactt ccaactacaa caagtctgtt  2160
aatgtggact ttactgtgga cactaatggc gtgtattcag agcctcgccc cattggcacc  2220
agatacctga ctcgtaatct gtaa                                             2244

SEQ ID NO: 15           moltype = DNA  length = 2244
FEATURE                 Location/Qualifiers
misc_feature            1..2244
                        note = LAE coding sequence
source                  1..2244
                        mol_type = other DNA
                        organism = synthetic construct
SEQUENCE: 15
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
```

```
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cgccgccgcc ctggccgagc ccagcaggcc cgccgccaga  1800
caagcagcta ccgcagatgt caacacacaa ggcgttcttc caggcatggt ctggcaggac  1860
agagatgtgt accttcaggg gcccatctgg gcaaagattc cacacacgga cggacatttt  1920
cacccctctc ccctcatggg tggattcgga cttaaacacc ctcctccaca gattctcatc  1980
aagaacaccc cagtacctgc gaatccttcg accaccttca gtgcggcaaa gtttgcttcc  2040
ttcatcacac agtactccac gggacaggtc agcgtggaga tcgagtggga gctgcagaag  2100
gaaaacagca aacgctggaa tcccgaaatt cagtacactt ccaactacaa caagtctgtt  2160
aatgtggact ttactgtgga cactaatggc gtgtattcag agcctcgccc cattggcacc  2220
agatacctga ctcgtaatct gtaa                                        2244

SEQ ID NO: 16          moltype = DNA  length = 2244
FEATURE                Location/Qualifiers
misc_feature           1..2244
                       note = LGP coding sequence
source                 1..2244
                       mol_type = other DNA
                       organism = synthetic construct
SEQUENCE: 16
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cgccctggcc ctgggccccc ccagcaagcc cgccgccaga  1800
caagcagcta ccgcagatgt caacacacaa ggcgttcttc caggcatggt ctggcaggac  1860
agagatgtgt accttcaggg gcccatctgg gcaaagattc cacacacgga cggacatttt  1920
cacccctctc ccctcatggg tggattcgga cttaaacacc ctcctccaca gattctcatc  1980
aagaacaccc cagtacctgc gaatccttcg accaccttca gtgcggcaaa gtttgcttcc  2040
ttcatcacac agtactccac gggacaggtc agcgtggaga tcgagtggga gctgcagaag  2100
gaaaacagca aacgctggaa tcccgaaatt cagtacactt ccaactacaa caagtctgtt  2160
aatgtggact ttactgtgga cactaatggc gtgtattcag agcctcgccc cattggcacc  2220
agatacctga ctcgtaatct gtaa                                        2244

SEQ ID NO: 17          moltype = DNA  length = 2244
FEATURE                Location/Qualifiers
```

```
misc_feature          1..2244
                      note = NSP coding sequence
source                1..2244
                      mol_type = other DNA
                      organism = synthetic construct
SEQUENCE: 17
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cgccgccggc aacagcccca ccggcaggaa cgccgccaga  1800
caagcagcta ccgcagatgt caacacacaa ggcgttcttc caggcatggt ctggcaggac  1860
agagatgtgt accttcaggg gcccatctgg gcaaagattc cacacacgga cggacatttt  1920
cacccctctc ccctcatggg tggattcgga cttaaacacc ctcctccaca gattctcatc  1980
aagaacaccc cagtacctgc gaatccttcg accaccttca gtgcggcaaa gtttgcttcc  2040
ttcatcacac agtactccac gggacaggtc agcgtggaga tcgagtggga gctgcagaag  2100
gaaaacagca aacgctggaa tcccgaaatt cagtacactt ccaactacaa caagtctgtt  2160
aatgtggact ttactgtgga cactaatggc gtgtattcag agcctcgccc cattggcacc  2220
agatacctga ctcgtaatct gtaa                                        2244

SEQ ID NO: 18         moltype = AA  length = 736
FEATURE               Location/Qualifiers
source                1..736
                      mol_type = protein
                      organism = Adeno-associated virus 9
SEQUENCE: 18
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 19         moltype = DNA  length = 3013
FEATURE               Location/Qualifiers
misc_feature          1..3013
                      note = rAAV genome encoding GFP
source                1..3013
                      mol_type = other DNA
                      organism = synthetic construct
SEQUENCE: 19
actccatcac taggggttcc ttgtagttaa tgattaaccc gccatgctac ttatctacca  60
gggtaatggg gatcctctag aactatagct agtcgacata acgcgtcaat tgctagtcga  120
cattgattat tgactagtta ttaatagtaa tcaattacgg ggtcattagt tcatagccca  180
tatatggagt tccgcgttac ataacttacg gtaaatggcc cgcctggctg accgcccaac  240
gacccccgcc cattgacgtc aataatgacg tatgttccca tagtaacgcc aatagggact  300
ttccattgac gtcaatgggt ggagtattta cggtaaactg cccacttggc agtacatcaa  360
```

-continued

```
gtgtatcata tgccaagtac gccccctatt gacgtcaatg acggtaaatg gcccgcctgg  420
cattatgccc agtacatgac cttatgggac tttcctactt ggcagtacat ctacgtatta  480
gtcatcgcta ttaccatggt cgaggtgagc cccacgttct gcttcactct ccccatctcc  540
ccccccctccc cacccccaat tttgtattta tttatttttt aattattttg tgcagcgatg  600
gggggcgggg gggggggggg gcgcgcgcca ggcggggcgg ggcggggcga ggggcggggc  660
ggggcgaggc ggagaggtgc ggcggcagcc aatcagagcg gcgcgctccg aaagtttcct  720
tttatggcga ggcggcggcg gcggcggccc tataaaaagc gaagcgcgcg gcgggcggaa  780
gcttcgttta gtgaaccgtc agatcgcctg gagacgccat ccacgctgtt ttgacctcca  840
tagaagacac cgggaccgat ccagcctccg cggattcgaa tcccggccgg gaacggtgca  900
ttggaacgcg gattccccgt gccaagagtg acgtaagtac cgcctataga gtctataggc  960
ccacaaaaaa tgctttcttc ttttaatata cttttttgtt tatcttattt ctaatacttt  1020
ccctaatctc tttctttcag ggcaataatg atacaatgta tcatgcctct ttgcaccatt  1080
ctaaagaata acagtgataa tttctgggtt aaggcaatag caatatttct gcatataaat  1140
atttctgcat ataaattgta actgatgtaa gaggtttcat attgctaata gcagctacaa  1200
tccagctacc attctgcttt tattttatgg ttgggataag gctggattat tctgagtcca  1260
agctaggccc ttttgctaat catgttcata cctcttatct tcctcccaca gctcctgggc  1320
aacgtgctgg tctgtgtgct ggcccatcac tttggcaaag aattgagctc cttcctactc  1380
aaagccacat gaataggagg agccaccatg agtcctgccc agttcctgtt tctgttagtg  1440
ctctggattc gggaaaccaa cggtgatgtt gtgaccggtg ccgccaccat ggtgagcaag  1500
ggcgaggagc tgttcaccgg ggtggtgccc atcctggtcg agctggacgg cgacgtaaac  1560
ggccacaagt tcagcgtgtc cggcgagggc gagggcgatg ccacctacgg caagctgacc  1620
ctgaagttca tttgcaccac cggcaagctg cccgtgccct ggcccaccct cgtgaccacc  1680
ctgacctacg gcgtgcagtg cttcagccgc taccccgacc acatgaagca gcacgacttc  1740
ttcaagtccg ccatgcccga aggctacgtc caggagcgca ccatcttctt caaggacgac  1800
ggcaactaca agacccgcgc cgaggtgaag ttcgagggcg acaccctggt gaaccgcatc  1860
gagctgaagg gcatcgactt caaggaggac ggcaacatcc tggggcacaa gctggagtac  1920
aactacaaca gccacaacgt ctatatcatg gccgacaagc agaagaacgg catcaaggtg  1980
aacttcaaga tccgccacaa catcgaggac ggcagcgtgc agctcgccga ccactaccag  2040
cagaacaccc ccatcggcga cggccccgtg ctgctgcccg acaaccacta cctgagcacc  2100
cagtccgccc tgagcaaaga ccccaacgag aagcgcgatc acatggtcct gctggagttc  2160
gtgaccgccg ccgggatcac tctcggcatg gacgagctgt acaagtaata gtaatagtgt  2220
acaggtacct cgatggattt ccaaggttaa ttcattggaa ttgaaaatta acagagatct  2280
agagctgaat tcctgcagcc agggggatca gcctgggtgg catccctgtg acccctcccc  2340
agtgcctctc ctggccctgg aagttgccac tccagtgccc accagccttg tcctaataaa  2400
attaagttgc atcattttgt ctgactaggt gtccttctat aatattatgg ggtggagggg  2460
ggtggtatgg agcaaggggc aagttgggaa gacaacctgt agggcctgcg ggtctattg  2520
ggaaccaagc tggagtgcag tggcacaatc ttggctcact gcaatctccg cctcctgggt  2580
tcaagcgatt ctcctgcctc agcctcccga gttgttggga ttccaggcat gcatgaccag  2640
gctcagctaa tttttgtttt tttggtagag acggggtttc accatattgg ccaggctggt  2700
ctccaactcc taatctcagg tgatctaccc accttggcct cccaaattgc tgggattaca  2760
ggcgtgaacc actgctccct tccctgtcct tcggaccgag cggccgcgcc taggtagata  2820
agtagcatgg cgggttaatc attaactaca aggaacccct agtgatggag ttggccactc  2880
cctctctgcg cgctcgctcg ctcactgagg ccgggcgacc aaaggtcgcc cgacgcccgg  2940
gctttgcccg ggcggcctca gtgagcgagc gagcgcgcag ccctgcctgc aggcatttaa  3000
ttaacctaat tcg                                                    3013

SEQ ID NO: 20          moltype = DNA  length = 4775
FEATURE                Location/Qualifiers
misc_feature           1..4775
                       note = rAAV genome encoding bi-vilant Nb24
source                 1..4775
                       mol_type = other DNA
                       organism = synthetic construct
SEQUENCE: 20
caattgacat tattgaagca tttatcaggg ttattgtctc agactgcgcg ctcgctcgct  60
cactgaggcc gcccgggcaa agcccgggcg tcgggcgacc tttggtcgcc cggcctcagt  120
gagcgagcga gcgcgcagag agggagtggc caactccatc actaggggtt ccttgtagtt  180
aatgattaac ccgccatgct acttatctac cagggtaatg gggatcctct agaactatag  240
ctagtcgaca taacgcgtca attgctagtc gacattgatt attgactagt tattaatagt  300
aatcaattac ggggtcatta gttcatagcc catatatgga gttccgcgtt acataactta  360
cggtaaatgg cccgcctggc tgaccgccca acgacccccg cccattgacg tcaataatga  420
cgtatgttcc catagtaacg ccaataggga ctttccattg acgtcaatgg gtggagtatt  480
tacggtaaac tgcccacttg gcagtacatc aagtgtatca tatgccaagt acgcccccta  540
ttgacgtcaa tgacggtaaa tggcccgcct ggcattatgc ccagtacatg accttatggg  600
actttcctac ttggcagtac atctacgtat tagtcatcgc tattaccatg gtcgaggtga  660
gccccacgtt ctgcttcact ctccccatct cccccccctc ccacccccca attttgtatt  720
tatttatttt ttaattattt tgtgcagcga tgggggcggg gggggggggg gggcgcgcgc  780
caggcggggc ggggcggggc gaggggcggg gcggggcgag gcggagaggt gcggcggcag  840
ccaatcagag cggcgcgctc cgaaagtttc cttttatggc gaggcggcgg cggcggcggc  900
cctataaaaa gcgaagcgcg cggcgggcgg aagcttcgtt tagtgaaccg tcagatcgcc  960
tggagacgcc atccacgctg ttttgacctc catagaagac accgggaccg atccagcctc  1020
cgcggattcg aatcccggcc gggaacggtg cattggaacg cggattcccc gtgccaagag  1080
tgacgtaagt accgcctata gagtctatag gcccacaaaa aatgctttct tcttttaata  1140
tactttttttg tttatcttat ttctaatact ttccctaatc tctttctttc agggcaataa  1200
tgatacaatg tatcatgcct ctttgcacca ttctaaagaa taacagtgat aatttctggg  1260
ttaaggcaat agcaatattt ctgcatataa atatttctgc atataaattg taactgatgt  1320
aagaggtttc atattgctaa tagcagctac aatccagcta ccattctgct tttattttat  1380
ggttgggata aggctggatt attctgagtc caagctaggc ccttttgcta atcatgttca  1440
tacctcttat cttcctccca cagctcctgg gcaacgtgct ggtctgtgtg ctggcccatc  1500
```

```
actttggcaa agaattgagc tccttcctac tcaaagccac atgaatagga ggagccacca  1560
tgagtcctgc ccagttcctg tttctgttag tgctctggat tcgggaaacc aacggtgatg  1620
ttgtgaccgg tgccgccacc atgaagtacc tgctgcccac cgccgccgcc ggcctgctgc  1680
tgctggccgc ccagcccgcc atggccgagg tgcagctgca ggagagcggc ggcggcctgg  1740
tgcagcccgg cggcagcctg aggctgagct gcaccgccag cggcttcacc ttcgacgacc  1800
ccgacgtggg ctggttcagg caggcccccg gcaacgagtg cgagctggtg agcaccatca  1860
gcaaggacgg cagcacctac tacaccgaca gcgtgaaggg caggttcacc atcagcaggg  1920
actacgccaa gaacaccgtg tacctgcaga tgaacagcct gagggccgag gacaccgccg  1980
tgtactactg cgccgccgac agcaaccccca tcgcccccat caggacctgc ctgggctggt  2040
acaactactg gggccagggc accctggtga ccgtgagcag cggaggaggc ggctctggcg  2100
gaggcggctc tgaagtgcaa ctgcaggagt ccggtggggg tctggttcag cccggcggat  2160
ccctgcggct tagctgtacc gcgtccggtt tcaccttcga tgaccctgac gtgggctggt  2220
tccgtcaggc cccaggcaac gagtgtgaac tggtgtccac catctccaag gatgggtcca  2280
cctactatac cgattctgtg aaaggccgct ttaccatcag tcgcgattac gctaagaata  2340
ccgtgtactt gcagatgaat tccctccgtg ccgaggacac cgcggtttac tattgtgccg  2400
cagacagcaa ccctattgct cccatcagaa cctgccttgg ttggtacaat tactggggtc  2460
agggaacctt ggtcacagtg tctagctaat agtgtacagg tacctcgatg gatttccaag  2520
gttaattcat tggaattgaa aattaacaga gatctagagc tgaattcctg cagccagggg  2580
gatcagcctg ggtggcatcc ctgtgacccc tccccagtgc ctctcctggc cctggaagtt  2640
gccactccag tgcccaccag ccttgtccta ataaaattaa gttgcatcat tttgtctgac  2700
taggtgtcct tctataatat tatggggtgg aggggggtgg tatggagcaa ggggcaagtt  2760
gggaagacaa cctgtagggc ctgcggggtc tattgggaac caagctggag tgcagtggca  2820
caatcttggc tcactgcaat ctccgcctcc tgggttcaag cgattctcct gcctcagcct  2880
cccgagttgt tgggattcca ggcatgcatg accaggctca gctaattttt gtttttttgg  2940
tagagacggg gtttcaccat attggccagg ctggtctcca actcctaatc tcaggtgatc  3000
tacccacctt ggcctcccaa attgctggga ttacaggcgt gaaccactgc tcccttccct  3060
gtccttcgga ccgagcggcc gcggtactaa ttaactaata aagcacagaa gaggaaaaaa  3120
tcaaagctag atggatgata gatacataga tagataggaa gatttttttt aatgactcaa  3180
gggagtcctg aaaggaaata ccagacttgt ctttctgact acagatgaac agacataaaa  3240
caagtgtgcc tattttccat tgaagaaaaa caagcatttt ttctaaagcc agaaaaacct  3300
acatctgaaa agaaaaaaga aactattcta agttaagaaa ataattcttt cttggataaa  3360
ttatgtcaac ttttaacttc ctagaaattg taggcattat ttattagaag tcagtaacca  3420
actctagctt tttccttgta gaagtccctg ggaaaggcct acccaaacat aaaatcctta  3480
ctgttgaata caattgttac taattgacaa attcaggcct ttgtcactct cacatatact  3540
ttgtgcatac tttttcattt aacaaatgaa aagaataata ttagtccatt tagttttcac  3600
cacaacatta taatgtaata tattgttaaa tacaaagaaa cctaaaaaaa tctcaaattc  3660
atcatgactg aatagaaact ttgaattgat tttcctatat ctaatgaaga gccctagctt  3720
taaaacaaaa ttgatgaaac ctaaaagaat cttttctttt ttttttttt ttttgagat  3780
ggagtctcgc tctttcgccc agactggagt gcagtggcac tatctcggct cacttgcaag  3840
ctccgcctcc cgagttcacg ccattcttct gcctcagcct cccgagtagc tgggactaca  3900
ggcgcccgcc atcacgcccg gctaattttt tgtatcttta gtagagacgg ggtttcaccg  3960
tgtgccaggg tggtctcgat ctcctgacct cgtcatccgc ccacctcggc ctcccaaagt  4020
gctgggatta cagtcatgag ccaccgcgcc cggccaagaa tcttttctta cagtactaat  4080
gaggcatttt gcatatgtgc atcctactaa aagattaata gtttagaaat taaaatattt  4140
aattctcaat gatatctgca tacttaaaat taatgtttct taagaaatac ttgaacaatt  4200
gcatcttctg gatttgcaaa gtaaaaattt ctgcattttt ctctgaaaac ctctggcatt  4260
aattctatat gaacattcta tactgagaga aataaaccta cataattgtt agtcatttct  4320
aaatttcctg ttcttcaaac tttgaaactc tgtttagtca gtcatcaacg ggctctggca  4380
tgagggtaaa tgcaaatatt tagagtaaga gttataaata tggtttagag attctcttta  4440
ctcggtaaac agaaaaatag ccccaatgat ttttaaatgt tttctcatct ttgtgggaga  4500
agtttaaaaa tagagagtag ttaagaaaag tattttcttt agaaagaata agtgtactga  4560
tcgcggccgc gcctaggtag ataagtagca tggcgggtta atcattaact acaaggaacc  4620
cctagtgatg gagttggcca ctccctctct gcgcgctcgc tcgctcactg aggccgggcg  4680
accaaaggtc gcccgacgcc cgggctttgc ccgggcggcc tcagtgagcg agcgagcgcg  4740
cagccctgcc tgcaggcatt taattaacct aattc                            4775

SEQ ID NO: 21          moltype = AA  length = 745
FEATURE                Location/Qualifiers
REGION                 1..745
                       note = 7m8
source                 1..745
                       mol_type = protein
                       organism = synthetic construct
SEQUENCE: 21
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNLAL GETTRPARQA  600
ATADVNTQGV LPGMVWQDRD VYLQGPIWAK IPHTDGHFHP SPLMGGFGLK HPPPQILIKN  660
TPVPANPSTT FSAAKFASFI TQYSTGQVSV EIEWELQKEN SKRWNPEIQY TSNYNKSVNV  720
DFTVDTNGVY SEPRPIGTRY LTRNL                                         745

SEQ ID NO: 22          moltype = AA  length = 738
```

```
FEATURE                 Location/Qualifiers
source                  1..738
                        mol_type = protein
                        organism = Adeno-associated virus RH10
SEQUENCE: 22
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                                738

SEQ ID NO: 23           moltype = DNA  length = 1866
FEATURE                 Location/Qualifiers
source                  1..1866
                        mol_type = other DNA
                        organism = adeno-associated virus 2
SEQUENCE: 23
atgccggggt tttacgagat tgtgattaag gtccccagcg accttgacga gcatctgccc  60
ggcatttctg acagctttgt gaactgggtg gccgagaagg aatgggagtt gccgccagat  120
tctgacatgg atctgaatct gattgagcag gcacccctga ccgtggccga gaagctgcag  180
cgcgactttc tgacggaatg gcgccgtgtg agtaaggccc cggaggctct tttctttgtg  240
caatttgaga agggagagag ctacttccac atgcacgtgc tcgtggaaac caccggggtg  300
aaatccatgg ttttgggacg tttcctgagt cagattcgcg aaaaactgat tcagagaatt  360
taccgcggga tcgagccgac tttgccaaac tggttcgcgg tcacaaagac cagaaatggc  420
gccggaggcg ggaacaaggt ggtggatgag tgctacatcc ccaattactt gctccccaaa  480
acccagcctg agctccagtg ggcgtggact aatatggaac agtatttaag cgcctgtttg  540
aatctcacgg agcgtaaacg gttggtggcg cagcatctga cgcacgtgtc gcagacgcag  600
gagcagaaca aagagaatca gaatcccaat tctgatgcgc cggtgatcag atcaaaaact  660
tcagccaggt acatggagct ggtcgggtgg ctcgtggaca aggggattac ctcggagaag  720
cagtggatcc aggaggacca ggcctcatac atctccttca atgcggcctc caactcgcgg  780
tcccaaatca aggctgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatccccaa tatgcggctt ccgtctttct gggatgggcc  960
acgaaaaagt tcggcaagag gaacaccatc tggctgtttg ggcctgcaac taccgggaag  1020
accaacatcg cggaggccat agcccacact gtgcccttct acgggtgcgt aaactggacc  1080
aatgagaact ttcccttcaa cgactgtgtc gacaagatgg tgatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaaat gttctcgtca cgtgggcatg  1620
aatctgatgc tgtttccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caataa                                                             1866

SEQ ID NO: 24           moltype = AA  length = 125
FEATURE                 Location/Qualifiers
REGION                  1..125
                        note = Nb24
source                  1..125
                        mol_type = protein
                        organism = synthetic construct
SEQUENCE: 24
EVQLQESGGG LVQPGGSLRL SCTASGFTFD DPDVGWFRQA PGNECELVST ISKDGSTYYT  60
DSVKGRFTIS RDYAKNTVYL QMNSLRAEDT AVYYCAADSN PIAPIRTCLG WYNYWGQGTL  120
VTVSS                                                              125

SEQ ID NO: 25           moltype = DNA  length = 2208
FEATURE                 Location/Qualifiers
source                  1..2208
                        mol_type = other DNA
                        organism = adeno-associated virus 2
SEQUENCE: 25
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
```

```
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccagtac ctgcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga aattcagtac  2100
acttccaact acaacaagtc tgttaatgtg gactttactg tggacactaa tggcgtgtat  2160
tcagagcctc gccccattgg caccagatac ctgactcgta atctgtaa              2208

SEQ ID NO: 26          moltype = DNA  length = 2238
FEATURE                Location/Qualifiers
misc_feature           1..2238
                       note = 7m8 coding sequence
source                 1..2238
                       mol_type = other DNA
                       organism = synthetic construct
SEQUENCE: 26
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cctagcactc ggcgaaacaa caagacctgc tagacaagca  1800
gctaccgcag atgtcaacac acaaggcgtt cttccaggca tggtctggca ggacagagat  1860
gtgtaccttc aggggcccat ctgggcaaag attccacaca cggacggaca ttttcacccc  1920
tctcccctca tgggtggatt cggacttaaa caccctcctc cacagattct catcaagaac  1980
accccagtac ctgcgaatcc ttcgaccacc ttcagtgcgg caaagtttgc ttccttcatc  2040
acacagtact ccacgggaca ggtcagcgtg gagatcgagt gggagctgca gaaggaaaac  2100
agcaaacgct ggaatcccga aattcagtac acttccaact acaacaagtc tgttaatgtg  2160
```

-continued

```
gactttactg tggacactaa tggcgtgtat tcagagcctc gccccattgg caccagatac  2220
ctgactcgta atctgtaa                                                2238

SEQ ID NO: 27          moltype = DNA  length = 2214
FEATURE                Location/Qualifiers
source                 1..2214
                       mol_type = other DNA
                       organism = Adeno-associated virus RH10
SEQUENCE: 27
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccagcagcc cgcgaaaaag agactcaact ttgggcagac tggcgactca  540
gagtcagtgc ccgaccctca accaatcgga gaaccccccg caggcccctc tggtctggga  600
tctggtacaa tggctgcagg cggtggcgct ccaatggcag acaataacga aggcgccgac  660
ggagtgggta gttcctcagg aaattggcat tgcgattcca catggctggg cgacagagtc  720
atcaccacca gcacccgaac ctgggccctc cccacctaca acaaccacct ctacaagcaa  780
atctccaacg ggacttcggg aggaagcacc aacgacaaca cctacttcgg ctacagcacc  840
ccctgggggt attttgactt taacagattc cactgccact tctcaccacg tgactggcag  900
cgactcatca acaacaactg gggattccgg cccaagagac tcaacttcaa gctcttcaac  960
atccaggtca aggaggtcac gcagaatgaa ggcaccaaga ccatcgccaa taaccttacc  1020
agcacgattc aggtctttac ggactcggaa taccagctcc cgtacgtcct cggctctgcg  1080
caccagggct gcctgcctcc gttcccggcg gacgtcttca tgattcctca gtacgggtac  1140
ctgactctga acaatggcag tcaggccgtg ggccgttcct ccttctactg cctggagtac  1200
tttccttctc aaatgctgag aacgggcaac aactttgagt tcagctacca gtttgaggac  1260
gtgccttttc acagcagcta cgcgcacagc caaagcctgg accggctgat gaacccccctc  1320
atcgaccagt acctgtacta cctgtctcgg actcagtcca cgggaggtac cgcaggaact  1380
cagcagttgc tattttctca ggccgggcct aataacatgt cggctcaggc caaaaactgg  1440
ctacccgggc cctgctaccg gcagcaacgc gtctccacga cactgtcgca aaataacaac  1500
agcaactttg cctggaccgg tgccaccaag tatcatctga atggcagaga ctctctggta  1560
aatcccggtg tcgctatggc aacccacaag gacgacgaag agcgattttt tccgtccagc  1620
ggagtcttaa tgtttgggaa acagggagct ggaaaagaca acgtggacta tagcagcgtt  1680
atgctaacca gtgaggaaga aattaaaacc accaacccag tggccacaga acagtacggc  1740
gtggtggccg ataacctgca acagcaaaac gccgctccta ttgtaggggc cgtcaacagt  1800
caaggagcct tacctggcat ggtctggcag aaccgggacg tgtacctgca gggtcctatc  1860
tgggccaaga ttcctcacac ggacggaaac tttcatccct cgccgctgat gggaggcttt  1920
ggactgaaac acccgcctcc tcagatcctg attaagaata cacctgttcc cgcggatcct  1980
ccaactacct tcagtcaagc taagctggcg tcgttcatca cgcagtacag caccggacag  2040
gtcagcgtgg aaattgaatg ggagctgcag aaagaaaaca gcaaacgctg gaacccagag  2100
attcaataca cttccaacta ctacaaatct acaaatgtgg actttgctgt taacacagat  2160
ggcacttatt ctgagcctcg ccccatcggc acccgttacc tcacccgtaa tctg        2214
```